US012753164B2

(12) United States Patent
Yang et al.

(10) Patent No.: US 12,753,164 B2
(45) Date of Patent: Oct. 6, 2026

(54) PYRIMIDINE-4,6-DIAMINE DERIVATIVE, A PREPARATION METHOD THEREFOR, AND A PHARMACEUTICAL APPLICATION THEREOF

(71) Applicant: Abbisko Therapeutics Co., Ltd., Pudong New Area (CN)

(72) Inventors: Fei Yang, Pudong New Area (CN); Shuqun Yang, Pudong New Area (CN); Hongping Yu, Pudong New Area (CN); Zhui Chen, Pudong New Area (CN); Yaochang Xu, Pudong New Area (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 347 days.

(21) Appl. No.: 18/571,418

(22) PCT Filed: Jul. 28, 2022

(86) PCT No.: PCT/CN2022/108432
§ 371 (c)(1),
(2) Date: Dec. 18, 2023

(87) PCT Pub. No.: WO2023/011299
PCT Pub. Date: Feb. 9, 2023

(65) Prior Publication Data

US 2024/0360102 A1 Oct. 31, 2024

(30) Foreign Application Priority Data

Aug. 2, 2021 (CN) ......................... 202110879406.1
Apr. 20, 2022 (CN) ......................... 202210416287.0

(51) Int. Cl.
*C07D 401/14* (2006.01)
*A61K 31/506* (2006.01)
*A61K 31/5377* (2006.01)

(52) U.S. Cl.
CPC .......... *C07D 401/14* (2013.01); *A61K 31/506* (2013.01); *A61K 31/5377* (2013.01)

(58) Field of Classification Search
CPC . C07D 401/14; A61K 31/506; A61K 31/5377
See application file for complete search history.

(56) References Cited

U.S. PATENT DOCUMENTS 7,982,036 B2 7/2011 Singh et al.
9,296,704 B2 3/2016 Singh et al.
2010/0016296 A1* 1/2010 Singh .................. C07D 403/12 435/15
2017/0369449 A1 12/2017 Gray et al.

FOREIGN PATENT DOCUMENTS

CN 101902911 A 12/2010
CN 102448462 A 5/2012

OTHER PUBLICATIONS

Bray, F. et al. Global cancer statistic 2018: GLOBOCAN estimates of incidence and mortality worldwide for 36 cancers in 185 countries: *CA: a cancer journal for clinicians* 68, 394-424, 2018.

Hirsch, F. R. et al. Lung cancer: current therapies and new targeted treatments. *Lancet* 389, 299-311, 2017.

Passaro, A., Jänne, P.A., Mok, T. et al. Overcoming therapy resistance in EGFT-mutant lung cancer. *Nat Cancer* 2, 377-391, 2021.

Passaro, A., et al. Recent Advances on the Role of EGFR Tyrosine Kinase Inhibitors in the Management of NSCLC With Uncommon, Non Exon 20 Insertions, EGFR Mutations, vol. 16, No. 5, J. Thoracic Oncology, 764-773, 2021.

Rosell, R. et al. Erlotinib versus standard chemotherapy as first-line treatment for European patients with advanced EGFR mutation-positive non-small-cell lung cancer (EURTAC): a multicentre, open-label, randomised phase 3 trial. *The Lancet. Oncology* 13, 239-246, 2012.

Sequist, L. V. et al. Phase III study of afatinib or cisplatin plus pemetrexed in patients with metastatic lung adenocarcinoma with EGFR mutations. *Journal of clinical oncology : official journal of the American Society of Clinical Oncology* 31, 3327-3334, 2013.

(Continued)

*Primary Examiner* — Jeffrey S Lundgren
*Assistant Examiner* — Brahim D Bori
(74) *Attorney, Agent, or Firm* — Crowell & Moring LLP

(57) ABSTRACT

The present invention relates to a pyrimidine-4,6-diamine derivative, a preparation method therefor, and a pharmaceutical application thereof. Particularly, the present invention relates to a pyrimidine-4,6-diamine derivative having the structure of formula (I), a preparation method therefor, a pharmaceutical composition containing same, and a use of same as an EGFR inhibitor and a use of same in the preparation of drugs for the treatment and/or prevention of cancers, tumors, or metastatic diseases at least partially related to EGFR Del19 mutation, EGFR L858R mutation, EGFR L858R/C797S double mutation or EGFRDel19/C797S double mutation, in particular a use of same in the preparation of drugs for the treatment and/or prevention of hyperproliferative diseases and induced cell death disorders. The definition of each substituent in formula (I) is the same as that in the description.

(I)

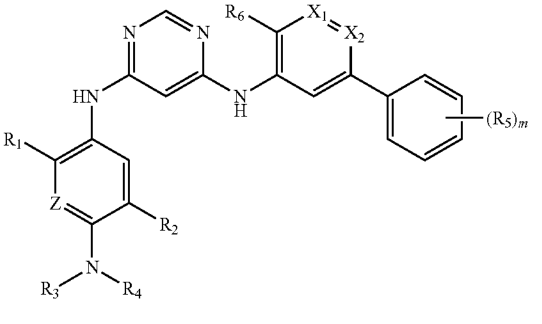

13 Claims, No Drawings

(56) References Cited

OTHER PUBLICATIONS

Mistudomi, T. et al. Gefitinib versus cisplatin plus docetaxel in patients with non-small-cell lung cancer harbouring mutations of the epidermal growth factor receptor (WJTOG3405): an open label, randomised phase 3 trial. *The Lancet. Oncology* 11, 121-128, 2010.
Park, K. et al. Afatinib versus gefitinib as first-line treatment of patients with EGFR mutation-positive non-small-cell lung cancer (LUX-Lung7): a phase 2B, open-label, randomised controlled trial. *The Lancet. Oncology* 17, 577-589, 2016.
Soria, J.-C. et al. Osimertinib in Untreated EGFR-Mutated Advanced Non-Small-Cell Lung Cancer. *The New England journal of medicine* 378, 113-125, 2018.
Ramalingam, S. S. et al. LBA50 Mechanisms of acquired resistance to first-line osimertinib: preliminary data from the phase III FLAURA study. *Ann. Oncol.*, vol. 29, Supp. 8, viii740, 2018.
Tumbrink, H. L., Heimsoeth, A.& Sos, M. L. The next tier of EGFR resistance mutations in lung cancer. *Oncogene* 40, 1-11, 2021.
International Search Report for corresponding PCT Application No. PCT/CN2022/108432, mailed Oct. 27, 2022, with English translation, 8 pgs.
Written Opinion for corresponding PCT Application No. PCT/CN2022/108432, mailed Oct. 27, 2022, 4 pgs.

* cited by examiner

PYRIMIDINE-4,6-DIAMINE DERIVATIVE, A PREPARATION METHOD THEREFOR, AND A PHARMACEUTICAL APPLICATION THEREOF

RELATED APPLICATIONS

This application is a U.S. National Phase entry under 35 U.S.C. § 371 of International Application No. PCT/CN2022/108432, filed 28 Jul. 2022, which claims the benefit of Chinese Patent Application No. 202110879406.1, filed 2 Aug. 2021, and Chinese Patent Application No. 202210416287.0, filed 20 Apr. 2022, the contents of each of which are incorporated herein by reference in their entireties.

TECHNICAL FIELD

The present invention belongs to the field of pharmaceutical synthesis, and particularly relates to a pyrimidine-4,6-diamine derivative, preparation method therefor and pharmaceutical application thereof.

BACKGROUND

Lung cancer is the malignant tumor with the highest mortality rate around the world, posing a severe threat to human health, with non-small-cell lung cancer (NSCLC) accounting for about 85% of all lung cancers (Bray. F. et al. Global cancer statistics 2018: GLOBOCAN estimates of incidence and mortality worldwide for 36 cancers in 185 countries, *CA: a cancer journal for clinicians* 68, 394-424, 2018). At present, molecular mechanisms such as mutations and expression abnormalities of various genes have been confirmed to be associated with the pathogenesis of NSCLC, with EGFR being the major driver gene. The frequency of EGFR-activating mutations in NSCLC patients worldwide is about 17% (Hirsch, F, R. et al. Lung cancer: current therapies and new targeted treatments, *Lancet* 389, 299-311, 2017), and East Asian populations are more sensitive, with a mutation frequency of about 50% (Passaro, A., Jänne, P. A., Mok, T. et al. Overcoming therapy resistance in EGFR-mutant lung cancer. *Nat Cancer* 2, 377-391, 2021). EGFR-activating mutations mainly occur in exons 18-21, with the deletion mutation in exon 19 (Del19) and L858R point mutation in exon 21 being the most common subtypes, accounting for more than 80% of all mutation types (Passaro, A. et al. Recent Advances on the Role of EGFR Tyrosine Kinase Inhibitors in the Management of NSCLC With Uncommon, Non Exon 20 Insertions, EGFR Mutations, *Journal of thoracic oncology: official publication of the International Association for the Study of Lung Cancer* 16, 764-773, 2021). These mutations can lead to ligand-independent receptor activation and promote the survival and proliferation of tumor cells. The first- and second-generation EGFR tyrosine kinase inhibitors (TKIs) are mainly directed against these two activating mutations. Compared with platinum-based chemotherapy, the first- and second-generation EGFR TKIs can significantly prolong progression-free survival (Rosell, R. et al. Erlotinib versus standard chemotherapy as first-line treatment for European patients with advanced EGFR mutation-positive non-small-cell lung cancer (EURTAC): a multicentre, open-label, randomised phase 3 trial. *The Lancet. Oncology* 13, 239-246, 2012); (Sequist, L. V. et al. Phase III study of afatinib or cisplatin plus pemetrexed in patients with metastatic lung adenocarcinoma with EGFR mutations, *Journal of clinical oncology: official journal of the American Society of Clinical Oncology* 31, 3327-3334, 2013), but resistance often occurs after 10-12 months of dosing (Mitsudomi, T. et al. Gefitinib versus cisplatin plus docetaxel in patients with non-small-cell lung cancer harbouring mutations of the epidermal growth factor receptor (WJTOG3405): an open label, randomised phase 3 trial. *The Lancet. Oncology* 11, 121-128, 2010); (Park, K. et al. Afatinib versus gefitinib as first-line treatment of patients with EGFR mutation-positive non-small-cell lung cancer (LUX-Lung 7): a phase 2B, open-label, randomised controlled trial. *The Lancet. Oncology* 17, 577-589, 2016). EGFR T790M mutation is the primary mechanism of the resistance to first- and second-generation EGFR TKIs, and subsequently, the third-generation EGFR TKI, osimertinib, was developed to selectively inhibit EGFR T790M and EGFR common mutations. In the results of the phase III clinical FLAURA study, osimertinib showed superior efficacy compared with the first-generation EGFR TKIs, significantly improving the progression-free survival (18.9 months vs, 10.2 months) and overall survival (38.6 months vs, 31.8 months) (Soria, J, C. et al. Osimertinib in Untreated EGFR-Mutated Advanced Non-Small-Cell Lung Cancer. *The New England journal of medicine* 378, 113-125, 2018), which also directly propelled osimertinib to enter the cohort of first-line treatment options.

Despite the significant efficacy of osimertinib, resistance inevitably occurs and leads to disease progression. Several EGFR-dependent (on-target) and non-dependent (off-target) resistance mechanisms have been reported in both preclinical and clinical studies (Passaro, A., Jänne. P. A., Mok, T. et al. Overcoming therapy resistance in EGFR-mutant lung cancer. *Nat Cancer* 2, 377-391, 2021). Analysis of the phase III clinical FLAURA study showed that, with the first-line treatment of advanced NSCLC using osimertinib, about 10%-15% of patients exhibited EGFR-dependent resistance, with C797S on exon 20 being the most prominent non-dependent mutation and accounting for 7% (Ramalingam, S. S. et al. LBA50 Mechanisms of acquired resistance to first-line osimertinib: preliminary data from the phase III FLAURA study. *Ann. Oncol.* 2018). The C797S mutation is located in the tyrosine kinase domain of EGFR, rendering osimertinib incapable of forming a covalent bond in the ATP-binding domain of EGFR, thereby conferring resistance. Furthermore, there is no evidence that patients receiving the first-line treatment using osimertinib develop an acquired mutation of EGFR T790M (Ramalingam, S. S. et al. LBA50 Mechanisms of acquired resistance to first-line osimertinib: preliminary data from the phase III FLAURA study. *Ann. Oncol.* 2018). Therefore, the double mutation composed of Del19/L858R and C797S may be one of the important mechanisms of resistance to first-line treatment using osimertinib (Tumbrink, H. L., Heimsoeth, A. & Sos, M. L. The next tier of EGFR resistance mutations in lung cancer. *Oncogene* 40, 1-11, 2021), while a new generation of EGFR TKIs with a high degree of activity and selectivity against the double mutation composed of Del19/L858R and C797S has the potential to serve as a new-generation therapeutic means after the resistance to first-line treatment using osimertinib, meeting the clinical needs of these patients.

SUMMARY

The object of the present invention is to provide a pyrimidine-4,6-diamine derivative, preparation method therefor and pharmaceutical application thereof. A series of compounds of the present invention have strong inhibitory effects on the cytological activity of EGFR Del19 mutation, EGFR L858R mutation, EGFR L858R/C797S double mutation or EGFR Del19/C797S double mutation, have high selectivity for EGFR wild type, and can be widely applied to the preparation of medicaments for treating and/or preventing cancer, tumor or metastatic disease at least partially related to EGFR Del19 mutation, EGFR L858R mutation, EGFR L858R/C797S double mutation or EGFR Del19/C797S double mutation, particularly medicaments for treating hyperproliferative disease and disease of dysfunction in cell death induction, so that a new generation of EGFR inhibitors is expected to be developed.

The first aspect of the present invention provides a compound of formula (I), a stereoisomer or pharmaceutically acceptable salt thereof:

(I)

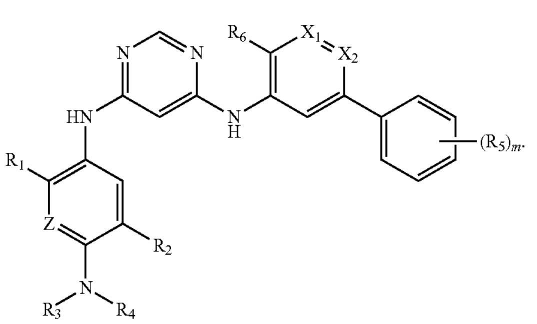

wherein, $X_1$ and $X_2$ are each independently N or $CR_7$;

Z is N or CH;

$R_1$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, hydroxy, $C_{1-10}$ alkoxy, $C_{3-12}$ cycloalkyloxy, 3-12 membered heterocyclyloxy, $C_{6-10}$ aryloxy, 5-10 membered heteroaryloxy, $—SF_5$, $—S(O)_rR_8$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$ and $—C(O)NR_{11}R_{12}$, the above groups are independently optionally further substituted with one or more substituents selected from the group consisting of deuterium, halogen, hydroxy, =O, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and $—NR_{11}R_{12}$;

$R_2$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, $—C_{0-8}$ alkyl-$SF_5$, $—C_{0-8}$ alkyl-$S(O)_rR_8$, $—C_{0-8}$ alkyl-O—$R_9$, $—C_{0-8}$ alkyl-$C(O)OR_9$, $—C_{0-8}$ alkyl-$C(O)R_{10}$, $—C_{0-8}$ alkyl-O—$C(O)R_{10}$, $—C_{0-8}$ alkyl-$NR_{11}R_{12}$, $—C_{0-8}$ alkyl-$C(=NR_{11})R_{10}$, $—C_{0-8}$ alkyl-$N(R_{11})—C(=NR_{12})R_{10}$ and $—C_{0-8}$ alkyl-$C(O)NR_{11}R_{12}$, the above groups are independently optionally further substituted with one or more substituents selected from the group consisting of deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, $—C_{0-8}$ alkyl-$SF_5$, $—C_{0-8}$ alkyl-$S(O)_rR_8$, $—C_{0-8}$ alkyl-O—$R_9$, $—C_{0-8}$ alkyl-$C(O)OR_9$, $—C_{0-8}$ alkyl-$C(O)R_{10}$, $—C_{0-8}$ alkyl-O—$C(O)R_{10}$, $—C_{0-8}$ alkyl-$NR_{11}R_{12}$, $—C_{0-8}$ alkyl-$C(=NR_{11})R_{10}$, $—C_{0-8}$ alkyl-$N(R_{11})—C(=NR_2)R_{10}$, $—C_{0-8}$ alkyl-$C(O)NR_{11}R_{12}$ and $—C_{0-8}$ alkyl-$N(R_{11})—C(O)R_{10}$;

$R_3$ and $R_4$ are each independently selected from the group consisting of hydrogen, deuterium, hydroxy, $C_{1-10}$ alkyl, $C_{2-10}$ alkenyl, $C_{3-12}$ cycloalkyl and 3-12 membered heterocyclyl, or $R_3$ and $R_4$, together with the nitrogen atom to which they are directly attached, form a 4-12 membered heterocyclyl, the above group is optionally further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, $—C_{0-8}$ alkyl-$SF_5$, $—C_{0-8}$ alkyl-$S(O)_rR_8$, $—C_{0-8}$ alkyl-O—$R_9$, $—C_{0-8}$ alkyl-$C(O)OR_9$, $—C_{0-8}$ alkyl-$C(O)R_{10}$, $—C_{0-8}$ alkyl-O—$C(O)R_{10}$, $—C_{0-8}$ alkyl-$NR_{11}R_{12}$, $—C_{0-8}$ alkyl-$C(=NR_{11})R_{10}$, $—C_{0-8}$ alkyl-$N(R_{11})—C(=NR_{12})R_{10}$, $—C_{0-8}$ alkyl-$C(O)NR_{11}R_{12}$ and $—C_{0-8}$ alkyl-$N(R_{11})—C(O)R_{10}$, the above groups are optionally more further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{2-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, $—C_{0-8}$ alkyl-$SF_5$, $—C_{0-8}$ alkyl-$S(O)_rR_8$, $—C_{0-8}$ alkyl-O—$R_9$, $—C_{0-8}$ alkyl-$C(O)OR_9$, $—C_{0-8}$ alkyl-$C(O)R_{10}$, $—C_{0-8}$ alkyl-O—$C(O)R_{10}$, $—C_{0-8}$ alkyl-$NR_{11}R_{12}$, $—C_{0-8}$ alkyl-$C(=NR_{11})R_{10}$, $—C_{0-8}$ alkyl-$N(R_{11})—C(=NR_{12})R_{10}$, $—C_{0-8}$ alkyl-$C(O)NR_{11}R_{12}$ and $—C_{0-8}$ alkyl-$N(R_{11})—C(O)R_{10}$;

each $R_5$ is independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, $—C_{0-8}$ alkyl-$SF_5$, $—C_{0-8}$ alkyl-$S(O)_rR_8$, $—C_{0-8}$ alkyl-O—$R_9$, $—C_{0-8}$ alkyl-$C(O)OR_9$, $—C_{0-8}$ alkyl-$C(O)R_{10}$, $—C_{0-8}$ alkyl-O—$C(O)R_{10}$, $—C_{0-8}$ alkyl-$NR_{11}R_{12}$, $—C_{0-8}$ alkyl-$C(=NR_{11})R_{10}$, $—C_{0-8}$ alkyl-$N(R_{11})—C(=NR_{12})R_{10}$, $—C_{0-8}$ alkyl-$C(O)NR_{11}R_{12}$ and $—C_{0-8}$ alkyl-$N(R_{11})—C(O)R_{10}$, or when m≥2, wherein 2 adjacent $R_5$, together with the moiety to which they are directly attached, form a $C_{5-10}$ cycloalkyl, 5-10 membered heterocyclyl, $C_{6-10}$ aryl or 5-10 membered heteroaryl, the above groups are independently optionally further substituted with one or more substituents selected from the group consisting of deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, $—C_{0-8}$ alkyl-$SF_5$, $—C_{0-8}$ alkyl-$S(O)_rR_8$, $—C_{0-8}$ alkyl-O—$R_9$, $—C_{0-8}$ alkyl-$C(O)OR_9$, $—C_{0-8}$ alkyl-$C(O)R_{10}$, $—C_{0-8}$ alkyl-O—$C(O)R_{10}$, $—C_{0-8}$ alkyl-$NR_{11}R_{12}$, $—C_{0-8}$ alkyl-$C(=NR_{11})R_{10}$, $—C_{0-8}$ alkyl-$N(R_{11})—C(=NR_{12})R_{10}$, $—C_{0-8}$ alkyl-$C(O)NR_{11}R_{12}$ and $—C_{0-8}$ alkyl-$N(R_{11})—C(O)R_{10}$, $R_6$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, $—C_{0-8}$ alkyl-$SF_5$, $—C_{0-8}$ alkyl-$S(O)_rR_8$, $—C_{0-8}$ alkyl-O—$R_9$, $—C_{0-8}$ alkyl-$C(O)OR_9$, $—C_{0-8}$ alkyl-$C(O)R_{10}$, $—C_{0-8}$ alkyl-O—$C(O)R_{10}$, $—C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$, the above groups are independently optionally further substituted with one or more substituents selected from the group consisting of deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_2$)$R_{10}$, —$C_{0-8}$ alkyl-C(O)$NR_{11}R_{12}$ and —$C_{0-8}$ alkyl-N($R_{11}$)—C(O)$R_{10}$;

each $R_7$ is independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$, or two $R_7$, together with the moiety to which they are directly attached, form a $C_{5-10}$ cycloalkyl, 5-10 membered heterocyclyl, $C_{6-10}$ aryl or 5-10 membered heteroaryl, the above groups are independently optionally further substituted with one or more substituents selected from the group consisting of deuterium, halogen, cyano, nitro, azido, $C_{1-10}$ alkyl, $C_{1-10}$ haloalkyl, $C_{1-10}$ deuterioalkyl, $C_{1-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$;

each $R_8$ is independently selected from the group consisting of hydrogen, deuterium, hydroxy, $C_{1-10}$ alkyl, $C_{2-10}$ alkenyl, $C_{3-12}$ cycloalkyl, 3-12 membered heterocyclyl, $C_{6-10}$ aryl, 5-10 membered heteroaryl and —$NR_{11}R_{12}$, the above groups are independently optionally further substituted with one or more substituents selected from the group consisting of deuterium, halogen, hydroxy, =O, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$NR_{11}R_{12}$;

each $R_9$ is independently selected from the group consisting of hydrogen, deuterium, $C_{1-10}$ alkyl, $C_{2-10}$ alkenyl, $C_{3-12}$ cycloalkyl, 3-12 membered heterocyclyl. $C_{6-10}$ aryl and 5-10 membered heteroaryl, the above groups are independently optionally further substituted with one or more substituents selected from the group consisting of deuterium, halogen, hydroxy, =O, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$NR_{11}R_{12}$;

each $R_{10}$ is selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$NR_{11}R_{12}$, the above groups are independently optionally further substituted with one or more substituents selected from the group consisting of deuterium, halogen, hydroxy, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$NR_{11}R_{12}$;

each of $R_{11}$ and $R_{12}$ is independently selected from the group consisting of hydrogen, deuterium, hydroxy, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-10}$ alkylamino, di$C_{1-10}$ alkylamino and $C_{1-10}$ alkanoyl, the above groups are independently optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, amino, mono$C_{1-10}$ alkylamino, di$C_{1-10}$ alkylamino and $C_{1-10}$ alkanoyl, or, $R_{11}$ and $R_{12}$, together with the nitrogen atom to which they are directly attached, form a 4-10 membered heterocyclyl or 5-10 membered heteroaryl, the 4-10 membered heterocyclyl or 5-10 membered heteroaryl is optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, amino, mono$C_{1-10}$ alkylamino, di$C_{1-10}$ alkylamino and $C_{1-10}$ alkanoyl;

m is 0, 1, 2, 3, 4 or 5; and each r is independently 0, 1 or 2.

As a preferred embodiment, in the compound of formula (I), the stereoisomer or pharmaceutically acceptable salt thereof, $X_1$ and $X_2$ are each independently N or $CR_7$;

$R_1$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, hydroxy, $C_{1-4}$ alkoxy, $C_{3-6}$ cycloalkyloxy, 3-6 membered heterocyclyloxy, $C_{6-8}$ aryloxy, 5-8 membered heteroaryloxy, —$SF_5$, —S(O)$_r$$R_8$, —C(O)O$R_9$, —C(O)$R_{10}$ and —O—C(O)$R_{10}$, the above groups are independently optionally further substituted with one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{11}R_{12}$;

$R_2$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$ and —$C_{0-4}$ alkyl-C(O)$NR_{11}R_{12}$, the above groups are independently optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

$R_3$ and $R_4$ are each independently selected from the group consisting of hydrogen, deuterium, hydroxy, $C_{1-4}$ alkyl, $C_{2-4}$ alkenyl, $C_{3-6}$ cycloalkyl and 3-6 membered heterocyclyl, or $R_3$ and $R_4$, together with the nitrogen atom to which they are directly attached, form a 4-12 membered monocyclic heterocyclyl or polycyclic heterocyclyl, the above groups are optionally further substituted with one or more substituents selected from the group consisting of deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$, the above groups are optionally more further substituted with one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

each $R_5$ is independently selected from the group consisting of hydrogen, deuterium, halogen, cyano, nitro, azido, $C_{1-4}$ alkyl, $C_{2-4}$ alkenyl, $C_{2-4}$ alkynyl, —$C_{0-4}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$, or when m≥2, wherein 2 adjacent $R_5$, together with the moiety to which they are directly attached, form a $C_{5-8}$ cycloalkyl, 5-8 membered heterocyclyl, $C_{6-8}$ aryl or 5-8 membered heteroaryl, the above groups are independently optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

$R_6$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$, the above groups are independently optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

each $R_7$ is independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)$R_{10}$, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$, or two $R_7$, together with the moiety to which they are directly attached, form a $C_{5-8}$ cycloalkyl, 5-8 membered heterocyclyl, $C_{6-8}$ aryl or 5-8 membered heteroaryl, the above groups are independently optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_9$, —$C_{0-4}$ alkyl-C(O)$R_{10}$, —$C_{0-4}$ alkyl-O—C(O)Rao, —$C_{0-4}$ alkyl-$NR_{11}R_{12}$, —$C_{0-4}$ alkyl-C(=$NR_{11}$)$R_{10}$, —$C_{0-4}$ alkyl-N($R_{11}$)—C(=$NR_{12}$)$R_{10}$, —$C_{0-4}$ alkyl-C(O)$NR_{11}R_{12}$ and —$C_{0-4}$ alkyl-N($R_{11}$)—C(O)$R_{10}$;

wherein, $R_8$, $R_9$, $R_{10}$, $R_{11}$, $R_{12}$, m and r are defined as those in the compound of formula (I).

As a preferred embodiment, in the compound of formula (I), the stereoisomer or pharmaceutically acceptable salt thereof, the compound of formula (I) is a compound of the following formula (ii):

(II)

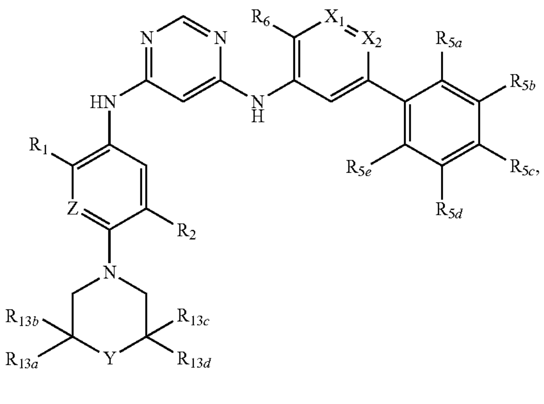

wherein, $X_1$ and $X_2$ are each independently N or $CR_7$;

Z is N or CH;

Y is a bond, O, S, $N(R_{14})$ or $C(R_{15}R_{16})$;

$R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, hydroxy, $C_{1-4}$ alkoxy, $C_{3-6}$ cycloalkyloxy, 3-6 membered heterocyclyloxy, $C_{6-8}$ aryloxy and 5-8 membered heteroaryloxy, the above groups are independently optionally further substituted with one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and $—NR_{11}R_{12}$;

$R_2$ is selected from the group consisting of hydrogen, deuterium, halogen, cyano. $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—S(O)_rR_8$, $—O—R_9$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$ and $—C(O)NR_{11}R_{12}$, the above groups are independently optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $—SF_3$, $—S(O)_rR_8$, $—O—R_9$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$, $—C(O)NR_{11}R_{12}$ and $—N(R_{11})—C(O)R_{10}$;

$R_{5a}$, $R_{5b}$, $R_{5c}$, $R_{5d}$ and $R_{5e}$ are each independently selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—S(O)_rR_8$, $—O—R_9$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$, $—C(O)NR_{11}R_{12}$ and $—N(R_{11})—C(O)R_{10}$;

$R_6$ is selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—S(O)_rR_8$, $—O—R_9$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$, $—C(O)NR_{11}R_{12}$ and $—N(R_{11})—C(O)R_{10}$;

each $R_7$ is independently selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—S(O)_rR_8$, $—O—R_9$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$, $—C(O)NR_{11}R_{12}$ and $—N(R_{11})—C(O)R_{10}$;

$R_{13a}$, $R_{13b}$, $R_{13c}$ and $R_{13d}$ are each independently selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—C_{0-4}$ alkyl-$SF_5$, $—C_{0-4}$ alkyl-$S(O)_rR_8$, $—C_{0-4}$ alkyl-$O—R_9$, $—C_{0-4}$ alkyl-$C(O)OR_9$, $—C_{0-4}$ alkyl-$C(O)R_{10}$, $—C_{0-4}$ alkyl-$O—C(O)R_{10}$, $—C_{0-4}$ alkyl-$NR_{11}R_{12}$, $—C_{0-4}$ alkyl-$C(=NR_{11})R_{10}$, $—C_{0-4}$ alkyl-$N(R_{11})—C(=NR_{12})R_{10}$, $—C_{0-4}$ alkyl-$C(O)NR_{11}R_{12}$ and $—C_{0-4}$ alkyl-$N(R_{11})—C(O)R_{10}$, or each of pairs $R_{13a}/R_{13b}$ and $R_{13c}/R_{13d}$, together with the carbon atom to which they are directly attached, forms a C(O), $C_{3-6}$ cycloalkyl or 3-6 membered heterocyclyl;

$R_{14}$ is selected from the group consisting of hydrogen, deuterium, hydroxy, $C_{1-4}$ alkyl, $C_{1-4}$ haloalkyl, $C_{1-4}$ deuterioalkyl, $C_{3-6}$ cycloalkyl, 3-6 membered heterocyclyl, $—C_{0-4}$ alkyl-$S(O)_rR_8$, $—C_{0-4}$ alkyl-$O—R_9$, $—C_{0-4}$ alkyl-$C(O)OR_9$, $—C_{0-4}$ alkyl-$C(O)R_{10}$ and $—C_{0-4}$ alkyl-$C(O)NR_{11}R_{12}$;

$R_{15}$ and $R_{16}$ are each independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—S(O)_rR_8$, $—O—R_9$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$, $—C(O)NR_{11}R_{12}$ and $—N(R_{11})—C(O)R_{10}$, or $R_{15}$ and $R_{16}$, together with the carbon atom to which they are directly attached, form a C(O), $C_{3-6}$ cycloalkyl or 3-6 membered heterocyclyl, the above groups are optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $—SF_5$, $—S(O)_rR_8$, $—O—R_9$, $—C(O)OR_9$, $—C(O)R_{10}$, $—O—C(O)R_{10}$, $—NR_{11}R_{12}$, $—C(=NR_{11})R_{10}$, $—N(R_{11})—C(=NR_{12})R_{10}$, $—C(O)NR_{11}R_{12}$ and $—N(R_{11})—C(O)R_{10}$;

wherein, $R_8$, $R_9$, $R_{10}$, $R_{11}$, $R_{12}$ and r are defined as those in the compound of formula (I).

As a more further preferred embodiment, in the compound of formula (I), the stereoisomer or pharmaceutically acceptable salt thereof, $R_2$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl and $—SF_5$, the above groups are independently optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $—SF_5$, $—S(O)_rR_8$, $—O—R_9$, $—C(O)OR_9$, $—C(O)R_{10}$, $—O—C(O)R_{10}$, $—NR_{11}R_{12}$, —C(═$NR_{11}$)$R_{10}$, —N($R_{11}$)—C(═$NR_{12}$)$R_{10}$, —C(O)$NR_{11}R_{12}$ and —N($R_{11}$)—C(O)$R_{10}$;

wherein, $R_8$, $R_9$, $R_{10}$, $R_{11}$, $R_{12}$ and r are defined as those in the compound of formula (I).

As a more further preferred embodiment, in the compound of formula (I), the stereoisomer or pharmaceutically acceptable salt thereof, $R_1$ is selected from the group consisting of hydrogen, deuterium, halogen, cyano, $C_{1-4}$ alkyl, allyl, vinyl, ethynyl, $C_{3-6}$ cycloalkyl, 3-6 membered heterocyclyl, hydroxy, $C_{1-4}$ alkoxy, $C_{3-6}$ cycloalkyloxy and 3-6 membered heterocyclyloxy, the above groups are independently optionally further substituted with one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{11}R_{12}$;

$R_{5a}$, $R_{5b}$, $R_{5c}$, $R_{5d}$ and $R_{5e}$ are each independently selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl and 3-6 membered heterocyclyl;

$R_6$ is selected from the group consisting of hydrogen, deuterium, halogen, cyano, $C_{1-4}$ alkyl, $C_{1-4}$ haloalkyl and $C_{1-4}$ deuterioalkyl;

each $R_7$ is independently selected from the group consisting of hydrogen, deuterium, halogen, cyano, $C_{1-4}$ alkyl, $C_{1-4}$ haloalkyl and $C_{1-4}$ deuterioalkyl;

wherein, $R_{11}$ and $R_{12}$ are defined as those in the compound of formula (I).

As a more further preferred embodiment, in the compound of formula (I), the stereoisomer or pharmaceutically acceptable salt thereof, $R_{13a}$, $R_{13b}$, $R_{13c}$, and $R_{13d}$ are each independently selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl and $C_{2-4}$ alkynyl, or each of pairs $R_{13a}$/$R_{13b}$ and $R_{13c}$/$R_{13d}$, together with the carbon atom to which they are directly attached, forms a C(O), $C_{3-6}$ cycloalkyl or 3-6 membered heterocyclyl:

$R_{14}$ is selected from the group consisting of hydrogen, deuterium, hydroxy, $C_{1-4}$ alkyl, $C_{1-4}$ haloalkyl, $C_{1-4}$ deuterioalkyl, $C_{3-6}$ cycloalkyl, 3-6 membered heterocyclyl, —S(O)$_r$$R_8$, —$C_{0-4}$ alkyl-O—$R_9$, —C(O)O$R_9$, —C(O)$R_{10}$ and —C(O)$NR_{11}R_{12}$;

$R_{15}$ and $R_{16}$ are each independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl and 3-6 membered heterocyclyl, or $R_{15}$ and $R_{16}$, together with the carbon atom to which they are directly attached, form a C(O), $C_{3-6}$ cycloalkyl or 3-6 membered heterocyclyl, the above groups are optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl. ═O, —$SF_5$, —S(O)$_r$$R_8$, —O—$R_9$, —C(O)O$R_9$, —C(O)$R_{10}$, —O—C(O)$R_{10}$, —$NR_{11}R_{12}$, —C(═$NR_{11}$)$R_{10}$, —N($R_{11}$)—C(═$NR_{12}$)$R_{10}$, —C(O)$NR_{11}R_{12}$ and —N($R_{11}$)—C(O)$R_{10}$;

wherein, $R_8$, $R_9$, $R_{10}$, $R_{11}$, $R_{12}$ and r are defined as those in the compound of formula (I).

As a preferred embodiment, in the compound of formula (I), the stereoisomer or pharmaceutically acceptable salt thereof, the compound of formula (I) is a compound of the following formula (III):

(III)

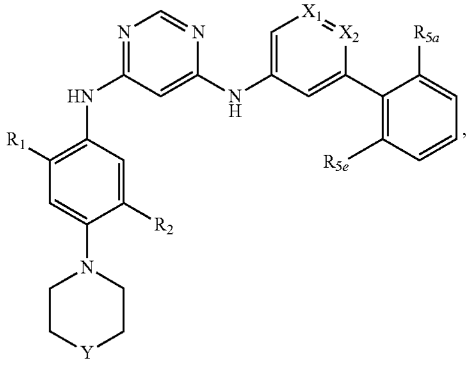

wherein, $X_1$ and $X_2$ are each independently N or CH;

Y is a bond, O, S, N($R_{14}$) or C($R_{15}R_{16}$);

$R_1$ is selected from the group consisting of hydrogen, deuterium, halogen, cyano, methyl, ethyl, isopropyl, allyl, vinyl, ethynyl, cyclopropyl, cyclobutyl, morpholinyl, 3-6 membered oxacyclyl, 3-6 membered azacyclyl, hydroxy, methoxy, ethoxy, isopropoxy, cyclopropyloxy, cyclobutyloxy and 3-6 membered heterocyclyloxy, the above groups are independently optionally further substituted with one or more substituents selected from the group consisting of deuterium, fluoro, chloro, bromo, hydroxy, cyano, $C_{1-4}$ alkyl, $C_{3-6}$ cycloalkyl, 3-6 membered heterocyclyl, amino, mono$C_{1-4}$ alkylamino and di$C_{1-4}$ alkylamino;

$R_2$ is selected from the group consisting of hydrogen, deuterium, fluoro, chloro, bromo, cyano, methyl, ethyl, propyl, isopropyl, cyclopropyl, cyclobutyl, cyclopentyl, azacyclobutyl, pyrazolyl, imidazolyl, oxazolyl and triazolyl, the above groups are independently optionally further substituted with one or more substituents selected from the group consisting of deuterium, fluoro, chloro, bromo, cyano, methyl, ethyl, $C_{1-4}$ haloalkyl, $C_{1-4}$ deuterioalkyl, $C_{2-4}$ alkenyl, $C_{2-4}$ alkynyl, $C_{3-6}$ cycloalkyl and 3-6 membered heterocyclyl;

$R_{5a}$ is selected from the group consisting of hydrogen, deuterium, fluoro, chloro, bromo, cyano, $C_{1-4}$ alkyl, $C_{1-4}$ haloalkyl, $C_{1-4}$ deuterioalkyl and $C_{3-6}$ cycloalkyl;

$R_{5e}$ is selected from the group consisting of hydrogen, deuterium, fluoro, chloro, bromo, cyano, $C_{1-4}$ alkyl, $C_{1-4}$ haloalkyl, $C_{1-4}$ deuterioalkyl and $C_3$ cycloalkyl;

$R_{14}$ is selected from the group consisting of hydrogen, deuterium, hydroxy, methyl, ethyl, propyl, isopropyl, $C_{1-4}$ haloalkyl, $C_{1-4}$ deuterioalkyl, $C_3$ cycloalkyl, 3-6 membered heterocyclyl, —S(O)$_r$$R_8$, —$C_{1-4}$ alkyl-O—$R_9$, —C(O)O$R_9$, —C(O)$R_{10}$ and —C(O)$NR_{11}R_{12}$;

$R_{15}$ and $R_{16}$ are each independently selected from the group consisting of hydrogen, deuterium, fluoro, chloro, bromo, cyano, $C_{1-4}$ alkyl, $C_{2-4}$ alkenyl, $C_{2-4}$ alkynyl, $C_{3-6}$ cycloalkyl and 3-6 membered heterocyclyl, or $R_{15}$ and $R_{16}$, together with the carbon atom to which they are directly attached, form a C(O), $C_{3-6}$ cycloalkyl or 3-6 membered heterocyclyl, the above groups are optionally further substituted with one or more substituents selected from the group consisting of deuterium, fluoro, chloro, bromo, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl and ═O;

wherein, $R_8$, $R_9$, $R_{10}$, $R_{11}$, $R_{12}$ and r are defined as those in the compound of formula (I).

As a more further preferred embodiment, in the compound of formula (I), the stereoisomer or pharmaceutically acceptable salt thereof, each $R_8$ is independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, $C_{6-8}$ aryl, 5-8 membered heteroaryl and —$NR_{11}R_{12}$, the above groups are independently optionally further substituted with one or more substituents selected from the group consisting of deuterium, halogen, hydroxy, =O, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{11}R_{12}$:

each $R_9$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{6-8}$ aryl and 5-8 membered heteroaryl, the above groups are independently optionally further substituted with one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{11}R_{12}$;

each $R_{10}$ is selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{11}R_{12}$, the above groups are independently optionally further substituted with one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-g}$ aryloxy, 5-8 membered heteroaryl, 5-8 membered heteroaryloxy and —$NR_{11}R_{12}$;

each of $R_{11}$ and $R_{12}$ is independently selected from the group consisting of hydrogen, deuterium, hydroxy, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-4}$ alkylamino, di$C_{1-4}$ alkylamino and $C_{1-4}$ alkanoyl, the above groups are independently optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino and $C_{1-4}$ alkanoyl, or, $R_{11}$ and $R_{12}$, together with the nitrogen atom to which they are directly attached, form a 4-8 membered heterocyclyl or 5-8 membered heteroaryl, the 4-8 membered heterocyclyl or 5-8 membered heteroaryl is optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino and $C_{0-4}$ alkanoyl.

As a more further preferred embodiment, in the compound of formula (I), the stereoisomer or pharmaceutically acceptable salt thereof, $R_2$ is selected from the group consisting of hydrogen, deuterium, fluoro, chloro, bromo, methyl, ethyl, propyl, isopropyl, cyclopropyl, cyclobutyl, cyclopentyl, azacyclobutyl, pyrazolyl, imidazolyl, oxazolyl and triazolyl, the above groups are independently optionally further substituted with one or more substituents selected from the group consisting of deuterium, fluoro, chloro, bromo, cyano, methyl, ethyl, trifluoromethyl, difluoromethyl, trideuteriomethyl and dideuteriomethyl.

As a more further preferred embodiment, in the compound of formula (I), the stereoisomer or pharmaceutically acceptable salt thereof, $R_1$ is selected from the group consisting of hydrogen, deuterium, fluoro, chloro, bromo, methyl, ethyl, isopropyl, cyclopropyl, cyclobutyl, morpholinyl, 3-6 membered oxacyclyl, 3-6 membered azacyclyl, hydroxy, methoxy, ethoxy, isopropoxy, cyclopropyloxy and cyclobutyloxy, the above groups are independently optionally further substituted with one or more substituents selected from the group consisting of deuterium, fluoro, chloro, bromo, hydroxy, cyano, methyl, ethyl, propyl, isopropyl, cyclopropyl, cyclobutyl and cyclopentyl;

$R_{5a}$ is hydrogen;

$R_{5e}$ is selected from the group consisting of hydrogen, deuterium, fluoro, chloro, bromo, cyano, methyl, ethyl, propyl, isopropyl, trifluoromethyl, difluoromethyl, trideuteriomethyl and dideuteriomethyl.

As a more further preferred embodiment, in the compound of formula (I), the stereoisomer or pharmaceutically acceptable salt thereof, $R_{14}$ is selected from the group consisting of hydrogen, deuterium, hydroxy, methyl, ethyl, propyl, isopropyl, trifluoromethyl, difluoromethyl, trideuteriomethyl, dideuteriomethyl, cyclopropyl, cyclobutyl, cyclopentyl, oxacyclobutyl and azacyclobutyl, $R_{15}$ and $R_{16}$ are each independently selected from the group consisting of hydrogen, deuterium, fluoro, chloro, bromo, cyano, methyl, ethyl, propyl, isopropyl, cyclopropyl, cyclobutyl, cyclopentyl, oxacyclobutyl, azacyclobutyl, pyrrolidinyl, piperidinyl, morpholinyl and piperazinyl, or $R_{15}$ and $R_{16}$, together with the carbon atom to which they are directly attached, form a C(O), cyclopropyl, cyclobutyl, cyclopentyl, oxacyclobutyl or azacyclobutyl, the above groups are optionally further substituted with one or more substituents selected from the group consisting of deuterium, fluoro, chloro, bromo, cyano, methyl, ethyl, propyl, isopropyl, trifluoromethyl, difluoromethyl, trideuteriomethyl, dideuteriomethyl, cyclopropyl, cyclobutyl, cyclopentyl, oxacyclobutyl, azacyclobutyl and =O.

As the most preferred embodiment, the compound of formula (I), the stereoisomer or pharmaceutically acceptable salt thereof include, but are not limited to, the following compounds:

-continued
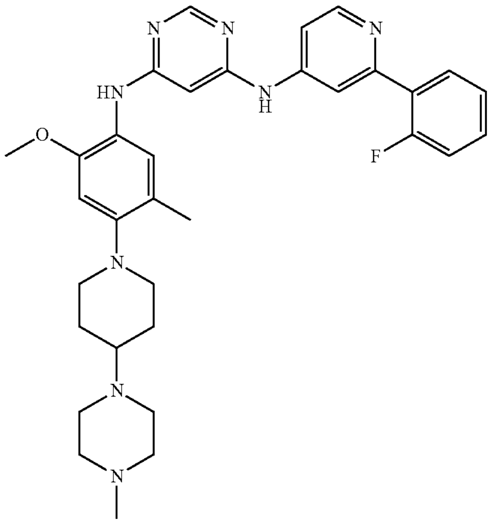
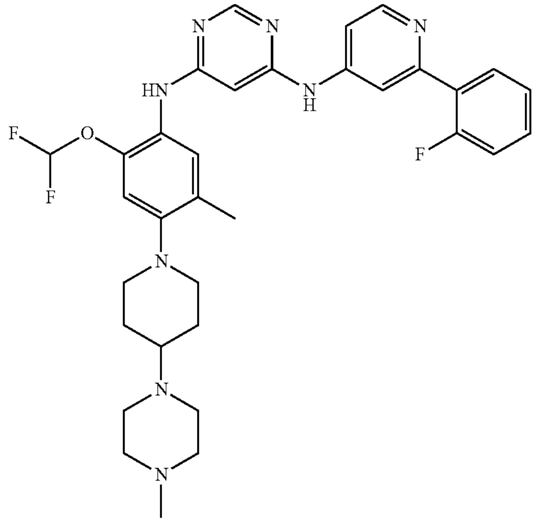
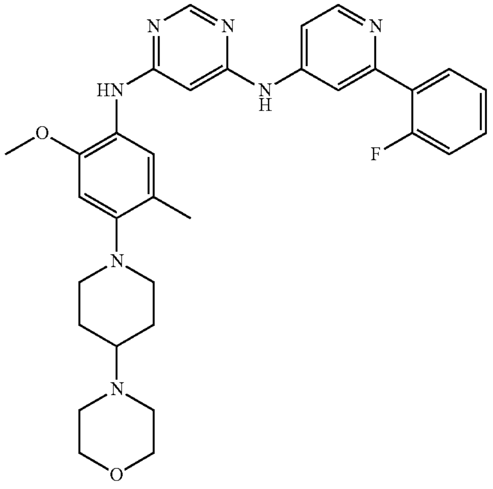
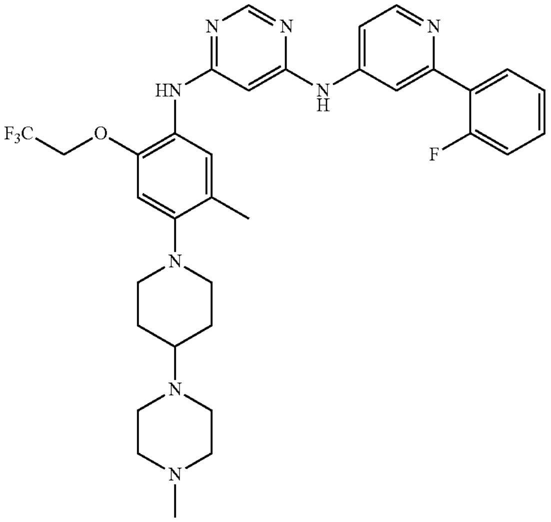
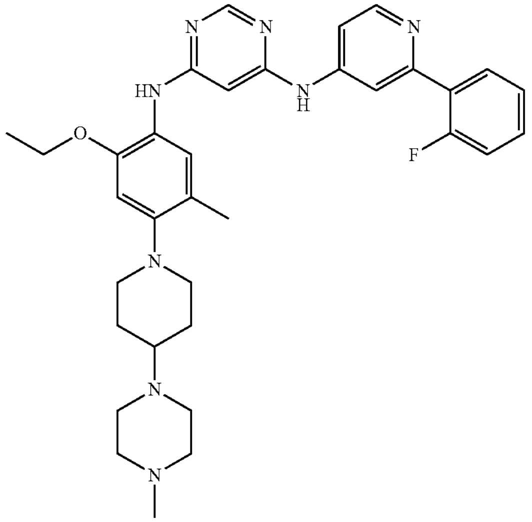
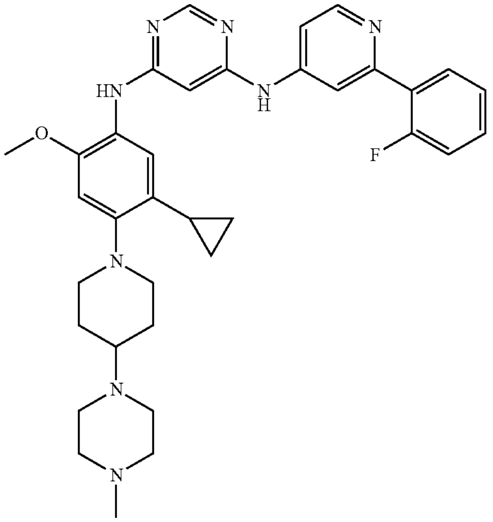

-continued
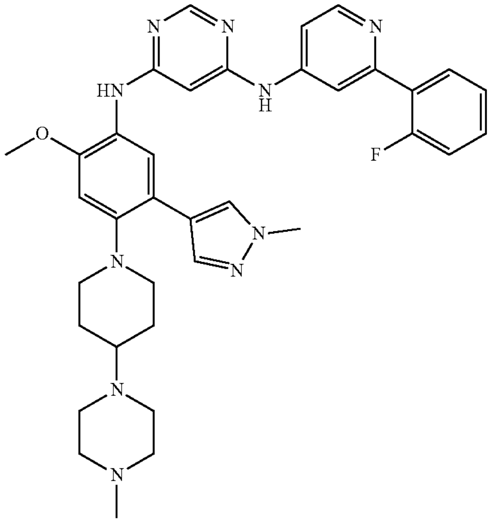
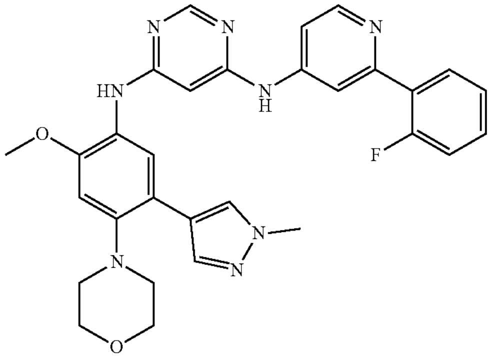
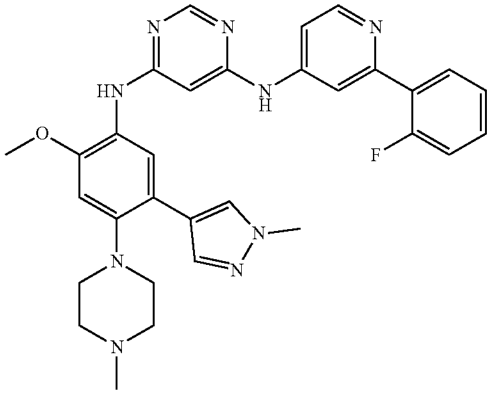
-continued
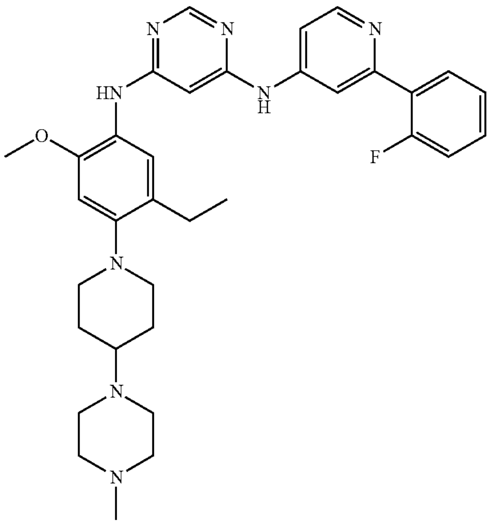
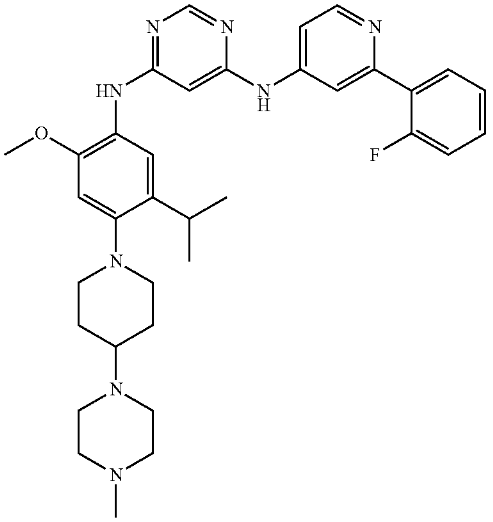
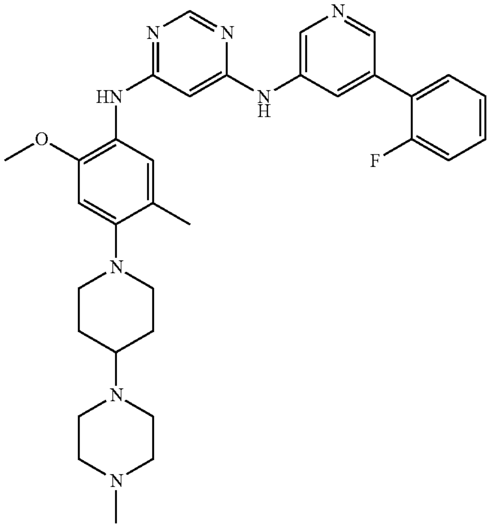

-continued
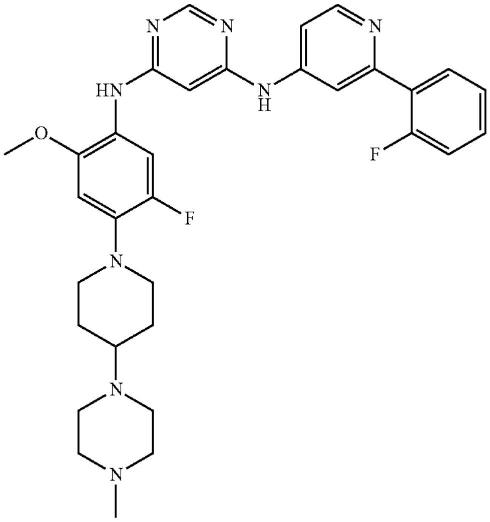
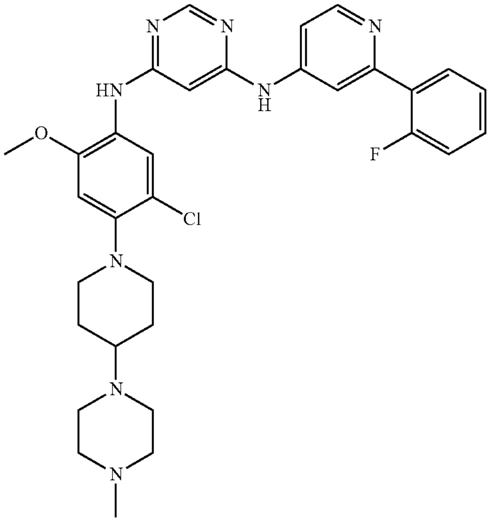
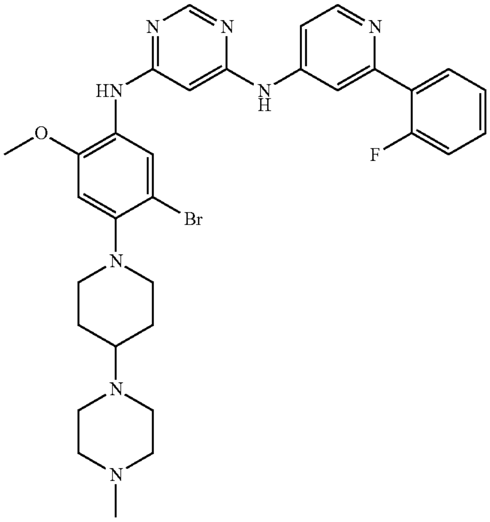
-continued
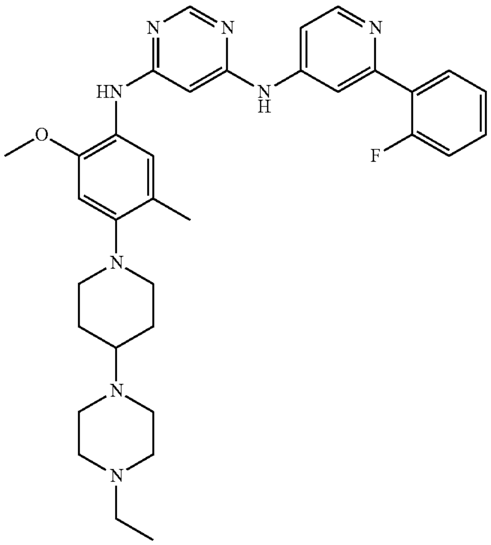
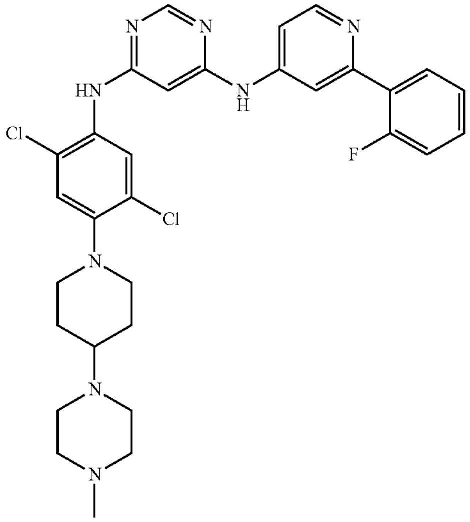
and
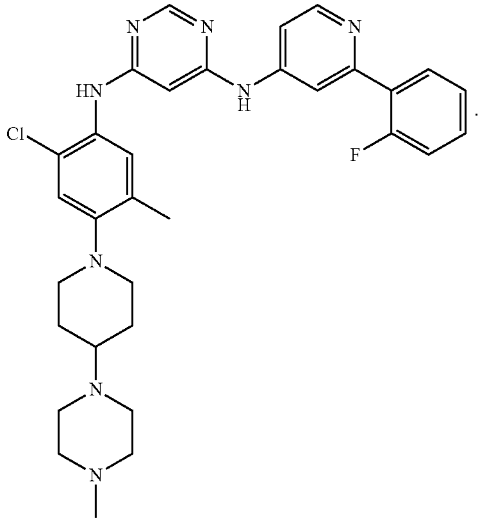
The second aspect of the present invention provides a preparation method for the compound of formula (I), the stereoisomer or pharmaceutically acceptable salt thereof, comprising the following step:

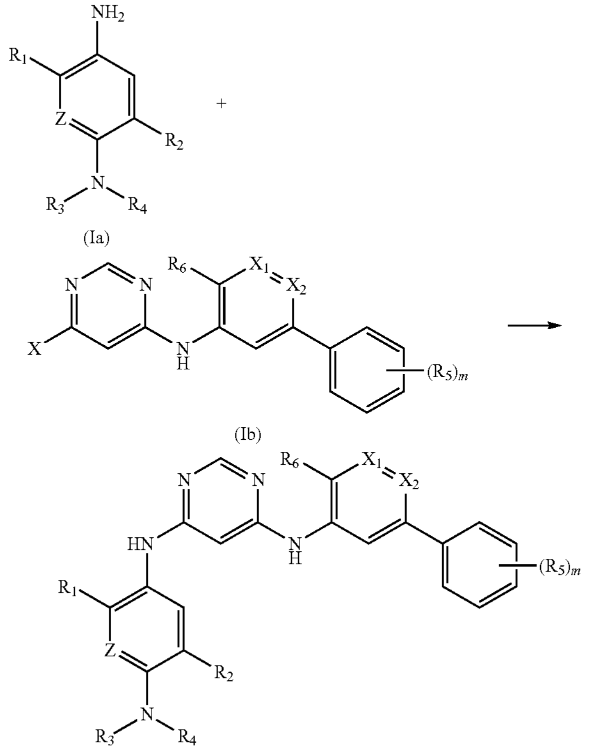

(Ia) (Ib) (I)

wherein, X is chloro or bromo; $X_1$, $X_2$, Z, $R_1$, $R_2$, $R_3$, $R_4$, $R_5$, $R_6$ and m are defined as those in the compound of formula (I).

The third aspect of the present invention provides a pharmaceutical composition, which comprises the compound of formula (I), the stereoisomer or pharmaceutically acceptable salt thereof, and a pharmaceutically acceptable carrier.

The present invention also relates to use of the compound of formula (I), the stereoisomer or pharmaceutically acceptable salt thereof in preparation of a medicament for treating and/or preventing cancer, tumor or metastatic disease at least partially related to EGFR Del19 mutation, EGFR L858R mutation, EGFR L858R/C797S double mutation or EGFR Del19/C797S double mutation.

The present invention also relates to use of the compound of formula (I), the stereoisomer or pharmaceutically acceptable salt thereof in preparation of a medicament for preventing and/or treating tumor, cancer and/or metastatic disease caused by hyperproliferation and dysfunction in cell death induction. The present invention also relates to use of the compound of formula (I), the stereoisomer or pharmaceutically acceptable salt thereof described above in preparation of a medicament for preventing and/or treating lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma at least partially related to EGFR Del19 mutation, EGFR L858R mutation, EGFR L858R/C797S double mutation or EGFR Del19/C797S double mutation.

The present invention also relates to the compound of formula (I), the stereoisomer or pharmaceutically acceptable salt thereof for use as a medicament.

The present invention also relates to the compound of formula (I), the stereoisomer or pharmaceutically acceptable salt thereof for use in the treatment and/or prevention of cancer, tumor or metastatic disease at least partially related to EGFR Del19 mutation, EGFR L858R mutation, EGFR L858R/$C_{797}$S double mutation or EGFR Del19/$C_{797}$S double mutation.

The present invention also relates to the compound of formula (I), the stereoisomer or pharmaceutically acceptable salt thereof for use in the prevention and/or treatment of tumor, cancer and/or metastatic disease caused by hyperproliferation and dysfunction in cell death induction.

The present invention also relates to the compound of formula (I), the stereoisomer or pharmaceutically acceptable salt thereof for use in the treatment and/or prevention of lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma at least partially related to EGFR Del19 mutation, EGFR L858R mutation, EGFR L858R/C797S double mutation or EGFR Del19/C797S double mutation.

The present invention also relates to a method for treating and/or preventing a cancer, tumor or metastatic disease at least partially related to EGFR Del19 mutation, EGFR L858R mutation, EGFR L858R/C797S double mutation or EGFR Del19/C797S double mutation, which comprises administering to a patient in need thereof a therapeutically effective amount of the compound of formula (I), the stereoisomer or pharmaceutically acceptable salt thereof.

The present invention also relates to a method for preventing and/or treating tumor, cancer and/or metastatic disease caused by hyperproliferation and dysfunction in cell death induction, which comprises administering to a patient in need thereof a therapeutically effective amount of the compound of formula (I), the stereoisomer or pharmaceutically acceptable salt thereof.

The present invention also relates to a method for treating and/or preventing lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma at least partially related to EGFR Del19 mutation, EGFR L858R mutation, EGFR L858R/C797S double mutation or EGFR Del19/C797S double mutation, which comprises administering to a patient in need thereof a therapeutically effective amount of the compound of formula (I), the stereoisomer or pharmaceutically acceptable salt thereof.

DETAILED DESCRIPTION OF THE INVENTION

After an extensive and intensive research, the inventors of the present application have developed, for the first time, a pyrimidine-4,6-diamine derivative with a structure shown as formula (I) below. A series of compounds of the present invention can be widely applied to the preparation of medicaments for treating and/or preventing cancer, tumor or metastatic disease at least partially related to EGFR Del19 mutation, EGFR L858R mutation, EGFR L858R/C797S double mutation or EGFR Del19/C797S double mutation, particularly medicaments for treating hyperproliferative disease and disease of dysfunction in cell death induction, so that a new generation of EGFR inhibitors is expected to be developed. The present invention is achieved on this basis.

Detailed description: unless otherwise stated or specified, the following terms used in the specification and claims have the following meanings.

"Alkyl" refers to linear or branched saturated aliphatic alkyl groups, preferably linear alkyl or branched alkyl containing 1 to 10, 1 to 6 or 1 to 4 carbon atoms, including but not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, and the like. "$C_{1-10}$ alkyl" refers to linear alkyl and branched alkyl containing 1 to 10 carbon atoms, "$C_{1-4}$ alkyl" refers to linear alkyl and branched alkyl containing 1 to 4 carbon atoms, "$C_{0-8}$ alkyl" refers to linear alkyl and branched alkyl containing 0 to 8 carbon atoms, and "$C_{0-4}$ alkyl" refers to linear alkyl and branched alkyl containing 0 to 4 carbon atoms.

Alkyl may be optionally substituted or unsubstituted, and w % ben it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, $-C_{0-8}$ alkyl-$SF_5$, $-C_{0-8}$ alkyl-S(O)$_r$$R_8$, $-C_{0-8}$ alkyl-O$-R_9$, $-C_{0-8}$ alkyl-C(O)O$R_9$, $-C_{0-8}$ alkyl-C(O)$R_{10}$, $-C_{0-8}$ alkyl-O$-$C(O)$R_{10}$, $-C_{0-8}$ alkyl-N$R_{11}R_{12}$, $-C_{0-8}$ alkyl-C(=N$R_{11}$)$R_{10}$, $-C_{0-8}$ alkyl-N($R_{11}$)$-$C(=N$R_{12}$)$R_{10}$, $-C_{0-8}$ alkyl-C(O)N$R_{11}R_{12}$ and $-C_{0-8}$ alkyl-N($R_{11}$)$-$C(O)$R_{10}$.

"Cycloalkyl" or "carbocycle" refers to a monocyclic or polycyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated π-electron system; cycloalkyl is classified into monocyclic cycloalkyl and polycyclic cycloalkyl, and is preferably cycloalkyl containing 3 to 12, 3 to 8, or 3 to 6 carbon atoms: for example, "$C_{3-12}$ cycloalkyl" refers to cycloalkyl containing 3 to 12 carbon atoms, "$C_{3-6}$ cycloalkyl" refers to cycloalkyl containing 3 to 6 carbon atoms, "$C_{5-10}$ cycloalkyl" refers to cycloalkyl containing 5 to 10 carbon atoms, and "$C_{5-s}$ cycloalkyl" refers to cycloalkyl containing 5 to 8 carbon atoms, wherein:

monocyclic cycloalkyl includes, but is not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like;

polycyclic cycloalkyl includes spirocycloalkyl, fused cycloalkyl and bridged cycloalkyl. "Spirocycloalkyl" refers to a polycyclic group in which a carbon atom (called a spiro-atom) is shared among monocyclic rings, wherein those rings may contain one or more (preferably, 1, 2 or 3) double bonds, but none of them has a fully conjugated n-electron system. According to the number of the spiro-atoms shared among the rings, the spirocycloalkyl may be monospirocycloalkyl, bispirocycloalkyl or polyspirocycloalkyl, including but not limited to;

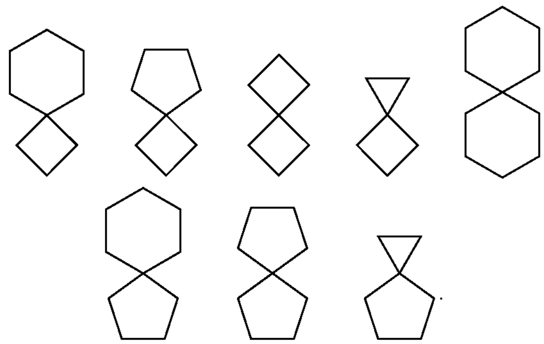

"Fused cycloalkyl" refers to an all-carbon polycyclic group in which each ring shares a pair of adjacent carbon atoms with the other rings in the system, wherein one or more of the rings may contain one or more (preferably, 1, 2 or 3) double bonds, but none of them has a fully conjugated n-electron system. According to the number of formed rings, the fused cycloalkyl may be bicyclic, tricyclic, tetracyclic or polycyclic, including but not limited to:

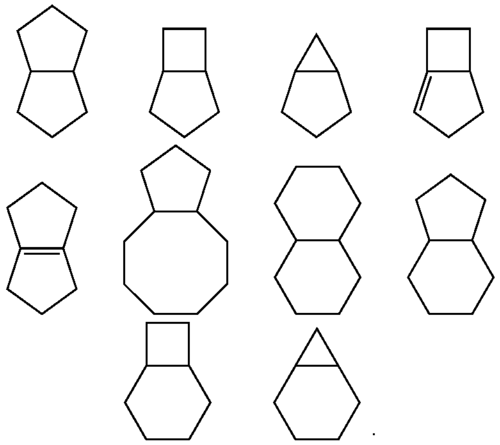

"Bridged cycloalkyl" refers to an all-carbon polycyclic group in which any two rings share two carbon atoms that are not directly connected to each other, wherein these rings may contain one or more (preferably, 1, 2 or 3) double bonds, but none of them has a fully conjugated n-electron system. According to the number of formed rings, the bridged cycloalkyl may be bicyclic, tricyclic, tetracyclic or polycyclic, including but not limited to:

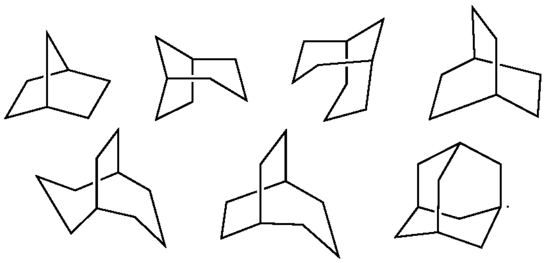

The cycloalkyl ring can be fused to an aryl, heteroaryl or heterocycloalkyl ring, wherein the ring attached to the parent structure is cycloalkyl, which includes, but is not limited to, indanyl, tetrahydronaphthyl, benzocycloheptyl, and the like.

Cycloalkyl may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-N$R_{11}R_{12}$, —$C_{0-8}$ alkyl-C(=N$R_{11}$)$R_{10}$, —$C_{0-8}$ alkyl-N($R_{11}$)—C(=N$R_{12}$)$R_{10}$, —$C_{0-8}$ alkyl-C(O)N$R_{11}R_{12}$ and —$C_{0-8}$ alkyl-N($R_{11}$)—C(O)$R_{10}$.

"Heterocyclyl" or "heterocycle" refers to a monocyclic or polycyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated π-electron system; in heterocyclyl, one or more (preferably 1, 2, 3 or 4) ring atoms are heteroatoms selected from nitrogen, oxygen, S(O)(=NH) and S(O)$_r$ (where r is an integer of 0, 1 or 2), excluding ring moiety of —O—O—, —O—S— or —S—S—, and the remaining ring atoms are carbon atoms. Preferably, heterocyclyl is one containing 3 to 12, 3 to 8, 3 to 6, or 5 to 6 ring atoms: for example, "3-6 membered heterocyclyl" refers to a cyclic group containing 3 to 6 ring atoms, "3-12 membered heterocyclyl" refers to a cyclic group containing 3 to 12 ring atoms, "4-8 membered heterocyclyl" refers to a cyclic group containing 4 to 8 ring atoms, "4-10 membered heterocyclyl" refers to a cyclic group containing 4 to 10 ring atoms, "4-12 membered heterocyclyl" refers to a cyclic group containing 4 to 12 ring atoms, "5-6 membered heterocyclyl" refers to a cyclic group containing 5 to 6 ring atoms, "5-8 membered heterocyclyl" refers to a cyclic group containing 5 to 8 ring atoms, and "5-10 membered heterocyclyl" refers to a cyclic group containing 5 to 10 ring atoms.

Monocyclic heterocyclyl includes, but is not limited to, pyrrolidinyl, piperidinyl, piperazinyl, morpholinyl, thiomorpholinyl, homopiperazinyl, and the like.

Polycyclic heterocyclyl includes spiroheterocyclyl, fused heterocyclyl, and bridged heterocyclyl. "Spiroheterocyclyl" refers to a polycyclic heterocyclyl group in which an atom (called a spiro-atom) is shared among monocyclic rings, wherein one or more (preferably 1, 2, 3 or 4) ring atoms are heteroatoms selected from nitrogen, oxygen, S(O)(=NH) and S(O)$_r$ (wherein r is an integer of 0, 1 or 2), and the remaining ring atoms are carbon atoms. These rings may contain one or more (preferably, 1, 2 or 3) double bonds, but none of them has a fully conjugated n-electron system. According to the number of spiro-atoms shared among the rings, the spiroheterocyclyl may be monospiroheterocyclyl, bispiroheterocyclyl or polyspiroheterocyclyl. Spiroheterocyclyl includes, but is not limited to:

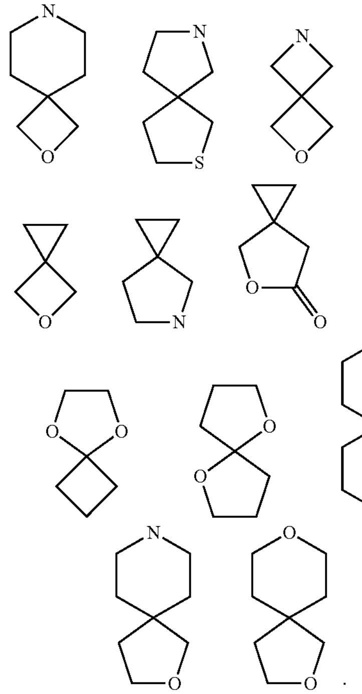

"Fused heterocyclyl" refers to a polycyclic heterocyclyl group in which each ring shares a pair of adjacent atoms with the other rings in the system, wherein one or more (preferably, 1, 2, 3 or 4) of the rings may contain one or more (preferably, 1, 2 or 3) double bonds, but none of them has a fully conjugated π-electron system, wherein one or more (preferably, 1, 2, 3 or 4) ring atoms are heteroatoms selected from nitrogen, oxygen, S(O)(=NH) and S(O)$_r$ (wherein r is an integer of 0, 1 or 2), and the remaining ring atoms are carbon atoms. According to the number of formed rings, the fused heterocyclyl may be bicyclic, tricyclic, tetracyclic or polycyclic, including, but not limited to:

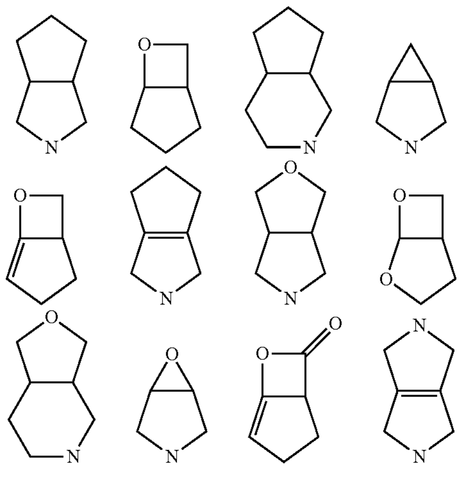

-continued

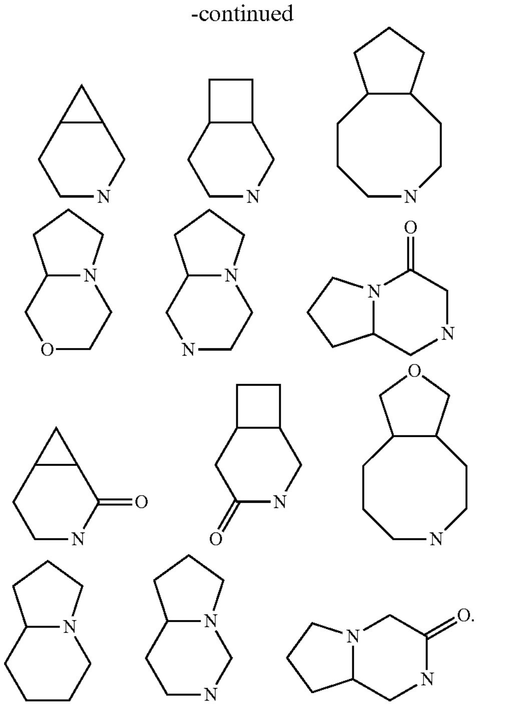

"Bridged heterocyclyl" refers to a polycyclic heterocyclyl group in which any two rings share two carbon atoms that are not directly connected to each other, wherein these rings may contain one or more (preferably, 1, 2 or 3) double bonds, but none of them has a fully conjugated π-electron system, wherein one or more (preferably, 1, 2, 3 or 4) ring atoms are heteroatoms selected from the group consisting of nitrogen, oxygen, S(O)(=NH) and $S(O)_r$ (wherein r is an integer of 0, 1 or 2), and the remaining ring atoms are carbon atoms. According to the number of formed rings, the bridged heterocyclyl may be bicyclic, tricyclic, tetracyclic or polycyclic, including but not limited to:

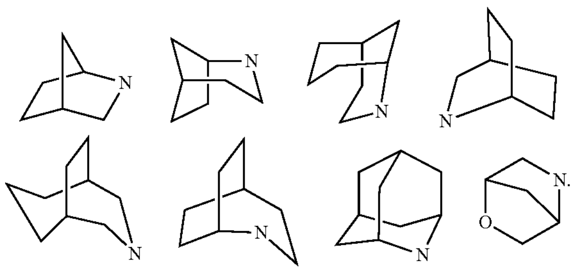

The heterocyclyl ring may be fused to an aryl, heteroaryl or cycloalkyl ring, wherein the ring attached to the parent structure is heterocyclyl, including but not limited to:

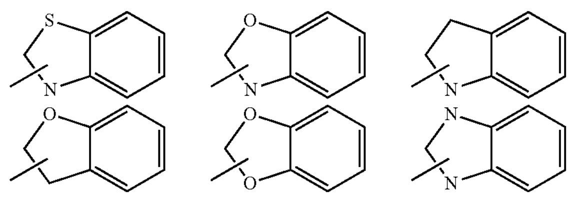

-continued

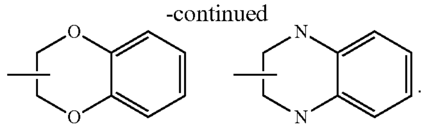

Heterocyclyl may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S$(O)_rR_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"Aryl" or "aromatic ring" refers to an all-carbon monocyclic or fused-polycyclic group (i.e., rings that share a pair of adjacent carbon atoms) and a polycyclic group having a conjugated x-electron system (i.e., rings with adjacent pairs of carbon atoms), and is preferably all-carbon aryl containing 6 to 10, 6 to 8, or 6 carbon atoms. For example, "$C_{6-10}$ aryl" refers to all-carbon aryl containing 6 to 10 carbon atoms, and "$C_{6-8}$ aryl" refers to all-carbon aryl containing 6 to 8 carbon atoms. The aryl or aromatic ring includes, but is not limited to, phenyl and naphthyl. The aryl ring can be fused to a heteroaryl, heterocyclyl or cycloalkyl ring, wherein the ring attached to the parent structure is the aryl ring, including but not limited to:

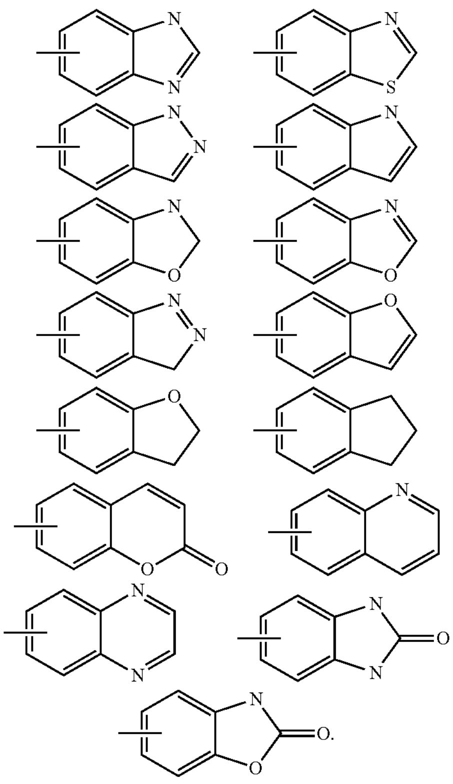

"Aryl" may be substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-N$R_{11}R_{12}$, —$C_{0-8}$ alkyl-C(=N$R_{11}$)$R_{10}$, —$C_{0-8}$ alkyl-N($R_{11}$)—C(=N$R_{12}$)$R_{10}$, —$C_{0-8}$ alkyl-C(O)N$R_{11}R_{12}$ and —$C_{0-8}$ alkyl-N($R_{11}$)—C(O)$R_{10}$.

"Heteroaryl" refers to a heteroaromatic system containing one or more (preferably 1, 2, 3 or 4) heteroatoms including nitrogen, oxygen and $S(O)_r$ (wherein r is an integer of 0, 1 or 2), and is preferably a heteroaromatic system containing 5 to 10, 5 to 8, or 5 to 6 ring atoms. For example, "5-8 membered heteroaryl" refers to a heteroaromatic system containing 5 to 8 ring atoms, and "5-10 membered heteroaryl" refers to a heteroaromatic system containing 5 to 10 ring atoms. The heteroaryl includes, but is not limited to, furyl, thiophenyl, pyridyl, pyrrolyl. N-alkylpyrrolyl, pyrimidinyl, pyrazinyl, imidazolyl, tetrazolyl and the like. The heteroaryl ring can be fused to an aryl, heterocyclyl or cycloalkyl ring, wherein the ring attached to the parent structure is the heteroaryl ring, including but not limited to:

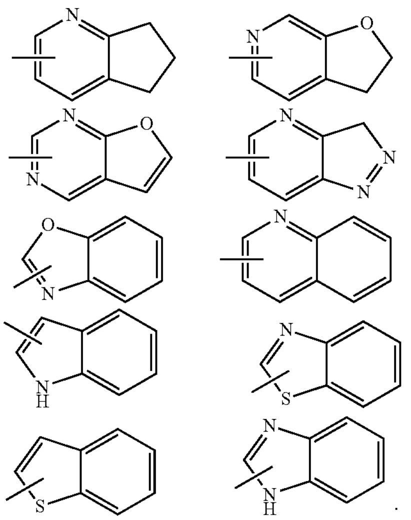

"Heteroaryl" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-N$R_{11}R_{12}$, —$C_{0-8}$ alkyl-C(=N$R_{11}$)$R_{10}$, —$C_{0-8}$ alkyl-N($R_{11}$)—C(=N$R_{12}$)$R_{10}$, —$C_{0-8}$ alkyl-C(O)N$R_{11}R_{12}$ and —$C_{0-8}$ alkyl-N($R_{11}$)—C(O)$R_{10}$.

"Alkenyl" refers to alkyl defined as above consisting of at least two carbon atoms and at least one carbon-carbon double bond, and is preferably linear or branched alkenyl containing 2 to 10 or 2 to 4 carbon atoms. For example, "$C_{2-10}$ alkenyl" refers to linear or branched alkenyl containing 2 to 10 carbon atoms, and "$C_{2-4}$ alkenyl" refers to linear or branched alkenyl containing 2 to 4 carbon atoms. The alkenyl includes, but is not limited to, vinyl, 1-propenyl, 2-propenyl, 1-, 2- or 3-butenyl, and the like.

"Alkenyl" may be substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-N$R_{11}R_{12}$, —$C_{0-8}$ alkyl-C(=N$R_{11}$)$R_{10}$, —$C_{0-8}$ alkyl-N($R_{11}$)—C(=N$R_{12}$)$R_{10}$, —$C_{0-8}$ alkyl-C(O)N$R_{11}R_{12}$ and —$C_{0-8}$ alkyl-N($R_{11}$)—C(O) $R_{10}$.

"Alkynyl" refers to alkyl defined as above consisting of at least two carbon atoms and at least one carbon-carbon triple bond, and is preferably linear or branched alkynyl containing 2 to 10 or 2 to 4 carbon atoms. For example, "$C_{2-10}$ alkynyl" refers to linear or branched alkynyl containing 2 to 10 carbon atoms, and "$C_{2-4}$ alkynyl" refers to linear or branched alkynyl containing 2 to 4 carbon atoms. The alkynyl includes, but is not limited to, ethynyl, 1-propynyl, 2-propynyl, 1-, 2- or 3-butynyl, and the like.

"Alkynyl" may be substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_r$$R_8$, —$C_{0-8}$ alkyl-O—$R_9$, —$C_{0-8}$ alkyl-C(O)O$R_9$, —$C_{0-8}$ alkyl-C(O)$R_{10}$, —$C_{0-8}$ alkyl-O—C(O)$R_{10}$, —$C_{0-8}$ alkyl-N$R_{11}R_{12}$, —$C_{0-8}$ alkyl-C(=N$R_{11}$)$R_{10}$, —$C_{0-8}$ alkyl-N($R_{11}$)—C(=N$R_{12}$)$R_{10}$, —$C_{0-8}$ alkyl-C(O)N$R_{11}R_{12}$ and —$C_{0-8}$ alkyl-N($R_{11}$)—C(O) $R_{10}$.

"Alkoxy" refers to —O-alkyl, wherein the alkyl is defined as above. For example, "$C_{1-10}$ alkoxy" refers to alkoxy containing 1 to 10 carbon atoms, and "$C_{1-4}$ alkoxy" refers to alkoxy containing 1 to 4 carbon atoms. The alkoxy includes, but is not limited to, methoxy, ethoxy, propoxy, butoxy and the like.

"Alkoxy" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_r$$R_8$, —$C_{0-8}$ alkyl-O—$R_9$, —$C_{0-8}$ alkyl-C(O)O$R_9$, —$C_{0-4}$ alkyl-C(O)$R_{10}$, —$C_{0-8}$ alkyl-O—C(O)$R_{10}$, —$C_{0-8}$ alkyl-N$R_{11}R_{12}$, —$C_{0-8}$ alkyl-C(=N$R_{11}$)$R_{10}$. —$C_{0-8}$ alkyl-N($R_{11}$)—C(=N$R_{12}$)$R_{10}$, —$C_{0-8}$ alkyl-C(O)N$R_{11}R_{12}$ and —$C_{0-8}$ alkyl-N($R_{11}$)—C(O)$R_{10}$.

"Cycloalkyloxy" refers to —O-cycloalkyl, wherein the cycloalkyl is defined as above. For example, "$C_{3-12}$ cycloalkyloxy" refers to cycloalkyloxy containing 3 to 12 carbon atoms, and "$C_{3-8}$ cycloalkyloxy" refers to cycloalkyloxy containing 3 to 8 carbon atoms. The cycloalkyloxy includes, but is not limited to, cyclopropyloxy, cyclobutyloxy, cyclopentyloxy, cyclohexyloxy and the like.

"Cycloalkyloxy" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl. $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"Heterocyclyloxy" refers to —O-heterocyclyl, wherein the heterocyclyl is defined as above, and the heterocyclyloxy includes, but is not limited to, azacyclobutyloxy, oxacyclobutyloxy, azacyclopentyloxy, nitrogen, oxacyclohexyloxy and the like.

"Heterocyclyloxy" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_9$, —$C_{0-8}$ alkyl-C(O)$R_{10}$, —$C_{0-8}$ alkyl-O—C(O)$R_{10}$, —$C_{0-8}$ alkyl-$NR_{11}R_{12}$, —$C_{0-8}$ alkyl-C(=$NR_{11}$)$R_{10}$, —$C_{0-8}$ alkyl-N($R_{11}$)—C(=$NR_{12}$)$R_{10}$, —$C_{0-8}$ alkyl-C(O)$NR_{11}R_{12}$ and —$C_{0-8}$ alkyl-N($R_{11}$)—C(O)$R_{10}$.

"$C_{1-10}$ alkanoyl" refers to a monovalent atomic group which is obtained after hydroxy is removed from $C_{1-10}$ alkyl acid, and is also generally referred to as "$C_{0-9}$ alkyl-C(O)—". For example, "$C_1$ alkyl-C(O)—" refers to acetyl; "$C_2$ alkyl-C(O)—" refers to propionyl; and "$C_3$ alkyl-C(O)—" refers to butyryl or isobutyryl.

"$C_{1-4}$" refers to "$C_{1-4}$ alkyl", "$C_{0-4}$" refers to "$C_{0-4}$ alkyl", "$C_{1-8}$" refers to $C_{1-8}$ alkyl, "$C_{0-8}$" refers to $C_{0-8}$ alkyl, and these groups are defined as above.

"—$C_{0-8}$ alkyl-$S(O)_rR_8$" means that the sulfur atom in —$S(O)_rR_8$ is connected to $C_{0-8}$ alkyl, wherein $C_{0-8}$ alkyl is defined as above.

"—$C_{0-8}$ alkyl-O—$R_9$" means that the oxygen atom in —O—$R_9$ is connected to $C_{0-8}$ alkyl, wherein $C_{0-8}$ alkyl is defined as above.

"—$C_{0-8}$ alkyl-C(O)$OR_9$" means that the carbonyl in —C(O)$OR_9$ is connected to $C_{0-8}$ alkyl, wherein $C_{0-8}$ alkyl is defined as above.

"—$C_{0-8}$ alkyl-C(O)$R_{10}$" means that the carbonyl in —C(O)$R_{10}$ is connected to $C_{0-8}$ alkyl, wherein $C_{0-8}$ alkyl is defined as above.

"—$C_{0-8}$ alkyl-O—C(O)$R_{10}$" means that the oxygen atom in —O—C(O)$R_{10}$ is connected to $C_{0-8}$ alkyl, wherein $C_{0-8}$ alkyl is defined as above.

"—$C_{0-8}$ alkyl-$NR_{11}R_{12}$" means that the nitrogen atom in —$NR_{11}R_{12}$ is connected to $C_{0-8}$ alkyl, wherein $C_{0-8}$ alkyl is defined as above.

"—$C_{0-8}$ alkyl-C(=$NR_{11}$)$R_{10}$" means that the carbon atom in —C(=$NR_{11}$)$R_{10}$ is connected to $C_{0-8}$ alkyl, wherein $C_{0-8}$ alkyl is defined as above.

"—$C_{0-8}$ alkyl-N($R_{11}$)—C(=$NR_{12}$)$R_{10}$" means that the nitrogen atom in —N($R_{11}$)—C(=$NR_{12}$)$R_{10}$ is connected to $C_{0-8}$ alkyl, wherein $C_{0-8}$ alkyl is defined as above.

"—$C_{0-8}$ alkyl-C(O)$NR_{11}R_{12}$" means that the carbonyl in —C(O)$NR_{11}R_{12}$ is connected to $C_{0-8}$ alkyl, wherein $C_{0-8}$ alkyl is defined as above.

"—$C_{0-8}$ alkyl-N($R_{11}$)—C(O)$R_{10}$" means that the nitrogen atom in —N($R_{11}$)—C(O)$R_{10}$ is connected to $C_{0-8}$ alkyl, wherein $C_{0-8}$ alkyl is defined as above.

"$C_{1-10}$ haloalkyl" refers to an alkyl group having 1 to 10 carbon atoms in which hydrogens on the alkyl are optionally substituted with a fluorine, chlorine, bromine or iodine atom, including but not limited to, difluoromethyl (—$CHF_2$), dichloromethyl (—$CHCl_2$), dibromomethyl (—$CHBr_2$), trifluoromethyl (—$CF_3$), trichloromethyl (—$CCl_3$), tribromomethyl (—$CBr_3$) and the like.

"$C_{1-10}$ haloalkoxy" refers to an alkoxy group having 1 to 10 carbon atoms in which hydrogens on the alkyl are optionally substituted with a fluorine, chlorine, bromine or iodine atom, including but not limited to, difluoromethoxy, dichloromethoxy, dibromomethoxy, trifluoromethoxy, trichloromethoxy, tribromomethoxy and the like.

"$C_{1-10}$ deuterioalkyl" refers to an alkyl group having 1 to 10 carbon atoms in which hydrogens on the alkyl are optionally substituted with a deuterium atom, including but not limited to, monodeuteriomethyl (—$CH_2D$), dideuteriomethyl (—$CHD_2$), trideuteriomethyl (—CD3) and the like.

"$C_{1-10}$ deuterioalkoxy" refers to an alkyl group having 1 to 10 carbon atoms in which hydrogens on the alkyl are optionally substituted with a deuterium atom, including but not limited to, monodeuteriomethoxy, dideuteriomethoxy, trideuteriomethoxy and the like.

"Halogen" refers to fluorine, chlorine, bromine or iodine. "EtOAc" refers to ethyl acetate. "PE" refers to petroleum ether. "DMF" refers to dimethylformamide. "DMSO" refers to dimethylsulfoxide.

The term "optional" or "optionally" means that the event or circumstance subsequently described may, but not necessarily, occur, and that the description includes instances where the event or circumstance occurs or does not occur, that is, instances where substitution occurs or does not occur. For example, "heterocyclyl group optionally substituted with alkyl" means that alkyl may be, but not necessarily, present, and that the description includes instances where the heterocyclyl group is or is not substituted with alkyl.

The term "substituted" means that one or more "hydrogen atoms" in the group are each independently substituted by a corresponding number of substituents. It goes without saying that a substituent is only in its possible chemical position and consistent with chemical valence bond theory, and those skilled in the art will be able to determine (by studies or theories) possible or impossible substitution without undue efforts. For example, it may be unstable when amino or hydroxy having free hydrogen is bound to a carbon atom having an unsaturated bond (such as olefin).

"Stereoisomers" refer to isomers produced by different spatial arrangements of atoms in molecules, and can be classified into cis-trans isomers and enantiomers, and also into enantiomers and diastereomers. Stereoisomers resulting from rotation of single bonds are referred to as conformational stereo-isomers and sometimes also as rotamers. Stereoisomers resulting from bond lengths, bond angles, intramolecular double bonds, rings and the like are referred to as configuration stereo-isomers, and the configuration stereo-isomers are classified into two categories. Among them, isomers resulting from the fact that a double bond or a single bond of a ring-forming carbon atom cannot rotate freely are referred to as geometric isomers and also as cis-trans isomers, and the isomers are classified into Z, E configurations. For example, cis-2-butene and trans-2-butene are a pair of geometric isomers, and the compounds of the present invention may be understood to comprise the E and/or Z forms if they contain a double bond, as not specifically indicated. Stereoisomers having different optical rotation properties due to the absence of anti-axisymmetry in the molecule are referred to as optical isomers, and are classified into R and S configurations. In the present invention, the term "stereoisomer" is understood to include one or more of the above enantiomers, configuration isomers and conformational isomers, unless otherwise specified.

"Pharmaceutically acceptable salt" as used herein refers to pharmaceutically acceptable acid addition salts or base addition salts, including inorganic and organic acid salts, which may be prepared by methods known in the art.

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The Present Invention is Further Explained in Detail Below with Reference to Examples, which are not Intended to Limit the Present Invention, and the Present Invention is not Merely Limited to the Contents of the Examples The compound structure of the present invention is determined by nuclear magnetic resonance (NMR) and/or liquid chromatography-mass spectrometry (LC-MS).

The NMR chemical shift (δ) is given in parts per million (ppm). The NMR determination is conducted by using a Bruker AVANCE-400/500 nuclear magnetic resonance apparatus, with hexadeuterodimethyl sulfoxide (DMSO-$d_6$), tetradeuteromethanol (MeOH-$d_4$), and deuterated chloroform ($CDCl_3$) as determination solvents, and tetramethylsilane (TMS) as an internal standard.

The LC-MS determination is conducted by using an Agilent 6120 mass spectrometer. The HPLC determination is conducted by using an Agilent 1200 DAD high pressure liquid chromatograph (Sunfire C18 150*4.6 mm chromatographic column) and a Waters 2695-2996 high pressure liquid chromatograph (Gimini C18 150*4.6 mm chromatographic column).

A Yantai Yellow Sea HSGF254 or Qingdao GF254 silica gel plate is adopted as a thin layer chromatography (TLC) silica gel plate. The specification adopted by the TLC is 0.15-0.20 mm, and the specification adopted by the thin layer chromatography for product separation and purification is 0.4-0.5 mm. The Yantai Yellow Sea silica gel of 200-300 mesh is generally utilized as a carrier in column chromatography.

Starting materials in the examples of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

I. Preparation of Intermediates

Intermediate 1: Preparation of 2-methoxy-5-methyl-4-(4-(4-methylpiperazin-1-yl)piperidin-1-yl)aniline

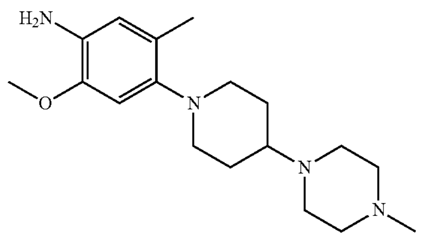

Step 1: Synthesis of 1-(1-(5-methoxy-2-methyl-4-nitrophenyl)piperidin-4-yl)-4-methylpiperazine

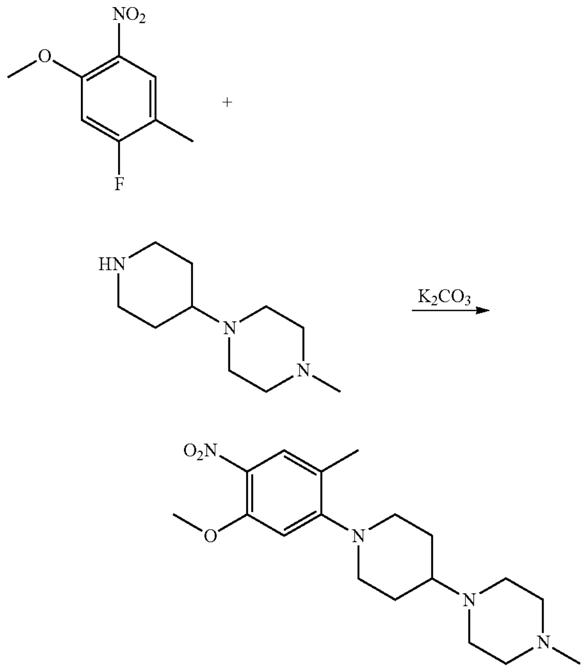

1-fluoro-5-methoxy-2-methyl-4-nitrobenzene (1.2 g, 6.48 mmol), 1-methyl-4-(piperidin-4-yl)piperazine (1.43 g, 7.77 mmol) and $K_2CO_3$ (1.79 g, 12.96 mmol) were added in DMSO (25 mL), and then under nitrogen protection, the mixture was stirred at 80° C. overnight. The reaction mixture was diluted with water and then extracted with ethyl acetate. The organic phase was washed with saturated brine, dried over anhydrous sodium sulfate, filtered and concentrated. The residue was separated by the column chromatography to obtain 1-(1-(5-methoxy-2-methyl-4-nitrophenyl)piperidin-4-yl)-4-methylpiperazine (2.15 g, yield: 95.2%). MS m/z (EST): 349.2 $[M+H]^+$.

Step 2: Synthesis of 2-methoxy-5-methyl-4-(4-(4-methylpiperazin-1-yl)piperidin-1-yl)aniline

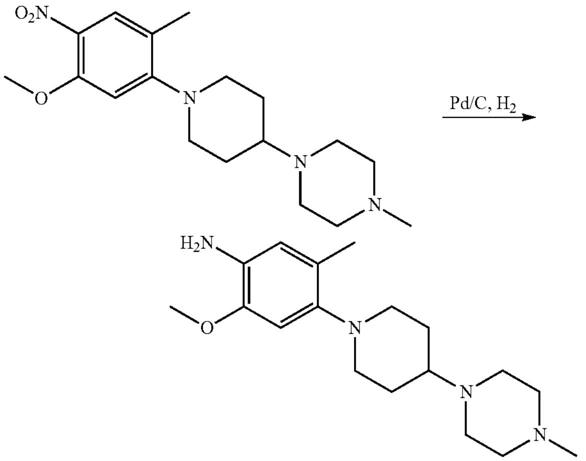

1-(1-(5-methoxy-2-methyl-4-nitrophenyl)piperidin-4-yl)-4-methylpiperazine (1 g, 2.87 mmol) and Pd/C (50 mg, 10%) were added in methanol (30 mL). Hydrogen was charged to replace, and then the mixture was stirred at room temperature under an atmospheric hydrogen atmosphere for 1 hr. After the reaction was completed, the reaction mixture was filtered. The filtrate was concentrated, and then the residue was separated by the column chromatography to obtain 2-methoxy-5-methyl-4-(4-(4-methylpiperazin-1-yl) piperidin-1-yl)aniline (900 mg, yield: 98.5%). MS m/z (ESI): 319.2 $[M+H]^+$.

Intermediate 2: Preparation of 2-methoxy-5-methyl-4-(4-morpholinopiperidin-1-yl)aniline

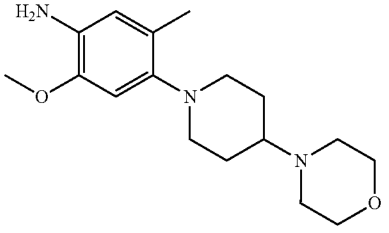

Step 1: Synthesis of 4-(1-(5-methoxy-2-methyl-4-nitrophenyl)piperidin-4-yl)morpholine

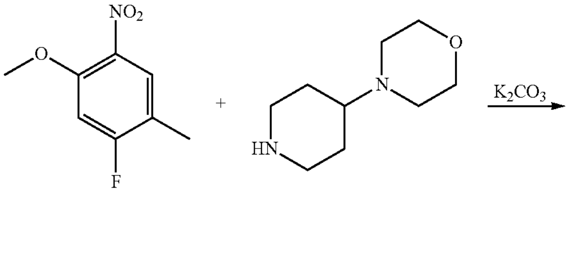

-continued

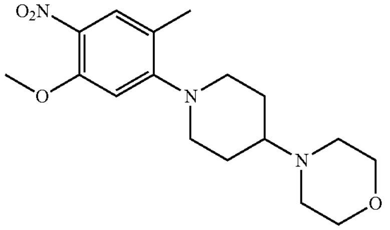 [SMILES: COc1cc(N2CCC(N3CCOCC3)CC2)c(C)cc1N]

1-fluoro-5-methoxy-2-methyl-4-nitrobenzene (0.73 g, 3.94 mmol) was added to DMSO (20 mL), and then $K_2CO_3$ (1.09 g, 7.89 mmol) and 4-(piperidin-4-yl)morpholine (0.81 g, 4.73 mmol) were added. The mixture was reacted at 80° C. overnight and then heated to 110° C. for reaction for 5 hrs. The reaction mixture was cooled to room temperature and then extracted with dichloromethane and water. The organic phase was washed with saturated brine, dried over anhydrous sodium sulfate, filtered and concentrated. The residue was separated by the column chromatography [developing solvent: $CH_2Cl_2$/MeOH (+1% aqua ammonia)=0-10%] to obtain 4-(1-(5-methoxy-2-methyl-4-nitrophenyl)piperidin-4-yl)morpholine (1.23 g, yield: 80.9%). MS m/z (ESI): 336.0 $[M+H]^+$.

Step 2: Synthesis of 2-methoxy-5-methyl-4-(4-morpholinopiperidin-1-yl)aniline

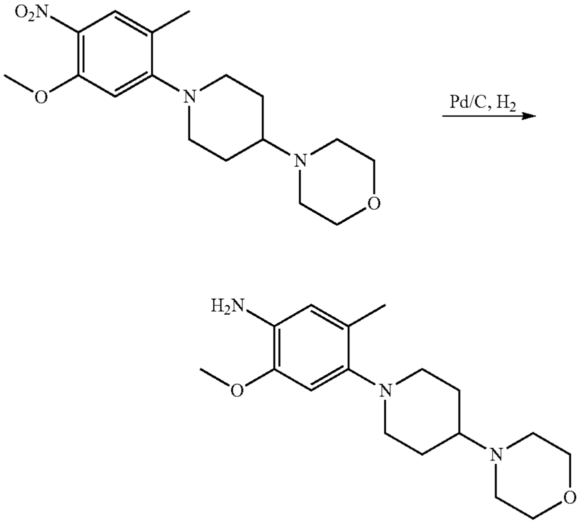 [SMILES: COc1cc(N2CCC(N3CCOCC3)CC2)c(C)cc1[N+](=O)[O-] ; "Pd/C, H2" ; COc1cc(N2CCC(N3CCOCC3)CC2)c(C)cc1N]

4-(1-(5-methoxy-2-methyl-4-nitrophenyl)piperidin-4-yl) morpholine (1.23 g, 3.18 mmol) was dissolved in methanol (10 mL) and then Pd/C (0.10 g, 10%) was added. Hydrogen was charged to replace three times, and the mixture was reacted at room temperature under an atmospheric hydrogen atmosphere overnight. The reaction mixture was filtered through diatomaceous earth, and the filtrate was concentrated. The residue was then separated by the column chromatography [developing solvent: $CH_2Cl_2$/MeOH (+1% aqua ammonia)=O—10%] to obtain 2-methoxy-5-methyl-4-(4-morpholinopiperidin-1-yl)aniline (0.81 g, yield: 80.2%). MS m/z (ESI): 306.2 $[M+H]^+$.

Intermediate 3: Preparation of 2-ethoxy-5-methyl-4-(4-(4-methylpiperazin-1-yl)piperidin-1-yl)aniline

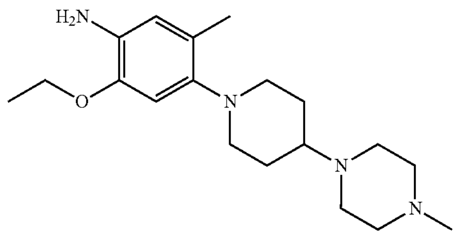 [SMILES: CCOc1cc(N2CCC(N3CCN(C)CC3)CC2)c(C)cc1N]

Step 1: Synthesis of 1-ethoxy-5-fluoro-4-methyl-2-nitrobenzene

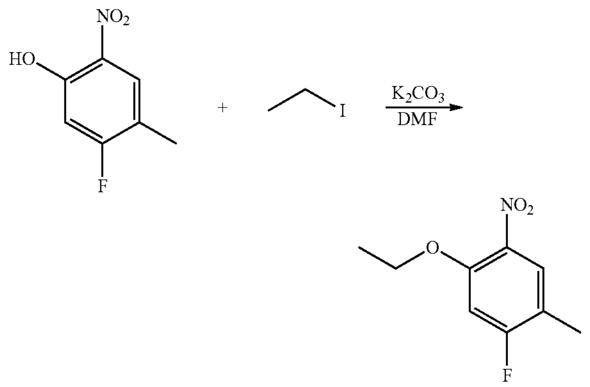

5-fluoro-4-methyl-2-nitrophenol (400 mg, 2.34 mmol) was dissolved in DMF (10 mL), and then $K_2CO_3$ (969.16 mg, 7.01 mmol) and iodoethane (0.37 mL, 4.68 mmol) were added. The mixture was stirred overnight. After the reaction was completed, the reaction mixture was diluted with water and extracted with ethyl acetate. The organic phase was washed with saturated brine, dried over anhydrous sodium sulfate, filtered and concentrated to obtain 1-ethoxy-5-fluoro-4-methyl-2-nitrobenzene (420 mg, yield: 90.2%). MS m/z (ESI): 200 $[M+H]^+$.

Step 2: Synthesis of 1-(1-(5-ethoxy-2-methyl-4-nitrophenyl)piperidin-4-yl)-4-methylpiperazine

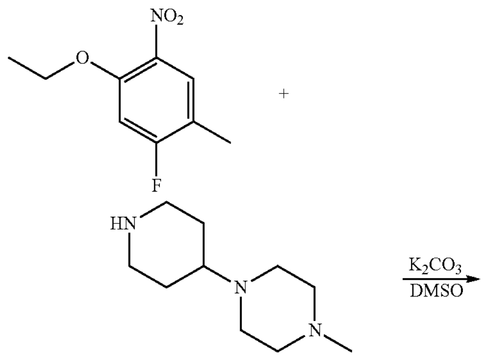

-continued

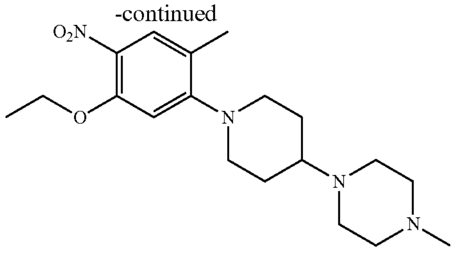

1-ethoxy-5-fluoro-4-methyl-2-nitrobenzene (420 mg, 2.11 mmol) was dissolved in DMSO (10 mL), and then $K_2CO_3$ (582 mg, 4.22 mmol) and 1-methyl-4-(piperidin-4-yl)piperazine (580 mg, 3.16 mmol) were added. The mixture was stirred at 90° C. overnight. After the reaction was completed, the reaction mixture was diluted with water and extracted with dichloromethane. The organic phase was washed with saturated brine, dried over anhydrous sodium sulfate and filtered. The filtrate was concentrated to obtain 1-(1-(5-ethoxy-2-methyl-4-nitrophenyl)piperidin-4-yl)-4-methylpiperazine (700 mg, yield: 91.6%). MS m/z (ESI): 363 $[M+H]^+$.

Step 3: Synthesis of 2-ethoxy-5-methyl-4-(4-(4-methylpiperazin-1-yl)piperidin-1-yl)aniline

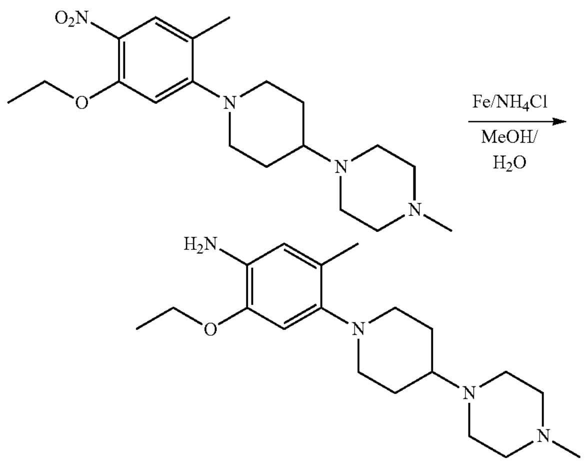

1-(1-(5-ethoxy-2-methyl-4-nitrophenyl)piperidin-4-yl)-4-methylpiperazine (700 mg, 1.93 mmol) was dissolved in methanol (20 mL) and water (5 mL) and then $NH_4Cl$ (1.03 g, 19.31 mmol) and Fe powder (1.08 g, 19.31 mmol) were added. The mixture was stirred at 85° C. for 2 hrs. After the reaction was completed, the reaction mixture was filtered, and the filtrate was concentrated. The residue was separated by the column chromatography to obtain 2-ethoxy-5-methyl-4-(4-(4-methylpiperazin-1-yl)piperidin-1-yl)aniline (610 mg, yield: 95%). MS m/z (ESI): 333.2 $[M+H]^+$.

Intermediate 4: Preparation of 2-(difluoromethoxy)-5-methyl-4-(4-(4-methylpiperazin-1-yl)piperidin-1-yl)aniline

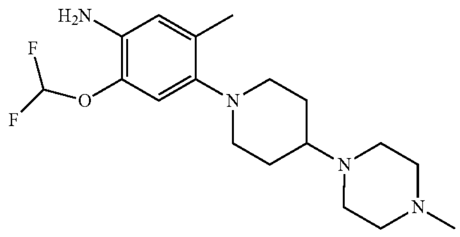 [SMILES: Cc1cc(N)c(OC(F)F)cc1N1CCC(N2CCN(C)CC2)CC1]

Step 1: Synthesis of 1-(difluoromethoxy)-5-fluoro-4-methyl-2-nitrobenzene

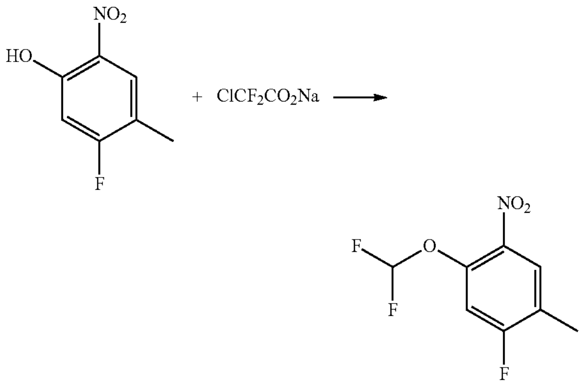

5-fluoro-4-methyl-2-nitrophenol (400 mg, 2.34 mmol) was dissolved in DMF (10 mL), and $Na_2CO_3$ (743 mg, 7.01 mmol) was added. The reaction mixture was heated to 90° C. and then $ClCF_2CO_2Na$ (1247 mg, 8.18 mmol) was added. The mixture was stirred at 90° C. for 3 hrs. After the reaction was completed, the reaction mixture was cooled to room temperature, diluted with water and extracted with ethyl acetate. The organic phase was washed with saturated brine, dried over anhydrous sodium sulfate and filtered. The filtrate was concentrated to obtain 1-(difluoromethoxy)-5-fluoro-4-methyl-2-nitrobenzene (480 mg, yield: 92.9%). MS m/z (ESI): 222.0 [M+H]$^+$.

Step 2: Synthesis of 1-(1-(5-(difluoromethoxy)-2-methyl-4-nitrophenyl)piperidin-4-yl)-4-methylpiperazine

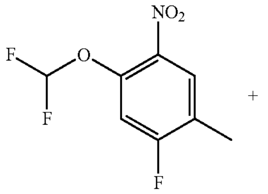

-continued

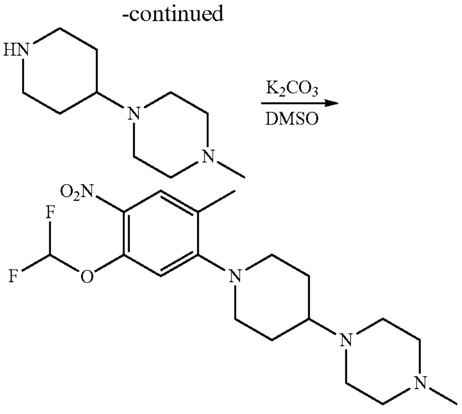

1-(difluoromethoxy)-5-fluoro-4-methyl-2-nitrobenzene (480 mg, 2.17 mmol) was dissolved in DMSO (10 mL), and then $K_2CO_3$ (750 mg, 5.43 mmol) and 1-methyl-4-(piperidin-4-yl)piperazine (597 mg, 3.26 mmol) were added. The mixture was stirred at 90° C. overnight. After the reaction was completed, the reaction mixture was diluted with water and extracted with dichloromethane. The organic phase was washed with saturated brine, dried over anhydrous sodium sulfate and filtered. The filtrate was concentrated to obtain 1-(1-(5-(difluoromethoxy)-2-methyl-4-nitrophenyl)piperidin-4-yl)-4-methylpiperazine (760 mg, yield: 91.1%). MS m/z (ESI): 385.0 [M+H]$^+$.

Step 3: Synthesis of 2-(difluoromethoxy)-5-methyl-4-(4-(4-methylpiperazin-1-yl)piperidin-1-yl)aniline

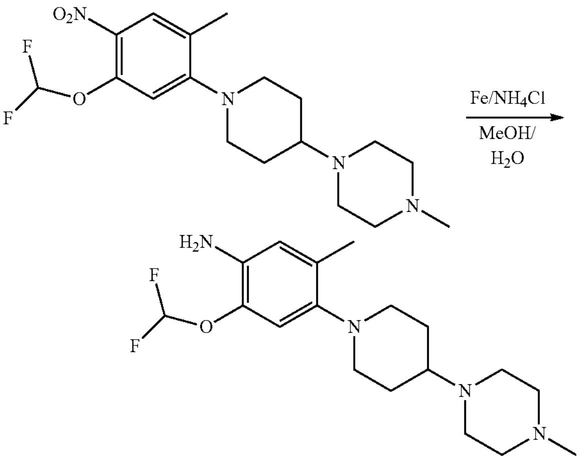

1-(1-(5-(difluoromethoxy)-2-methyl-4-nitrophenyl)piperidin-4-yl)-4-methylpiperazine (760 mg, 1.98 mmol) was dissolved in methanol (20 mL) and water (5 mL) and then $NH_4Cl$ (1057 mg, 19.77 mmol) and Fe powder (1104 mg, 19.77 mmol) were added. The mixture was stirred at 85° C. for 2 hrs. After the reaction was completed, the reaction mixture was filtered. The filtrate was concentrated, and then the residue was separated by the column chromatography to obtain 2-(difluoromethoxy)-5-methyl-4-(4-(4-methylpiperazin-1-yl)piperidin-1-yl)aniline (310 mg, yield: 44.2%). MS m/z (ESI): 355.0 [M+H]$^+$.

Intermediate 5: Preparation of 5-methyl-4-(4-(4-methylpiperazin-1-yl)piperidin-1-yl)-2-(2,2,2-trifluoroethoxy)aniline

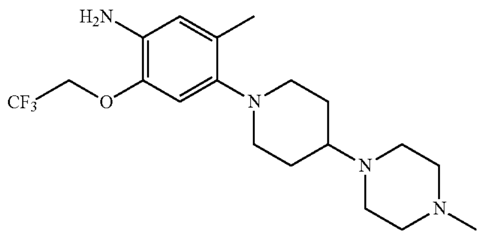 [SMILES: Cc1cc(N)c(OCC(F)(F)F)cc1N1CCC(N2CCN(C)CC2)CC1]

Step 1: Synthesis of 1-fluoro-2-methyl-4-nitro-5-(2,2,2-trifluoroethoxy)benzene

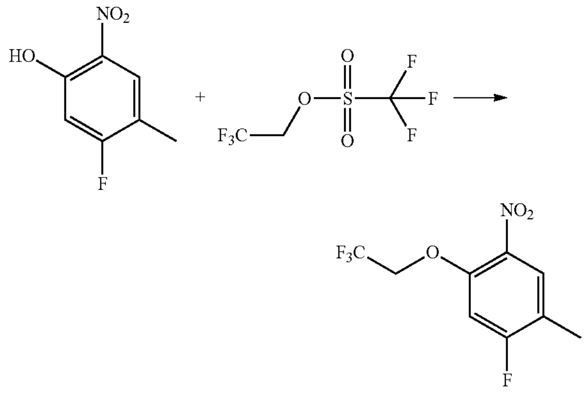

5-fluoro-4-methyl-2-nitrophenol (400 mg, 2.34 mmol) was dissolved in DMF (15 mL) and then $K_2CO_3$ (969 mg, 7.01 mmol) and 2,2,2-trifluoroethyl trifluoromethanesulfonate (0.67 mL, 4.68 mmol) were added. The mixture was stirred at room temperature overnight. After the reaction was completed, the reaction mixture was diluted with water and extracted with ethyl acetate. The organic phase was washed with saturated brine, dried over anhydrous sodium sulfate and filtered. The filtrate was concentrated to obtain 1-fluoro-2-methyl-4-nitro-5-(2,2,2-trifluoroethoxy)benzene (560 mg, yield: 94.6%). MS m/z (ESI): 254.0 $[M+H]^+$.

Step 2: Synthesis of 1-methyl-4-(1-(2-methyl-4-nitro-5-(2,2,2-trifluoroethoxy)phenyl)piperidin-4-yl)piperazine

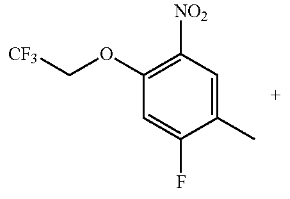

-continued

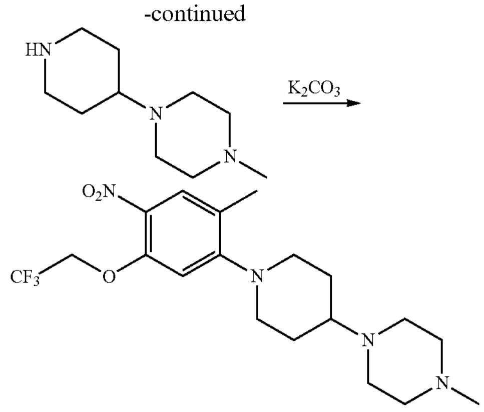

1-fluoro-2-methyl-4-nitro-5-(2,2,2-trifluoroethoxy)benzene (580 mg, 2.29 mmol) was dissolved in DMSO (15 mL) and then $K_2CO_3$ (792 mg, 5.73 mmol) and 1-methyl-4-(piperidin-4-yl)piperazine (630 mg, 3.44 mmol) were added. Then the mixture was stirred at 90° C. for 6 hrs. After the reaction was completed, the reaction mixture was diluted with water and extracted with dichloromethane. The organic phase was washed with saturated brine, dried over anhydrous sodium sulfate and filtered. The filtrate was concentrated to obtain 1-methyl-4-(1-(2-methyl-4-nitro-5-(2,2,2-trifluoroethoxy)phenyl)piperidin-4-yl)piperazine (900 mg, yield: 94.3%). MS m/z (ESI): 417.0 $[M+H]^+$.

Step 3: Synthesis of 5-methyl-4-(4-(4-methylpiperazin-1-yl)piperidin-1-yl)-2-(2,2,2-trifluoroethoxy)aniline

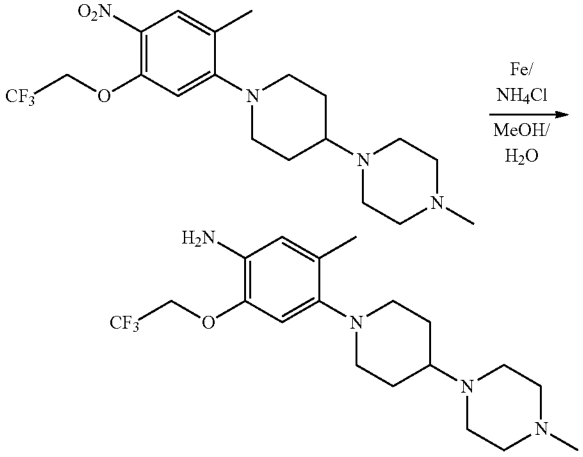

1-methyl-4-(1-(2-methyl-4-nitro-5-(2,2,2-trifluoroethoxy)phenyl)piperidin-4-yl)piperazine (900 mg, 2.16 mmol) was dissolved in methanol (20 mL) and then water (5 mL) and then $NH_4Cl$ (1156 mg, 21.61 mmol) and Fe powder (1207 mg, 21.61 mmol) were added. The mixture was stirred at 85° C. for 2 hrs. After the reaction was completed, the reaction mixture was filtered, and the filtrate was concentrated. The residue was separated by the column chromatography to obtain 5-methyl-4-(4-(4-methylpiperazin-1-yl)piperidin-1-yl)-2-(2,2,2-trifluoroethoxy)aniline (780 mg, yield: 93.4%). MS m/z (ESI): 387.0 $[M+H]^+$.

Intermediate 6: Preparation of 5-ethyl-2-methoxy-4-(4-(4-methylpiperazin-1-yl)piperidin-1-yl)aniline

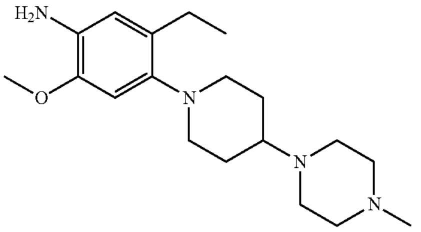

Step 1: Synthesis of 1(1-(2-bromo-5-methoxy-4-nitrophenyl)piperidin-4-yl)-4-methylpiperazine

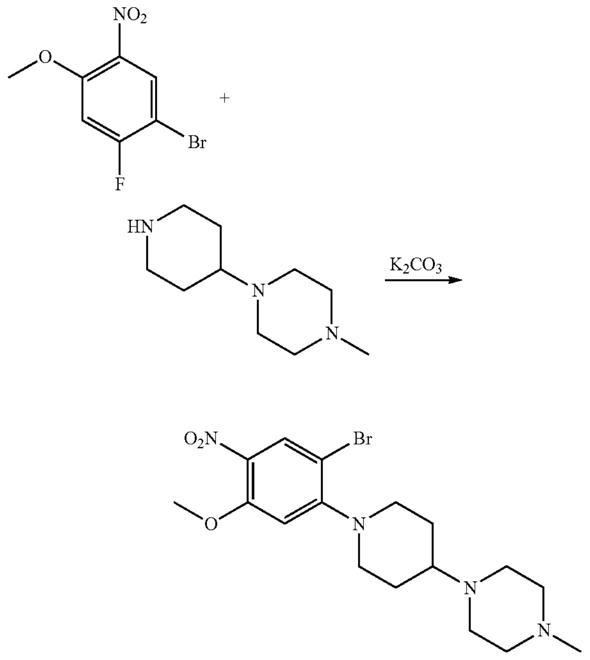

1-bromo-2-fluoro-4-methoxy-5-nitrobenzene (1.40 g, 5.60 mmol) was dissolved in dimethylamine (10.0 mL) and then $K_2CO_3$ (1.55 g, 11.20 mmol) and 1-methyl-4-(piperidin-4-yl)piperazine (1.54 g, 8.40 mmol) were added. Under nitrogen protection, the mixture was heated to 100° C. for reaction for 2 hrs. The reaction mixture was cooled to room temperature and then extracted with dichloromethane and water. The organic phase was washed with saturated brine, dried over anhydrous sodium sulfate, filtered and concentrated. The residue was separated by the column chromatography to obtain 1-(1-(2-bromo-5-methoxy-4-nitrophenyl) piperidin-4-yl)-4-methylpiperazine (2.20 g, yield: 92.9%). MS m/z (ESI): 413.0, 415.0 $[M+H]^+$.

Step 2: Synthesis of 1-(1-(5-methoxy-4-nitro-2-vinylphenyl)piperidin-4-yl)-4-methylpiperazine

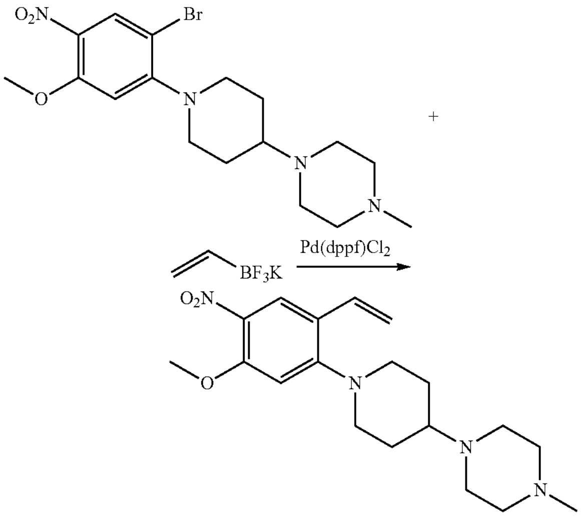

1-(1-(2-bromo-5-methoxy-4-nitrophenyl)piperidin-4-yl)-4-methylpiperazine (400 mg, 0.97 mmol) was dissolved in 1,4-dioxane (16 mL) and water (4 mL) and then potassium vinyltrifluoroborate (259 mg, 1.94 mmol), $Na_2CO_3$ (308 mg, 2.90 mmol) and $Pd(dppf)Cl_2$ (70.8 mg, 0.10 mmol) were added. Under nitrogen protection, the mixture was stirred at 90° C. for 2 hrs. After the reaction was completed, the reaction mixture was concentrated, and the residue was separated by the column chromatography to obtain 1-(1-(5-methoxy-4-nitro-2-vinylphenyl)piperidin-4-yl)-4-methylpiperazine (300 mg, yield: 86.0%). MS m/z (ESI): 361.0 $[M+H]^+$.

Step 3: Synthesis of 5-ethyl-2-methoxy-4-(4-(4-methylpiperazin-1-yl)piperidin-1-yl)aniline

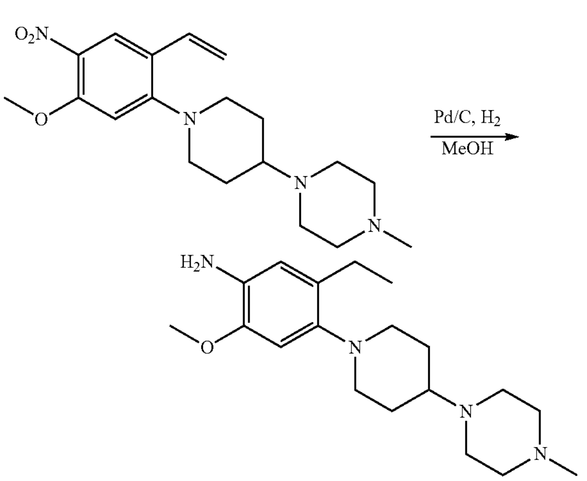

1-(1-(5-methoxy-4-nitro-2-vinylphenyl)piperidin-4-yl)-4-methylpiperazine (300 mg, 0.83 mmol) was dissolved in methanol (20 mL) and then Pd/C (30 mg, 10%) was added. The mixture was stirred at room temperature under an atmospheric hydrogen atmosphere for 2 hrs. After the reaction was completed, the reaction mixture was filtered. The filtrate was concentrated, and the residue was separated by the column chromatography to obtain 5-ethyl-2-methoxy-4-(4-(4-methylpiperazin-1-yl)piperidin-1-yl)aniline (200 mg, yield: 72.3%). MS m/z (ESI): 333.2 $[M+H]^+$.

Intermediate 7: Preparation of 5-isopropyl-2-methoxy-4-(4-(4-methylpiperazin-1-yl)piperidin-1-yl)aniline

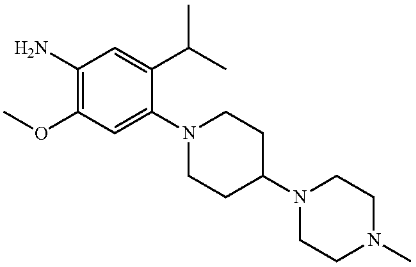

Step 1: Synthesis of 1-(1-(5-methoxy-4-nitro-2-(prop-1-en-2-yl)phenyl)piperidin-4-yl)-4-methylpiperazine

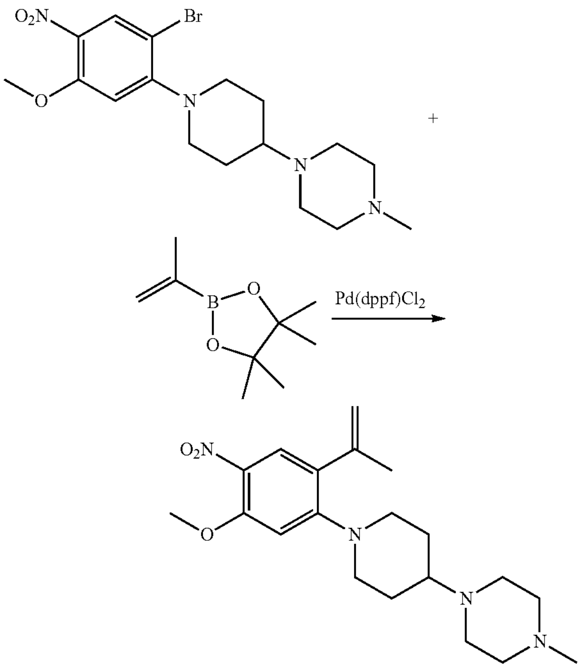

1-(1-(2-bromo-5-methoxy-4-nitrophenyl)piperidin-4-yl)-4-methylpiperazine (0.40 g, 0.95 mmol) was added in 1,4-dioxane (10 mL) and water (3 mL) and then $Na_2CO_3$ (0.30 g, 2.83 mmol), $Pd(dppf)Cl_2$ (0.03 g, 0.05 mmol) and 4,4,5,5-tetramethyl-2-(prop-1-en-2-yl)-1,3,2-dioxaborolane (0.20 mL, 1.04 mmol) were added. Under nitrogen protection, the mixture was heated to 90° C. for reaction overnight. The reaction mixture was cooled to room temperature and then extracted with ethyl acetate and water. The organic phase was then washed with saturated brine, dried over sodium sulfate, filtered and concentrated. The residue was separated by the column chromatography to obtain 1-(1-(5-methoxy-4-nitro-2-(prop-1-en-2-yl)phenyl)piperidin-4-yl)-4-methylpiperazine (0.26 g, yield: 61.0%). MS m/z (ESI): 375.2 $[M+H]^+$.

Step 2: Synthesis of 5-isopropyl-2-methoxy-4-(4-(4-methylpiperazin-1-yl)piperidin-1-yl)aniline

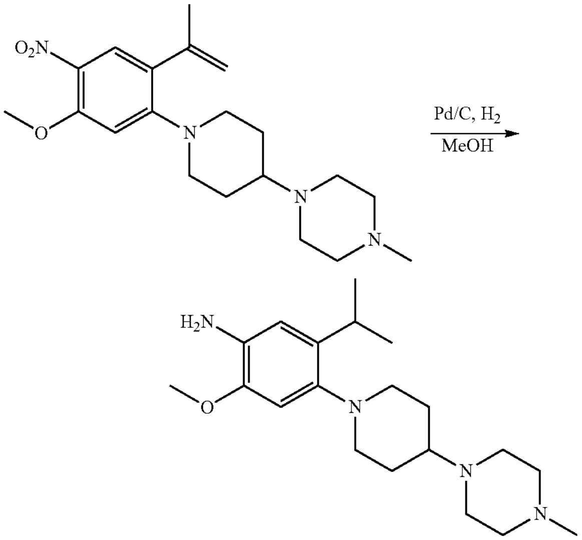

1-(1-(5-methoxy-4-nitro-2-(prop-1-en-2-yl)phenyl)piperidin-4-yl)-4-methylpiperazine (0.26 g, 0.57 mmol) was dissolved in methanol (10 mL) and then Pd/C (0.05 g, 10%) was added. The mixture was reacted at room temperature under an atmospheric hydrogen atmosphere for 3 hrs. The reaction mixture was filtered through diatomaceous earth, and the filtrate was concentrated. The residue was then separated by the column chromatography [developing solvent: $CH_2Cl_2$/MeOH (+1% aqua ammonia)=0-10%)] to obtain 5-isopropyl-2-methoxy-4-(4-(4-methylpiperazin-1-yl)piperidin-1-yl)aniline (0.14 g, yield: 67.7%). MS m/z (ESI): 347.2 $[M+H]^+$.

Intermediate 8: Preparation of 5-cyclopropyl-2-methoxy-4-(4-(4-methylpiperazin-1-yl)piperidin-1-yl)aniline

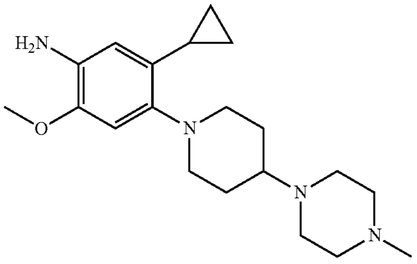

Step 1: Synthesis of 1-(1-(2-cyclopropyl-5-methoxy-4-nitrophenyl)piperidin-4-yl)-4-methylpiperazine

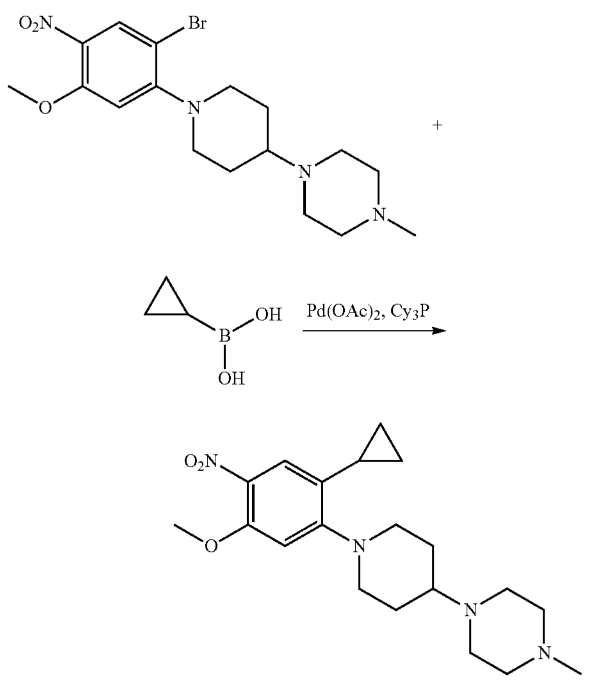

To a solution of 1-(1-(2-bromo-5-methoxy-4-nitrophenyl)piperidin-4-yl)-4-methylpiperazine (0.40 g, 0.95 mmol) in toluene (10 mL), $K_3PO_4$ (0.60 g, 2.83 mmol), tricyclohexylphosphine (0.079 g, 0.28 mmol), $Pd(OAc)_2$ (0.03 g, 0.14 mmol) and cyclopropylboronic acid (0.24 g, 2.83 mmol) were added, and then under nitrogen protection, the mixture was heated to 120° C. for reaction overnight. The reaction mixture was cooled to room temperature and then extracted with ethyl acetate and water. The organic phase was then washed with saturated brine, dried over anhydrous sodium sulfate and filtered. The filtrate was concentrated, and the residue was separated by the column chromatography to obtain 1-(1-(2-cyclopropyl-5-methoxy-4-nitrophenyl)piperidin-4-yl)-4-methylpiperazine (0.28 g, yield: 68.5%). MS m/z (ESI): 375.2 $[M+H]^+$.

Step 2: Synthesis of 5-cyclopropyl-2-methoxy-4-(4-(4-methylpiperazin-1-yl)piperidin-1-yl)aniline

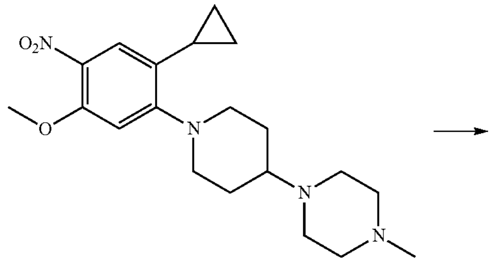

-continued

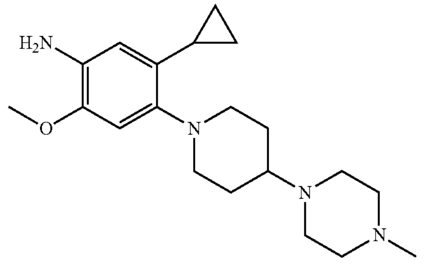

1-(1-(2-cyclopropyl-5-methoxy-4-nitrophenyl)piperidin-4-yl)-4-methylpiperazine (0.28 g, 0.65 mmol) was dissolved in a mixture of methanol (8 mL) and water (2 mL) and then Fe powder (0.18 g, 3.23 mmol) and $NH_4Cl$ (0.35 g, 6.47 mmol) were added. Under nitrogen protection, the mixture was heated to 70° C. for reaction for 2 hrs. The reaction mixture was cooled to room temperature and filtered through diatomaceous earth. The filtrate was concentrated, and then the residue was separated by the column chromatography to obtain 5-cyclopropyl-2-methoxy-4-(4-(4-methylpiperazin-1-yl)piperidin-1-yl)aniline (0.21 g, yield: 89.2%). MS m/z (ESI): 345.2 $[M+H]^+$.

Intermediate 9: Preparation of 2-methoxy-5-(1-methyl-1H-pyrazol-4-yl)-4-morpholinoaniline

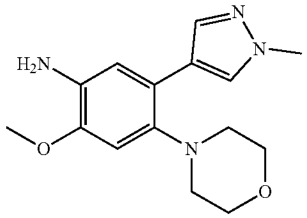

Step 1: Synthesis of 4-(2-fluoro-4-methoxy-5-nitrophenyl)-1-methyl-1H-pyrazole

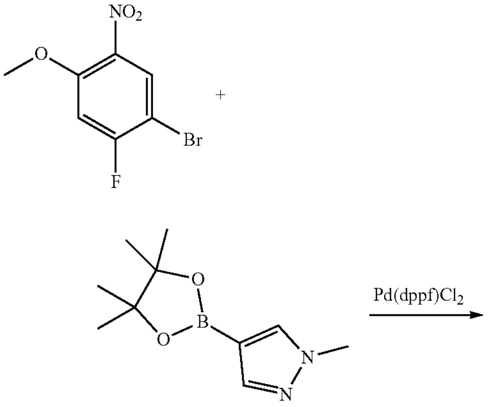

-continued

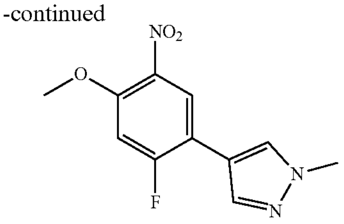

1-bromo-2-fluoro-4-methoxy-5-nitrobenzene (900 mg, 3.6 mmol) and 1-methyl-4-(4,4,5,5-tetramethyl-1,3,2-dioxaborolan-2-yl)-1H-pyrazole (1.12 g, 5.4 mmol), $K_2CO_3$ (1.49 g, 10.8 mmol) and Pd(dppf)$Cl_2$ (263 mg, 0.36 mmol) were added in 1,4-dioxane (15 mL) and water (3 mL), and then under nitrogen protection, the mixture was heated to 100° C. and stirred overnight. The reaction mixture was cooled to room temperature, diluted with water, and extracted with ethyl acetate. The organic phase was then washed with saturated brine, dried over anhydrous sodium sulfate and filtered. The filtrate was concentrated, and then the residue was separated by the column chromatography to obtain 4-(2-fluoro-4-methoxy-5-nitrophenyl)-1-methyl-1H-pyrazole (900 mg, yield: 99.5%). MS m/z (ESI): 252.1 $[M+H]^+$.

Step 2: Synthesis of 4-(5-methoxy-2-(1-methyl-1H-pyrazol-4-yl)-4-nitrophenyl)morpholine

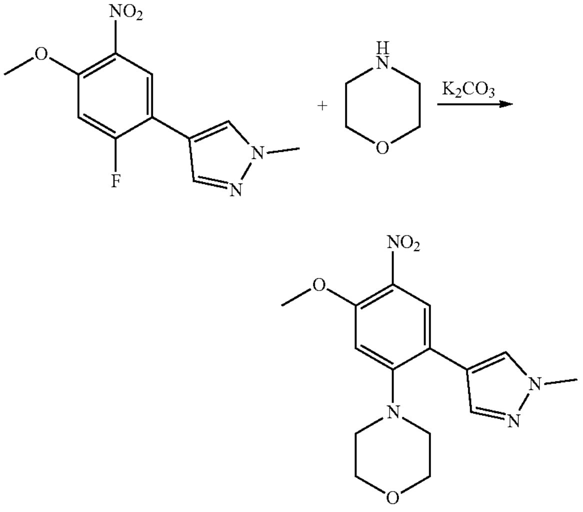

4-(2-fluoro-4-methoxy-5-nitrophenyl)-1-methyl-1H-pyrazole (150 mg, 0.60 mmol), $K_2CO_3$ (247.6 mg, 1.80 mmol) and morpholine (104 mg, 1.19 mmol) were added in DMSO (10 mL), and then under nitrogen protection, the mixture was heated to 100° C. and stirred overnight. The reaction mixture was cooled to room temperature, diluted with water, and extracted with ethyl acetate. The organic phase was then washed with saturated brine, dried over anhydrous sodium sulfate and filtered. The filtrate was concentrated, and then the residue was separated by the column chromatography to obtain 4-(5-methoxy-2-(1-methyl-1H-pyrazol-4-yl)-4-nitrophenyl)morpholine (160 mg, yield: 84.2%). MS m/z (EST): 319.1 $[M+H]^+$.

Step 3: Synthesis of 2-methoxy-5-(1-methyl-1H-pyrazol-4-yl)-4-morpholinoaniline

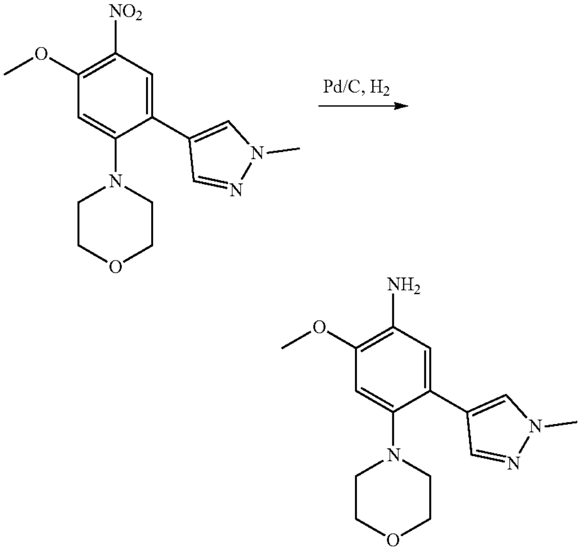

4-(5-methoxy-2-(1-methyl-1H-pyrazol-4-yl)-4-nitrophenyl)morpholine (160 mg, 0.52 mmol) was added in methanol (10 mL) and then 10% Pd/C (20 mg) was added. The mixture was stirred at room temperature under an atmospheric hydrogen atmosphere for 30 min. The reaction mixture was filtered, and the filtrate was concentrated. The residue was then separated by the column chromatography to obtain 2-methoxy-5-(1-methyl-1H-pyrazol-4-yl)-4-morpholinoaniline (106 mg, yield: 68.3%). MS m/z (ESI): 289.1 $[M+H]^+$.

Intermediate 10: Preparation of 2-methoxy-5-(1-methyl-1H-pyrazol-4-yl)-4-(4-methylpiperazin-1-yl)aniline

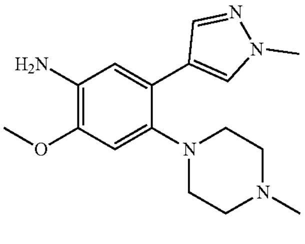

Step 1: Synthesis of 1-(5-methoxy-2-(1-methyl-1H-pyrazol-4-yl)-4-nitrophenyl)-4-methylpiperazine

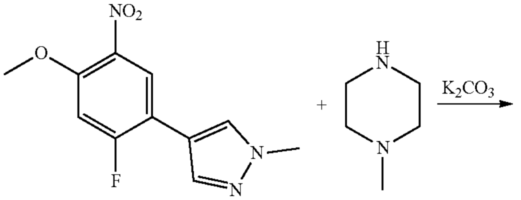

-continued

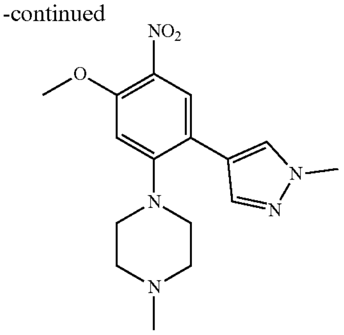

4-(2-fluoro-4-methoxy-5-nitrophenyl)-1-methyl-1H-pyrazole (150 mg, 0.60 mmol), $K_2CO_3$ (248 mg, 1.80 mmol) and N-methylpiperazine (119 mg, 1.19 mmol) were added in DMSO (10 mL), and then under nitrogen protection, the mixture was heated to 100° C. and stirred overnight. The reaction mixture was cooled to room temperature, diluted with water, and extracted with ethyl acetate. The organic phase was then washed with saturated brine, dried over anhdrous sodium sulfate and filtered. The filtrate was concentrated, and then the residue was separated by the column chromatography to obtain 1-(5-methoxy-2-(1-methyl-1H-pyrazol-4-yl)-4-nitrophenyl)-4-methylpiperazine (150 mg, yield: 75.8%). MS m/z (ESI): 332.1 $[M+H]^+$.

Step 2: Synthesis of 2-methoxy-5-(1-methyl-1H-pyrazol-4-yl)-4-(4-methylpiperazin-1-yl)aniline

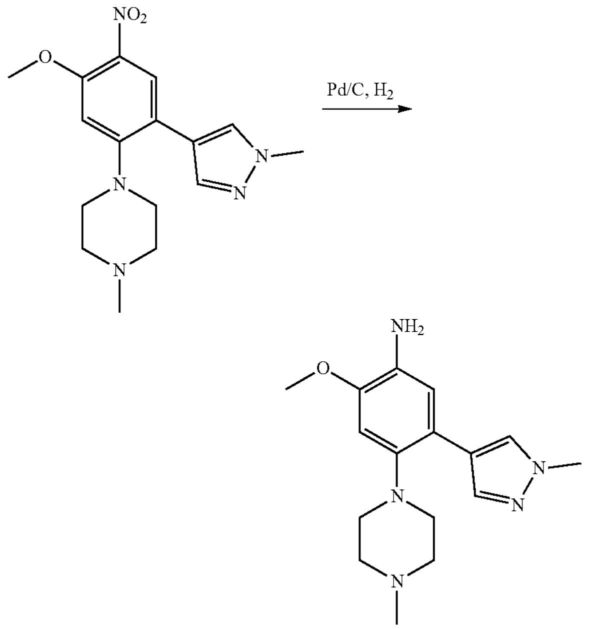

1-(5-methoxy-2-(1-methyl-1H-pyrazol-4-yl)-4-nitrophenyl)-4-methylpiperazine (150 mg, 0.45 mmol) was added in methanol (10 mL) and then 10% Pd/C (20 mg) was added. The mixture was stirred at room temperature under an atmospheric hydrogen atmosphere for 30 min. The reaction mixture was filtered, and the filtrate was concentrated. The residue was then separated by the column chromatography to obtain 2-methoxy-5-(1-methyl-1H-pyrazol-4-yl)-4-(4-methylpiperazin-1-yl)aniline (68 mg, yield: 50.3%). MS m/z (ESI): 302.1 $[M+H]^+$.

Intermediate 11: Preparation of 2-methoxy-5-(1-methyl-1H-pyrazol-4-yl)-4-(4-(4-methylpiperazin-1-yl)piperidin-1-yl)aniline

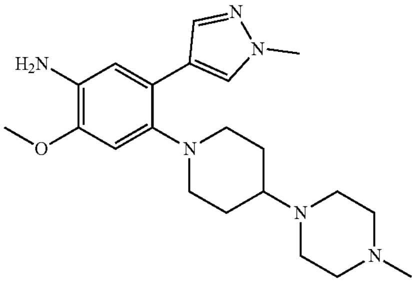

Step 1: Synthesis of 1-(1-(5-methoxy-2-(1-methyl-1H-pyrazol-4-yl)-4-nitrophenyl)piperidin-4-yl)-4-methylpiperazine

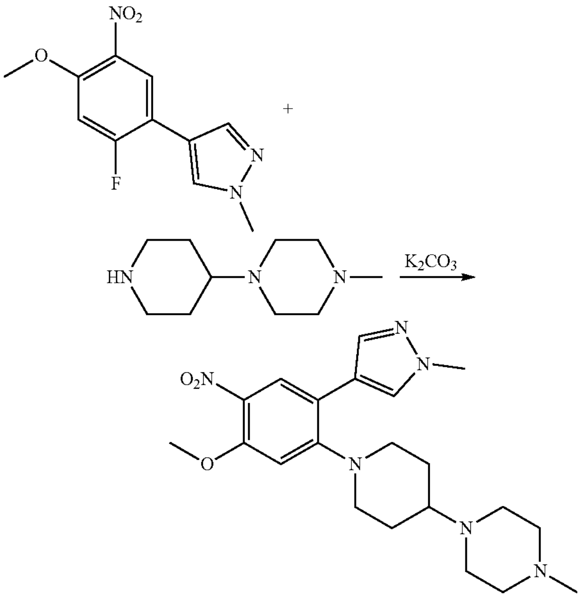

4-(2-fluoro-4-methoxy-5-nitrophenyl)-1-methyl-1H-pyrazole (0.30 g, 1.19 mmol) was dissolved in dimethylamine (5 mL) and then $K_2CO_3$ (0.50 g, 3.58 mmol) and 1-methyl-4-(piperidin-4-yl)piperazine (0.88 g, 4.78 mmol) were added. The mixture was heated to 100° C. under nitrogen protection for reaction for 3 hrs. The reaction mixture was cooled to room temperature and then water was added. The resulting mixture was extracted with ethyl acetate. The organic phase was then washed with saturated brine, dried over anhydrous sodium sulfate and filtered. The filtrate was concentrated, and then the residue was separated by the column chromatography to obtain 1-(1-(5-methoxy-2-(1-methyl-1H-pyrazol-4-yl)-4-nitrophenyl)piperidin-4-yl)-4-methylpiperazine (0.23 g, yield: 44.7%). MS m/z (ESI): 415.2 $[M+H]^+$.

Step 2: Synthesis of 2-methoxy-5-(1-methyl-1H-pyrazol-4-yl)-4-(4-(4-methylpiperazin-1-yl)piperidin-1-yl)aniline

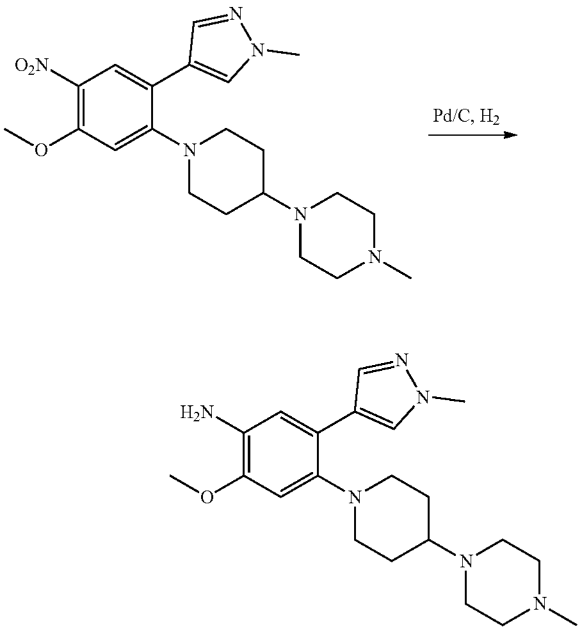

1-(1-(5-methoxy-2-(1-methyl-1H-pyrazol-4-yl)-4-nitrophenyl)piperidin-4-yl)-4-methylpiperazine (0.23 g, 0.53 mmol) was added in methanol (10 mL), and 10% Pd/C (0.10 g) was added. Hydrogen was charged to replace, and the mixture was reacted at room temperature under an atmospheric hydrogen atmosphere overnight. The reaction mixture was filtered through diatomaceous earth, and the filtrate was concentrated. The residue was then separated by the column chromatography to obtain 2-methoxy-5-(1-methyl-1H-pyrazol-4-yl)-4-(4-(4-methylpiperazin-1-yl)piperidin-1-yl)aniline (0.16 g, yield: 72.7%). MS m/z (ESI): 385.2 [M+H]1.

Intermediate 12: Preparation of 5-fluoro-2-methoxy-4-(4-(4-methylpiperazin-1-yl)piperidin-1-yl)aniline

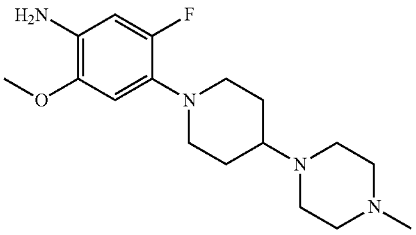

Step 1: Synthesis of 1,2-difluoro-4-methoxy-5-nitrobenzene

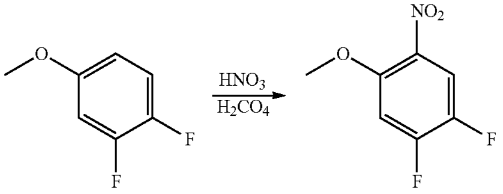

1,2-difluoro-4-methoxybenzene (1.626 mL, 13.88 mmol) was added to concentrated $H_2SO_4$ (6.81 g, 69.39 mmol) at 0° C. under an ice-water bath, and then concentrated $HNO_3$ (1.37 g, 15.27 mmol) was slowly added dropwise. After the addition, the mixture was reacted at room temperature for 3 hrs. After the reaction was completed, the reaction mixture was poured into ice water and extracted with EtOAc. The organic phases were washed with a saturated aqueous $NaHCO_3$ solution and a saturated NaCl solution, then combined, dried over anhydrous $Na_2SO_4$, filtered and concentrated. The residue was separated by silica gel column chromatography to obtain 1,2-difluoro-4-methoxy-5-nitrobenzene (1.14 g, 6.00 mmol, yield: 43.3%).

Step 2: Synthesis of 1-(1(2-fluoro-5-methoxy-4-nitrophenyl)piperidin-4-yl)-4-methylpiperazine

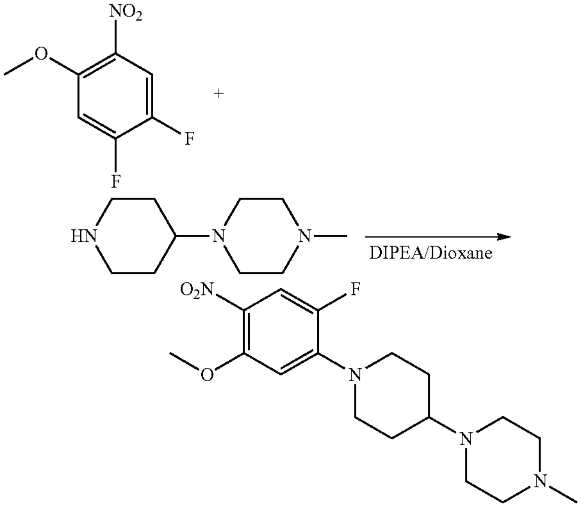

To a solution of 1,2-difluoro-4-methoxy-5-nitrobenzene (1.14 g, 6.00 mmol) in 1,4-dioxane (10 mL), 1-methyl-4-(piperidin-4-yl)piperazine (1.10 g, 6.00 mmol) and DIPEA (1.94 g, 14.99 mmol) were added, and then under $N_2$ protection, the mixture was heated to 100° C. and stirred for reaction for 2 hrs. After the reaction was completed, the reaction mixture was cooled to room temperature. After the reaction mixture was concentrated, a crude product of 1(1-(2-fluoro-5-methoxy-4-nitrophenyl)piperidin-4-yl)-4-methylpiperazine was obtained, which was directly used in the next step.

Step 3: Synthesis of 5-fluoro-2-methoxy-4-(4-(4-methylpiperazin-1-yl)piperidin-1-yl)aniline

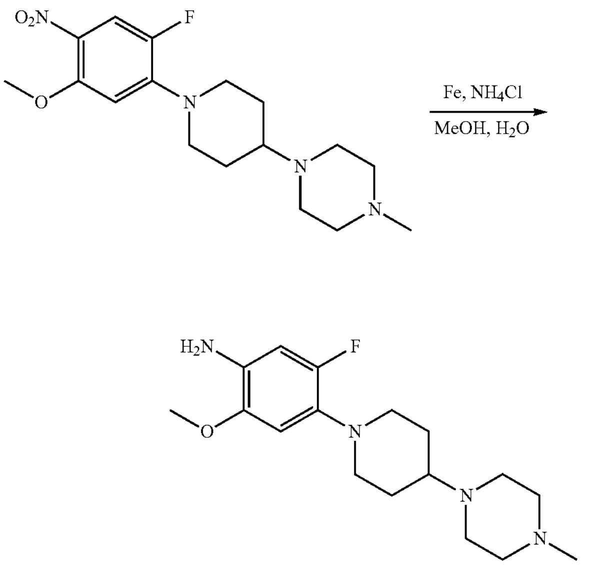

To the above crude product of 1-(1-(2-fluoro-5-methoxy-4-nitrophenyl)piperidin-4-yl]-4-methylpiperazine (2.26 g, 5.99 mmol), methanol (8 mL) and water (2 mL) were added, and then Fe powder (1.67 g, 29.95 mmol) and $NH_4Cl$ (3.20 g, 59.90 mmol) were added. Under $N_2$ protection, the mixture was heated to 75° C. and stirred for 3 hrs. After the reaction was completed, the reaction mixture was cooled to room temperature and filtered through diatomaceous earth. The filtrate was concentrated, and aqua ammonia was added to the residue. The mixture was then extracted with dichloromethane. The organic phase was washed with saturated brine, dried over anhydrous $Na_2SO_4$ and filtered. The filtrate was concentrated, and then the residue was separated by silica gel column chromatography to obtain 5-fluoro-2-methoxy-4-(4-(4-methylpiperazin-1-yl)piperidin-1-yl)aniline (1.44 g, 4.42 mmol, yield; 73.9%). MS m/z (ESI): 323.2 $[M+H]^+$.

Intermediate 13: Preparation of 5-chloro-2-methoxy-4-(4-(4-methylpiperazin-1-yl)piperidin-1-yl)aniline

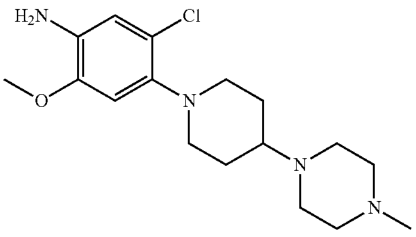

Intermediate 13 was synthesized from 1-chloro-2-fluoro-4-methoxybenzene by referring to the preparation of intermediate 12. MS m/z (ESI): 339.2 $[M+H]^+$.

Intermediate 14: Preparation of 2,5-dichloro-4-(4-(4-methylpiperazin-1-yl)piperidin-1-yl)aniline

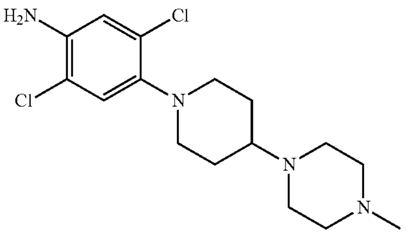 [SMILES: CN1CCN(C2CCN(c3cc(Cl)c(N)cc3Cl)CC2)CC1]

Intermediate 14 was prepared from 1,4-dichloro-2-fluorobenzene by referring to the preparation of intermediate 12. MS m/z (ESI): 343.2 $[M+H]^+$.

Intermediate 15: Preparation of 2-chloro-5-methyl-4-(4-(4-methylpiperazin-1-yl)piperidin-1-yl)aniline

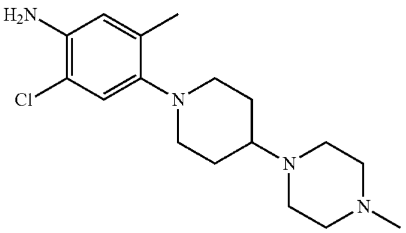 [SMILES: Cc1cc(N)c(Cl)cc1N1CCC(N2CCN(C)CC2)CC1]

Intermediate 15 was prepared from 1-chloro-5-fluoro-4-methyl-2-nitrobenzene by referring to the preparation of intermediate 1. MS m/z (ESI): 323.2 $[M+H]^+$.

Intermediate 16: Preparation of 4-(4-(4-ethylpiperazin-1-yl)piperidin-1-yl)-2-methoxy-5-methylaniline

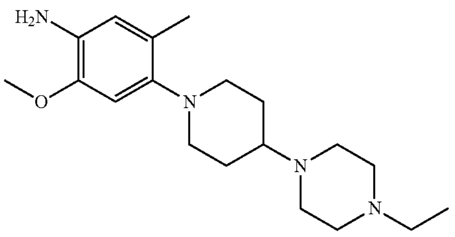 [SMILES: CCN1CCN(C2CCN(c3cc(OC)c(N)cc3C)CC2)CC1]

Intermediate 16 was prepared by referring to the preparation of intermediate 1. MS m/z (ESI): 333.2 $[M+H]^+$.

II. Preparation of Specific Examples

Example 1: Preparation of $N^4$-(2-(2-fluorophenyl)pyridin-4-yl)-$N^6$-(2-methoxy-5-methyl-4-(4-(4-methylpiperazin-1-yl)piperidin-1-yl)phenyl)pyrimidine-4,6-diamine

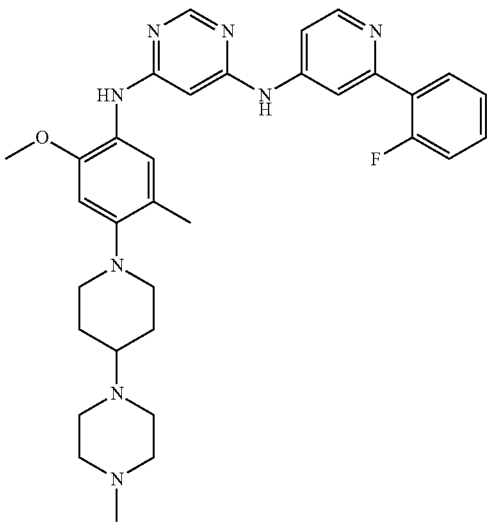 [SMILES: COc1cc(N2CCC(N3CCN(C)CC3)CC2)c(C)cc1Nc1cc(Nc2ccnc(-c3ccccc3F)c2)ncn1]

Step 1: s thesis of 2-(2-fluorophenyl)pyridin-4-amine

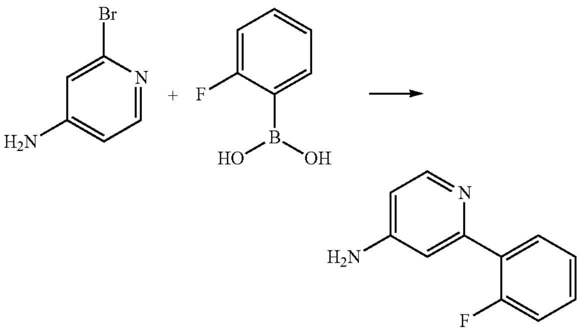

2-bromopyridin-4-amine (10 g, 57.80 mmol) and (2-fluorophenyl)boronic acid (9.70 g, 69.36 mmol) were dissolved in 1,4-dioxane (170 mL) and then an aqueous $Na_2CO_3$ solution (2 M, 86.7 mL, 173.40 mmol) and $Pd(PPh_3)_4$ (1.34 g, 1.16 mmol) were added. After nitrogen was charged to replace three times, the reaction mixture was heated to 90° C. and stirred for 18 hrs. After the reaction was completed, the reaction mixture was cooled to room temperature. Saturated brine (600 mL) was added, and then the mixture was extracted with ethyl acetate. The organic phase was washed with saturated brine, dried over anhydrous sodium sulfate, filtered and concentrated. The residue was separated by the column chromatography [eluent: EtOAc/PE=0-50%] to obtain 2-(2-fluorophenyl)pyridin-4-amine (10.0 g, yield: 92%). MS m/z (ESI): 189.0 $[M+H]^+$.

Step 2: Synthesis of 6-chloro-N-(2-2-fluorophenyl)pyridin-4-yl)pyrimidin-4-amine

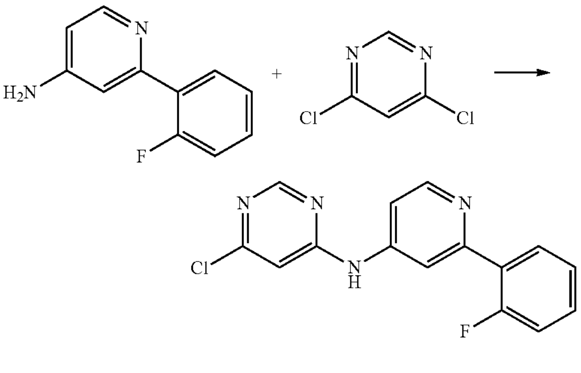

2-(2-fluorophenyl)pyridin-4-amine (5 g, 26.57 mmol) was added in DMF (50 mL), and 60% NaH (1.59 g, 39.85 mmol) was added under an ice-water bath. The mixture was stirred at room temperature for 1 hr and then 4,6-dichloropyrimidine (4.75 g, 31.88 mmol) was added under an ice-water bath. The mixture was stirred at room temperature overnight. Ethanol was added to the reaction mixture to quench the reaction, and the resulting mixture was concentrated. The residue was separated by the column chromatography to obtain 6-chloro-N-(2-(2-fluorophenyl)pyridin-4-yl)pyrimidin-4-amine (1 g, yield: 12.5%). MS m/z (ESI): 301.2 $[M+H]^+$.

Step 3: Synthesis of $N^4$-(2-(2-fluorophenyl)pyridin-4-yl)-$N^6$-(2-methoxy-5-methyl-4-(4-(4-methylpiperazin-1-yl)piperidin-1-yl)phenyl)pyrimidine-4,6-diamine

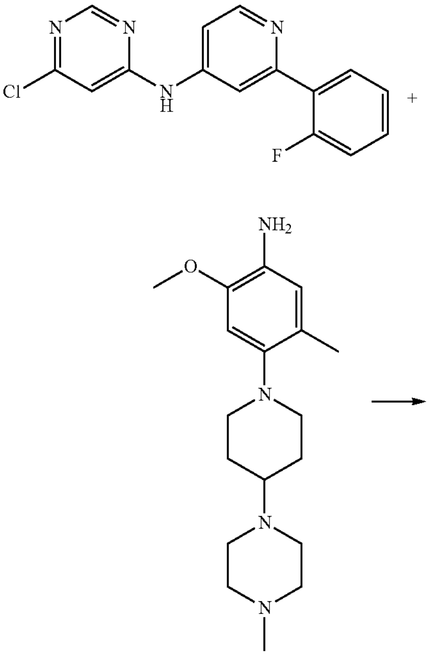

-continued

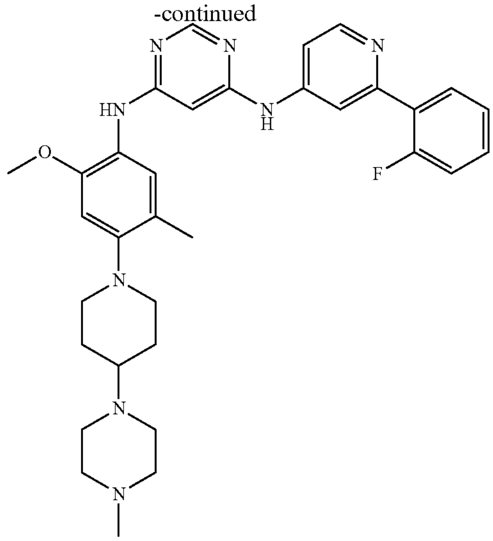

6-chloro-N-(2-(2-fluorophenyl)pyridin-4-yl)pyrimidin-4-amine (50 mg, 0.17 mmol) and 2-methoxy-5-methyl-4-(4-(4-methylpiperazin-1-yl)piperidin-1-yl)aniline (63.5 mg, 0.2 mmol) were added to ethylene glycol monomethyl ether (3 mL) and then a 4 M HCl/dioxane solution (0.17 mL, 0.67 mmol) was added. Then the mixture was stirred at 120° C. overnight. The reaction mixture was neutralized with an $NH_3$/MeOH solution and concentrated. The residue was then separated by the reversed-phase column chromatography to obtain $N^4$-(2-(2-fluorophenyl)pyridin-4-yl)-$N^6$-(2-methoxy-5-methyl-4-(4-(4-methylpiperazin-1-yl)piperidin-1-yl)phenyl)pyrimidine-4,6-diamine (21.5 mg, yield: 22.9%). MS m/z (ESI): 583.2 $[M+H]^+$.

$^1$H NMR (400 MHz, MeOH-$d_4$) δ 8.27 (d, J=5.9 Hz, 1H), 8.17 (s, 1H), 7.82 (s, 1H), 7.64-6.59 (m, 2H), 7.39-7.33 (m, 1H), 7.20 (t, J=7.5 Hz, 1H), 7.15-7.09 (m, 2H), 6.66 (s, 1H), 5.95 (s, 1H), 3.72 (s, 3H), 3.08 (d, J=11.9 Hz, 2H), 2.65-2.53 (m, 6H), 2.48-2.41 (m, 4H), 2.31-2.5 (m, 1H), 2.22 (s, 3H), 2.14 (s, 3H), 1.94-1.88 (m, 2H), 1.65-1.56 (m, 2H).

Example 2: Preparation of $N^4$-(2-(2-fluorophenyl)pyridin-4-yl)-$N^6$-(2-methoxy-5-methyl-4-(4-morpholinopiperidin-1-yl)phenyl)pyrimidine-4,6-diamine

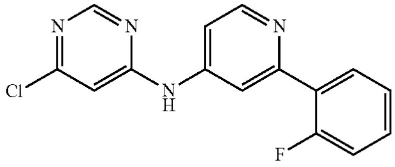

+

-continued

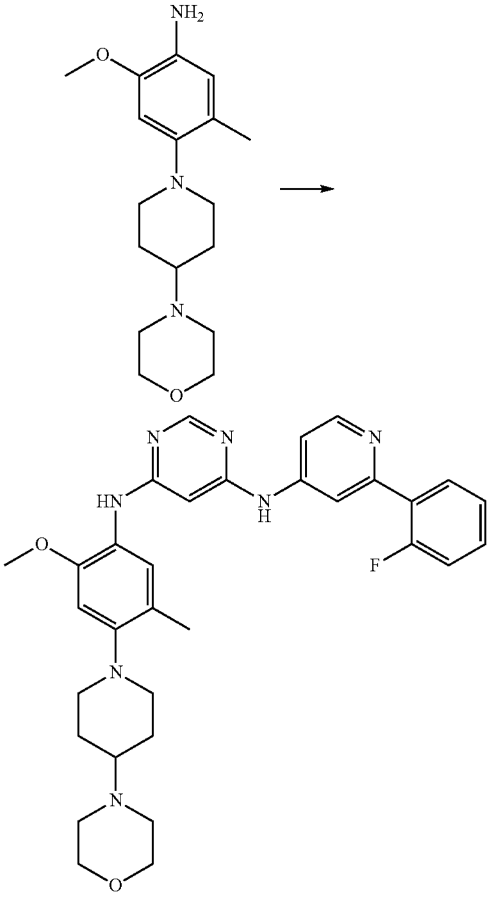

2-methoxy-5-methyl-4-(4-morpholinopiperidin-1-yl)aniline (0.24 g, 0.76 mmol) and 6-chloro-N-(2-(2-fluorophenyl)pyridin-4-yl)pyrimidin-4-amine (0.20 g, 0.64 mmol) were added in tert-butanol (10 mL) and then addition of p-toluenesulfonic acid monohydrate (0.60 g, 3.18 mmol) was added. The mixture was heated to 100° C. for reaction for 36 hrs. The reaction mixture was cooled to room temperature, neutralized with aqua ammonia, and concentrated. The residue was then separated by the column chromatography to obtain $N^4$-(2-(2-fluorophenyl)pyridin-4-yl)-$N^6$-(2-methoxy-5-methyl-4-(4-morpholinopiperidin-1-yl)phenyl)pyrimidine-4,6-diamine (80 mg, yield: 41.1%). MS m/z (ESI): 570.2 $[M+H]^+$.

$^1$H NMR (400 MHz, DMSO-$d_6$) δ 9.59 (s, 1H), 8.43 (d, J=5.6 Hz, 1H), 8.37 (s, 1H), 8.25 (s, 1H), 7.98 (d, J=2.0 Hz, 1H), 7.91 (td, J=7.9, 1.9 Hz, 1H), 7.73 (dd, J=5.7, 2.2 Hz, 1H), 7.52-7.41 (m, 1H), 7.36-7.26 (m, 2H), 7.21 (s, 1H), 6.72 (s, 1H), 5.90 (s, 1H), 3.76 (s, 3H), 3.59 (t, J=4.6 Hz, 4H), 3.11 (d, J=11.5 Hz, 2H), 2.92 (s, 2H), 2.64 (t, J=11.5 Hz, 2H), 2.35-2.21 (m, 2H), 2.17 (s, 3H), 1.99 (dt, J=13.2, 7.0 Hz, 1H), 1.89 (d, J=11.6 Hz, 2H), 1.64-1.49 (m, 2H).

Example 3: Preparation of $N^4$-(2-ethoxy-5-methyl-4-(4-(4-methylpiperazin-1-yl)piperidin-1-yl)phenyl)-$N^6$-(2-(2-fluorophenyl)pyridin-4-yl)pyrimidine-4,6-diamine

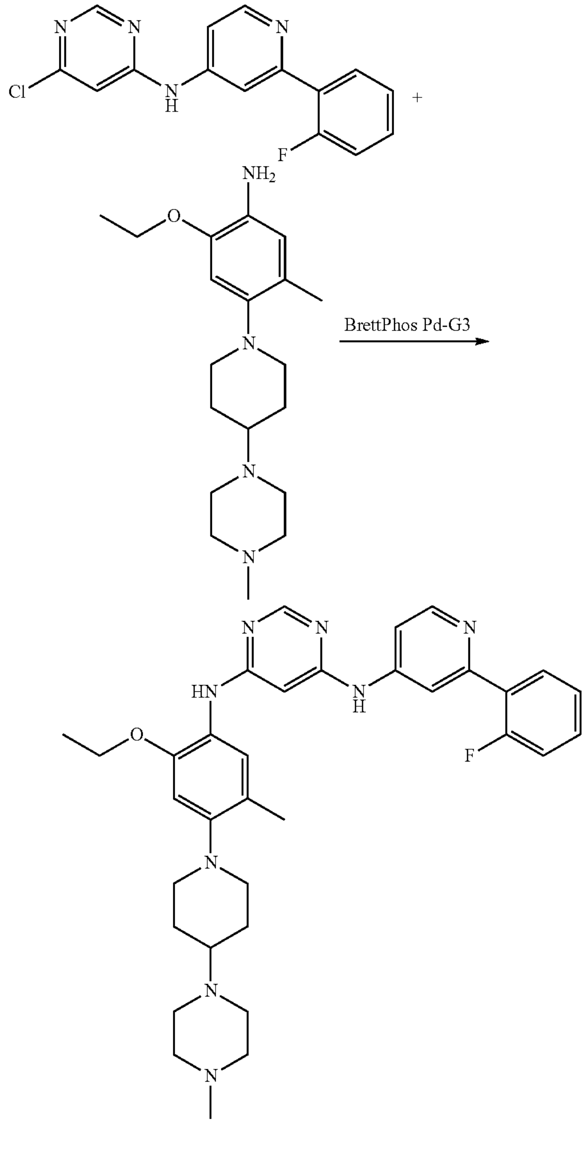

6-chloro-N-(2-(2-fluorophenyl)pyridin-4-yl)pyrimidin-4-amine (180 mg, 0.60 mmol), 2-ethoxy-5-methyl-4-(4-(4-methylpiperazin-1-yl)piperidin-1-yl)aniline (219 mg, 0.66 mmol), NaO$^t$Bu (115 mg, 1.20 mmol) and BrettPhos Pd-G3 (109 mg, 0.12 mmol) were added in toluene (10 mL), and then under nitrogen protection, the mixture was heated to 90° C. and stirred overnight. The reaction mixture was filtered, and the filtrate was concentrated. The residue was then separated by the column chromatography to obtain a crude product. The crude product was then separated by a preparative column to obtain $N^4$-(2-ethoxy-5-methyl-(4-(4-methylpiperazin-1-yl)piperidin-1-yl)phenyl)-$N^6$-(2-(2-fluorophenyl)pyridin-4-yl)pyrimidine-4,6-diamine (65 mg, yield: 18.0%). MS m/z (ESI): 597.3 $[M+H]^+$.

$^1H$ NMR (400 MHz, DMSO-$d_6$) δ 9.58 (s, 1H), 8.43 (d, J=5.7 Hz, 1H), 8.28 (d, J=15.0 Hz, 2H), 7.99 (s, 1H), 7.91 (td, J=7.9, 1.8 Hz, 1H), 7.73 (dd, J=5.7, 2.1 Hz, 1H), 7.49-7.44 (m, 1H), 7.37-7.26 (m, 2H), 7.17 (s, 1H), 6.70 (s, 1H), 5.91 (s, 1H), 4.02 (q, J=7.0 Hz, 2H), 3.43-3.38 (m, 2H), 3.09 (d, J=11.4 Hz, 2H), 2.61 (t, J=11.5 Hz, 4H), 2.39-2.26 (m, 5H), 2.16 (s, 3H), 2.15 (s, 3H), 1.85 (d, J=11.8 Hz, 2H), 1.62-1.51 (m, 2H), 1.24 (t, J=6.9 Hz, 3H).

Example 4: Preparation of $N^4$-(2-(difluoromethoxy)-5-methyl-4-(4-(4-methylpiperazin-1-yl)piperidin-1-yl)phenyl)-$N^6$-(2-(2-fluorophenyl)pyridin-4-yl)pyrimidine-4,6-diamine

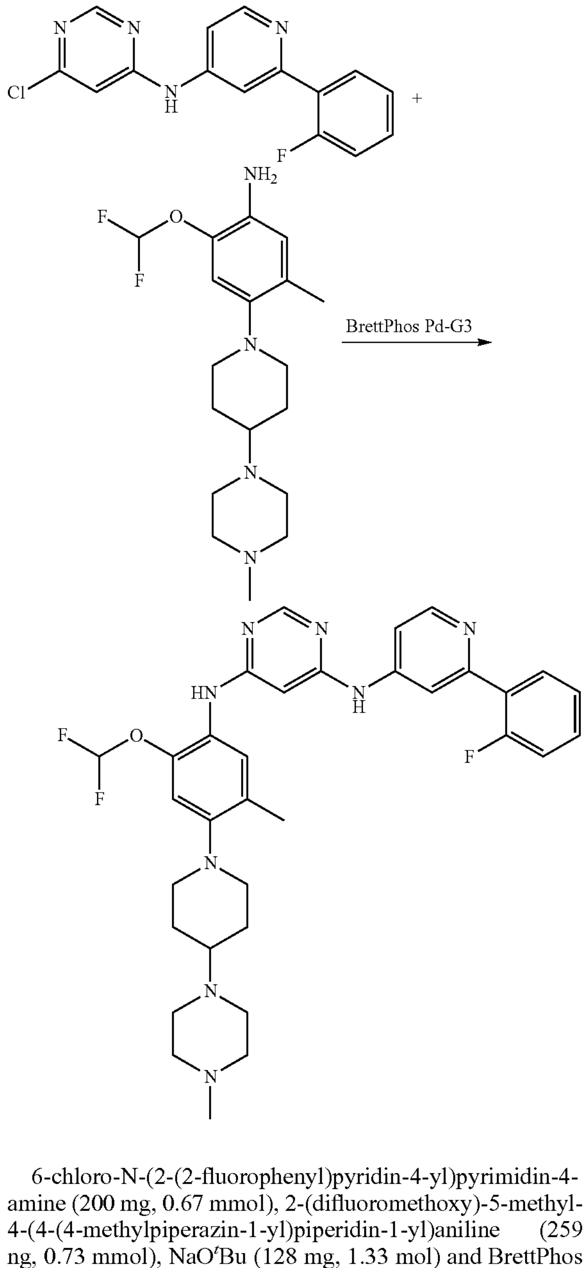

6-chloro-N-(2-(2-fluorophenyl)pyridin-4-yl)pyrimidin-4-amine (200 mg, 0.67 mmol), 2-(difluoromethoxy)-5-methyl-4-(4-(4-methylpiperazin-1-yl)piperidin-1-yl)aniline (259 ng, 0.73 mmol), NaO$^t$Bu (128 mg, 1.33 mol) and BrettPhos Pd-G3 (121 mg, 0.13 mmol) were added in toluene (10 mL), and then under nitrogen protection, the mixture was stirred at 90° C. overnight. The reaction mixture was cooled to room temperature and filtered. The filtrate was concentrated, and then the residue was separated by the column chromatography to obtain a crude product. The crude product was then separated by a preparative column to obtain $N^4$-(2-(difluoromethoxy)-5-methyl-4-(4-(4-methylpiperazin-1-yl)piperidin-1-yl)phenyl)-$N^6$-(2-(2-fluorophenyl)pyridin-4-yl)pyrimidine-4,6-diamine (25 mg, yield: 6.1%). MS m/z (ESI): 619.3 $[M+H]^+$.

$^1$H NMR (400 MHz, DMSO-$d_6$) δ 9.64 (s, 1H), 8.65 (s, 1H), 8.44 (d, J=5.7 Hz, 1H), 8.27 (s, 1H), 8.00 (s, 1H), 7.91 (td, J=7.9, 1.9 Hz, 1H), 7.73 (dd, J=5.7, 2.1 Hz, 1H), 7.50-7.44 (m, 1H), 7.36-7.26 (m, 3H), 7.21 (s, 0.25H), 7.03 (s, 0.5H), 6.84 (d, J=3.2 Hz, 1.25H), 5.98 (s, 1H), 3.11 (d, J=11.4 Hz, 2H), 2.59 (td, J=11.9, 2.2 Hz, 4H), 2.41-2.26 (m, 5H), 2.22 (s, 3H), 2.15 (s, 3H), 1.86 (d, J=11.0 Hz, 2H), 1.64-1.52 (m, 2H).

Example 5: Preparation of $N^4$-(2-(2-fluorophenyl)pyridin-4-yl)-$N^6$-(5-methyl-4-(4-(4-methylpiperazin-1-yl)piperidin-1-yl)-2-(2,2,2-trifluoroethoxy)phenyl)pyrimidine-4,6-diamine

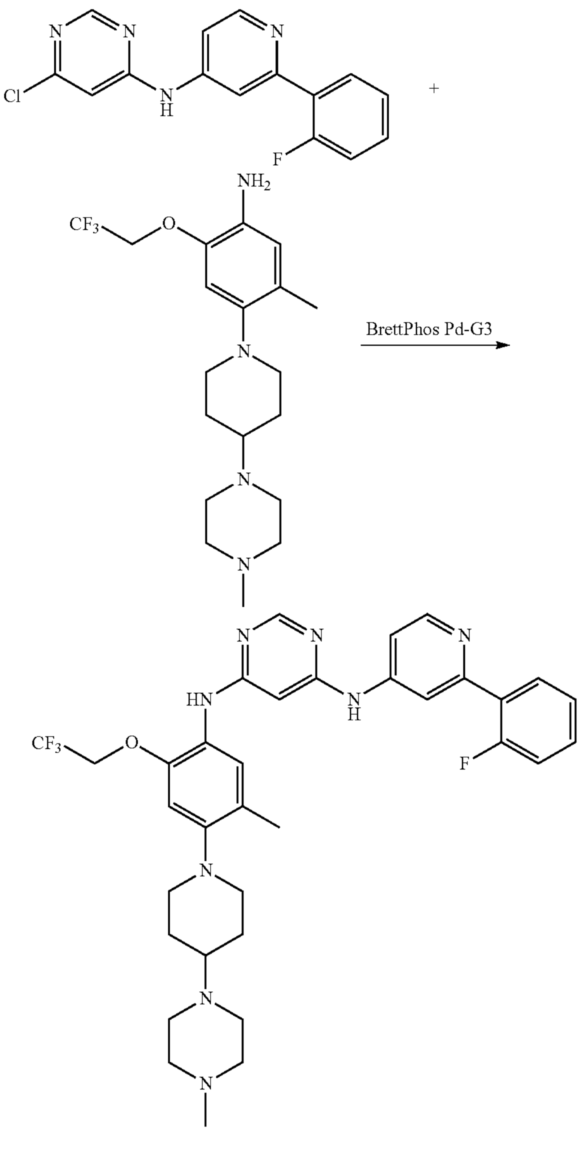

6-chloro-N-(2-(2-fluorophenyl)pyridin-4-yl)pyrimidin-4-amine (53 mg, 0.18 mmol), 5-methyl-4-(4-(4-methylpiperazin-1-yl)piperidin-1-yl)-2-(2,2,2-trifluoroethoxy)aniline (68 mg, 0.18 mmol), $NaO^tBu$ (34 mg, 0.35 mmol) and BrettPhos Pd-3 (16 g, 0.02 mmol) were added in toluene (10 mL), and then under nitrogen protection, the mixture was stirred at 90° C. overnight. The reaction mixture was cooled to room temperature and filtered. The filtrate was concentrated, and then the residue was separated by the column chromatography to obtain a crude product. The crude product was then separated by a preparative column to obtain $N^4$-(2-(2-fluorophenyl)pyridin-4-yl)-$N^6$-(5-methyl-4-(4-(4-methylpiperazin-1-yl)piperidin-1-yl)-2-(2,2,2-trifluoroethoxy)phenyl)pyrimidine-4,6-diamine (1.2 mg, yield: 1%). MS m/z (ESI): 651.4 $[M+H]^+$.

$^1$H NMR (400 MHz, DMSO-$d_6$) δ 9.58 (s, 1H), 8.43 (t, J=2.8 Hz, 2H), 8.25 (s, 1H), 7.99 (d, J=2.0 Hz, 1H), 7.91 (td, J=7.9, 2.0 Hz, 1H), 7.73 (dd, J=5.7, 2.1 Hz, 1H), 7.46 (td, J=5.6, 2.6 Hz, 1H), 7.31 (dd, J=9.3, 6.9 Hz, 2H), 7.16 (s, 1H), 6.84 (s, 1H), 5.88 (s, 1H), 4.68 (q, J=8.9 Hz, 2H), 3.11 (d, J=11.5 Hz, 2H), 2.92 (s, 2H), 2.68-2.60 (m, 3H), 2.39-2.27 (m, 6H), 2.18 (s, 3H), 2.15 (s, 3H), 2.05-1.94 (m, 2H), 1.86 (d, J=12.1 Hz, 2H), 1.64-1.53 (m, 2H).

Example 6: Preparation of $N^4$-(5-ethyl-2-methoxy-4-(4-(4-methylpiperazin-1-yl)piperidin-1-yl)phenyl)-$N^6$-(2-(2-fluorophenyl)pyridin-4-yl)pyrimidine-4,6-diamine

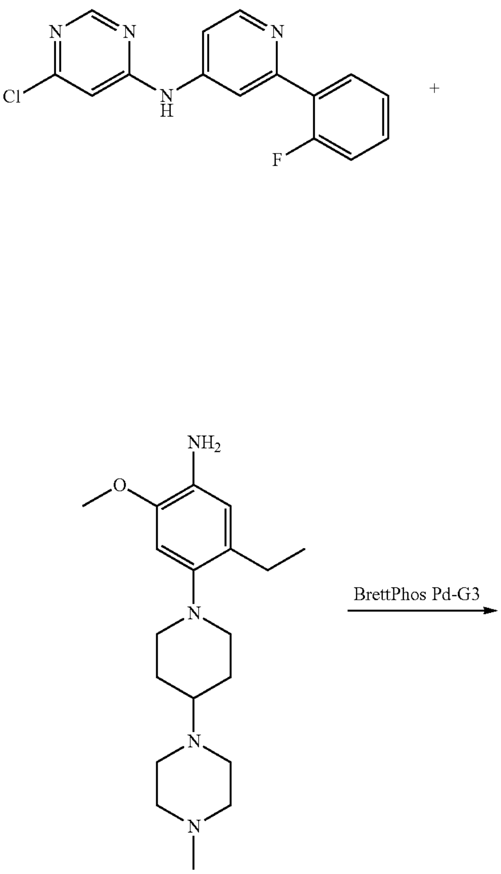

-continued

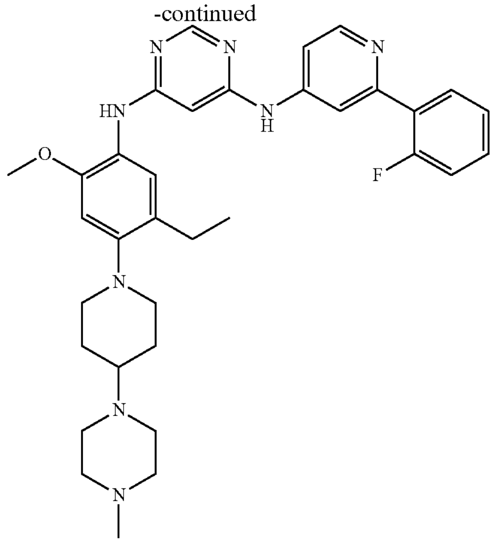

6-chloro-N-(2-(2-fluorophenyl)pyridin-4-yl)pyrimidin-4-amine (100 mg, 0.33 mmol), 5-ethyl-2-methoxy-4-(4-(4-methylpiperazin-1-yl)piperidin-1-yl)aniline (122 mg, 0.37 mmol), NaO$^t$Bu (63.9 mg, 0.67 mmol) and BrettPhos Pd-G3 (60.3 mg, 0.07 mmol) were added in toluene (10 mL), and then under nitrogen protection, the mixture was stirred at 90° C. overnight. The reaction mixture was cooled to room temperature and filtered. The filtrate was concentrated, and then the residue was separated by the column chromatography to obtain a crude product. The crude product was then separated by a preparative column to obtain N$^4$-(5-ethyl-2-methoxy-4-(4-(4-methylpiperazin-1-yl)piperidin-1-yl)phenyl)-N$^6$-(2-(2-fluorophenyl)pyridin-4-yl)pyrimidine-4,6-diamine (38 mg, yield: 19.2%). MS m/z (ESI): 597.3 [M+H]$^+$.

$^1$H NMR (400 MHz, DMSO-d$_6$) δ 9.59 (s, 1H), 8.47-8.36 (m, 2H), 8.26 (s, 1H), 7.98 (t, J=1.9 Hz, 1H), 7.91 (td, J=7.9, 1.9 Hz, 1H), 7.73 (dd, J=5.6, 2.1 Hz, 1H), 7.51-7.41 (m, 1H), 7.37-7.27 (m, 2H), 7.23 (s, 1H), 6.78 (s, 1H), 5.90 (s, 1H), 3.76 (s, 3H), 3.29-3.23 (m, 2H), 3.03 (d, J=11.3 Hz, 2H), 2.71-2.64 (m, 2H), 2.57 (q, J=7.5 Hz, 4H), 2.38-2.25 (m, 5H), 2.15 (s, 3H), 1.85 (d, J=11.7 Hz, 2H), 1.61-1.51 (m, 2H), 1.16 (t, J=7.5 Hz, 3H).

Example 7: Preparation of N$^4$-(2-(2-fluorophenyl)pyridin-4-yl)-N$^6$-(5-isopropyl-2-methoxy-4-(4-(4-methylpiperazin-1-yl)piperidin-1-yl)phenyl)pyrimidine-4,6-diamine

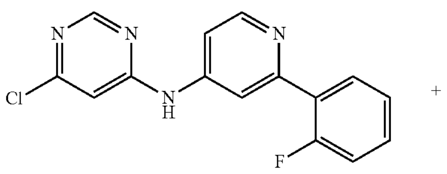

-continued

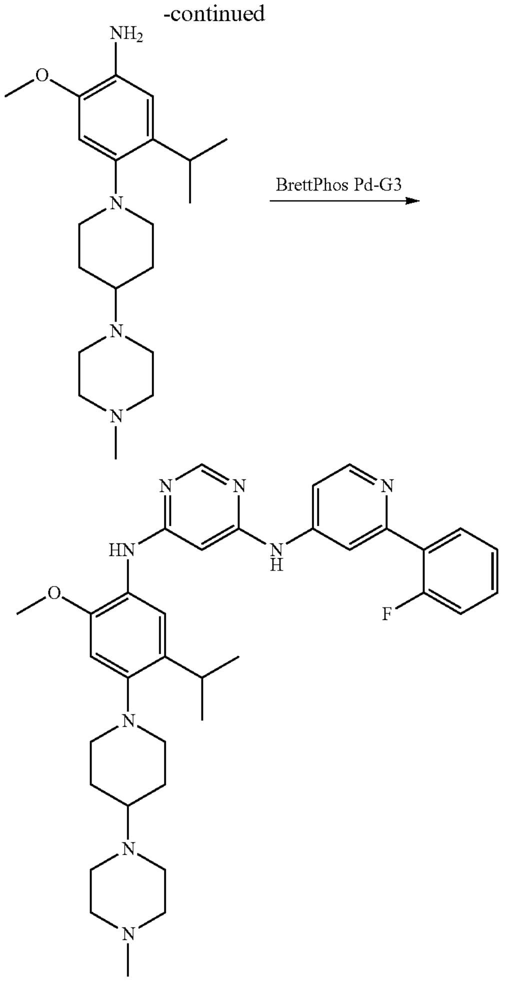

To a solution of 5-isopropyl-2-methoxy-4-(4-(4-methylpiperazin-1-yl)piperidin-1-yl)aniline (0.14 g, 0.39 mmol) in toluene (10 mL), 6-chloro-N-(2-(2-fluorophenyl)pyridin-4-yl)pyrimidin-4-amine (0.12 g, 0.39 mmol), BrettPhos Pd-G3 (0.04 g, 0.04 mmol) and NaO$^t$Bu (0.07 g, 0.77 mmol) were added, and then under nitrogen protection, the mixture was heated to 80° C. for reaction overnight. The reaction mixture was cooled to room temperature and concentrated. The residue was then separated by the column chromatography to obtain a crude product. The crude product was then separated by a preparative column to obtain N$^4$-(2-(2-fluorophenyl)pyridin-4-yl)-N$^6$-(5-isopropyl-2-methoxy-4-(4-(4-methylpiperazin-1-yl)piperidin-1-yl)phenyl)pyrimidine-4,6-diamine (50.5 mg, yield: 21.3%). MS m/z (ESI): 611.4 [M+H]$^+$.

$^1$H NMR (400 MHz, DMSO-d$_6$) δ 9.60 (s, 1H), 8.43 (d, J=4.6 Hz, 2H), 8.26 (s, 1H), 7.98 (s, 1H), 7.91 (t, J=7.9 Hz, 1H), 7.73 (d, J=4.4 Hz, 1H), 7.46 (q, J=6.9 Hz, 1H), 7.31 (t, J=7.9 Hz, 2H), 7.26 (s, 1H), 6.81 (s, 1H), 5.88 (s, 1H), 3.76 (s, 3H), 2.98 (d, J=11.1 Hz, 2H), 2.71 (t, J=11.6 Hz, 2H), 2.32 (s, 5H), 2.15 (s, 3H), 1.85 (d, J=11.9 Hz, 2H), 1.64-1.50 (m, 2H), 1.14 (d, J=6.8 Hz, 6H).

Example 8: Preparation of N$^4$-(5-cyclopropyl-2-methoxy-4-(4-(4-methylpiperazin-1-yl)piperidin-1-yl)phenyl)-N$^6$-(2-(2-fluorophenyl)pyridin-4-yl)pyrimidine-4,6-diamine

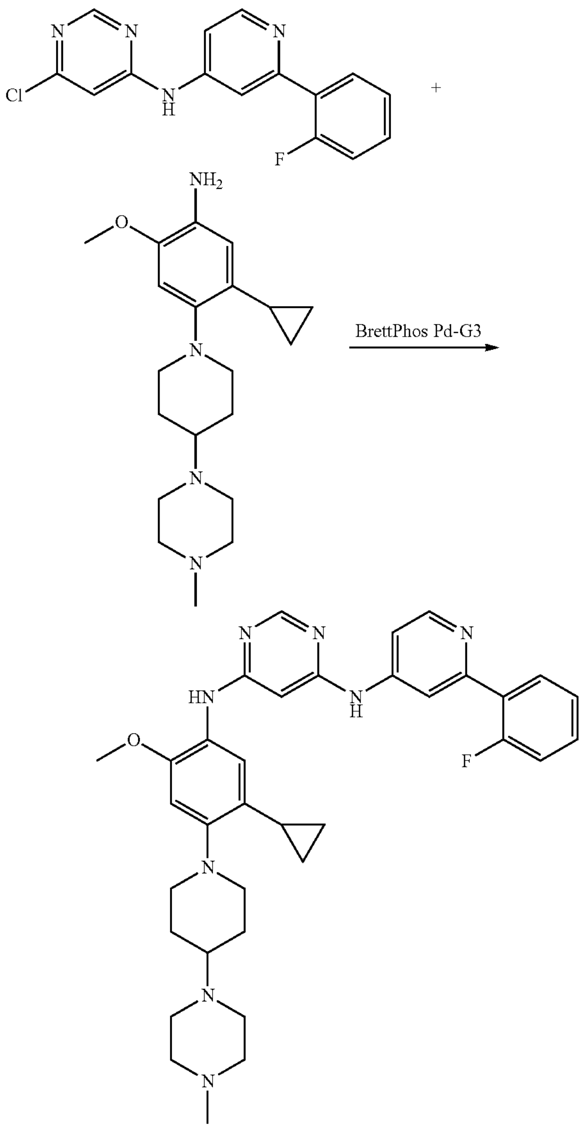

To a solution of 5-cyclopropyl-2-methoxy-4-(4-(4-methylpiperazin-1-yl)piperidin-1-yl)aniline (0.20 g, 0.55 mmol) in toluene (10 mL), 6-chloro-N-(2-(2-fluorophenyl)pyridin-4-yl)pyrimidin-4-amine (0.16 g, 0.49 mmol), BrettPhos Pd-G3 (0.05 g, 0.06 mmol) and NaO$^t$Bu (0.11 g, 1.10 mmol) were added, and then under nitrogen protection, the mixture was heated to 80° C. for reaction overnight. The reaction mixture was cooled to room temperature and concentrated. The residue was then separated by the column chromatography to obtain a crude product. The crude product was then separated by a preparative column to obtain N$^4$-(5-cyclopropyl-2-methoxy-4-(4-(4-methylpiperazin-1-yl)piperidin-1-yl)phenyl)-N$^6$—(2-(2-fluorophenyl)pyridin-4-yl)pyrimidine-4,6-diamine (96.8 mg, yield: 28.8%). MS m/z (ESI): 609.4 $[M+H]^+$.

$^1$H NMR (400 MHz, DMSO-$d_6$) δ 9.58 (s, 1H), 8.42 (d, J=5.7 Hz, 1H), 8.34 (s, 1H), 8.24 (d, J=0.9 Hz, 1H), 7.98 (t, J=1.9 Hz, 1H), 7.91 (td, J=7.9, 1.9 Hz, 1H), 7.73 (dd, J=5.7, 2.1 Hz, 1H), 7.46 (tdd, J=7.7, 5.1, 1.9 Hz, 1H), 7.36-7.26 (m, 2H), 6.78 (s, 1H), 6.71 (s, 1H), 5.83 (s, 1H), 3.75 (s, 3H), 2.67 (t, J=11.2 Hz, 2H), 2.41-2.23 (m, 5H), 2.19-2.07 (m, 4H), 1.87 (d, J=11.7 Hz, 2H), 1.67-1.54 (m, 2H), 0.97-0.87 (m, 2H), 0.63-0.54 (m, 2H).

Example 9: Preparation of N$^4$-(2-(2-fluorophenyl)pyridin-4-yl)-N$^6$-(2-methoxy-5-(1-methyl-1H-pyrazol-4-yl)-4-(4-(4-methylpiperazin-1-yl)piperidin-1-yl)phenyl)pyrimidine-4,6-diamine

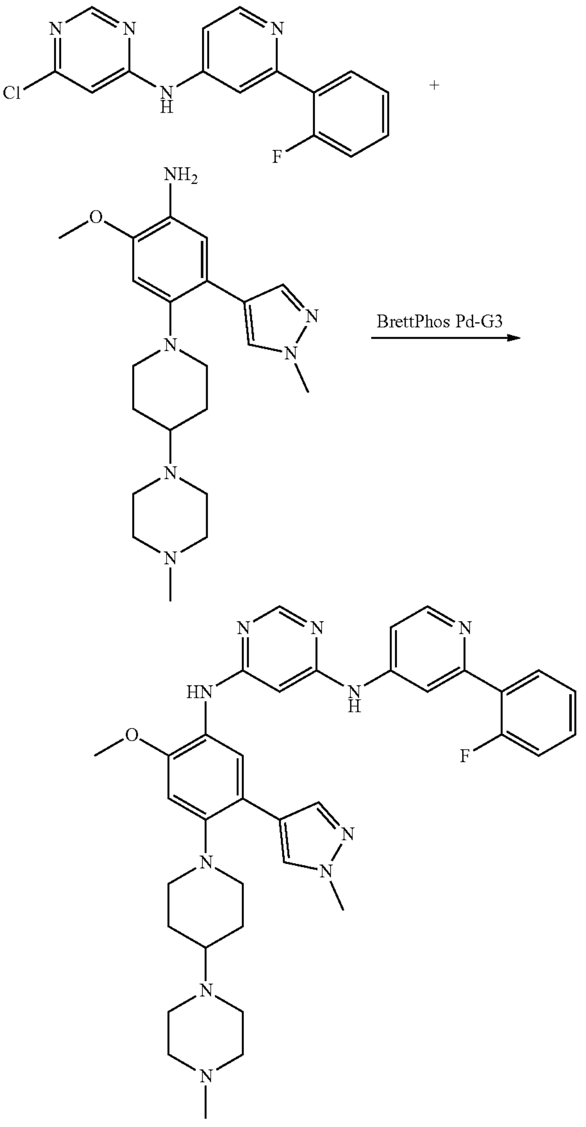

To a solution of 2-methoxy-5-(I-methyl-NH-pyrazol-4-yl)-4-(4-(4-methylpiperazin-1-yl)piperidin-1-yl)aniline (0.16 g, 0.39 mmol) in toluene (10 mL), 6-chloro-N-(2-(2-fluorophenyl)pyridin-4-yl)pyrimidin-4-amine (0.12 g, 0.39 mmol), BrettPhos Pd-G3 (0.06 g, 0.07 mmol) and NaO$^t$Bu (0.07 g, 0.78 mmol) were added, and then under nitrogen protection, the mixture was heated to 80° C. for reaction overnight. The reaction mixture was cooled to room temperature and concentrated. The residue was then separated by the column chromatography to obtain a crude product. The crude product was then separated by a preparative column to obtain $N^4$-(2-(2-fluorophenyl)pyridin-4-yl)-$N^6$-(2-methoxy-5-(1-methyl-1H-pyrazol-4-yl)-4-(4-(4-methylpiperazin-1-yl)piperidin-1-yl)phenyl)pyrimidine-4,6-diamine (65 mg, yield: 25.2%). MS nm/z (ESI): 649.4 $[M+H]^+$.

$^1$H NMR (400 MHz, DMSO-$d_6$) δ 9.60 (s, 1H), 8.45-8.39 (m, 24) 8.26 (d, J=0.8 Hz, 1H), 8.06 (s, 1H), 7.99 (t, J=1.9 Hz, H), 7.91 (td, J=8.0, 1.9 Hz, 1H), 7.87 (s, 1), 7.73 (dd, J=5.7, 2.1 Hz, 1H), 7.52-7.41 (m, 2H), 7.36-7.25 (m, 2H), 6.80 (s, 11), 5.93 (s, 1H), 3.86 (s, 3H), 3.80 (s, 3H), 3.12 (d, J=11.1 Hz, 2H), 2.63-2.53 (m, 4H), 2.39-2.27 (m, 4H), 2.26-2.19 (m, 1H), 2.15 (s, 3H), 1.82 (d, J=11.5 Hz, 2H), 1.61-1.48 (m, 2H).

Example 10: Preparation of $N^4$-(2-(2-fluorophenyl)pyridin-4-yl)-$N^6$-(2-methoxy-5-(1-methyl-1H-pyrazol-4-yl)-4-morpholinophenyl)pyrimidine-4,6-diamine

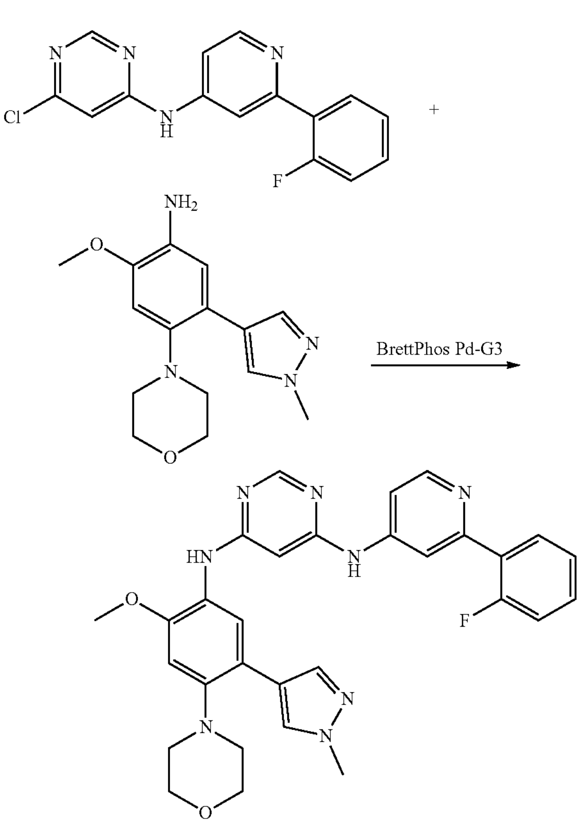

6-chloro-N-(2-(2-fluorophenyl)pyridin-4-yl)pyrimidin-4-anine (100 mg, 0.33 mmol), 2-methoxy-5-(1-methyl-1H-pyrazol-4-yl)-4-morpholinoaniline (106 mg, 0.37 mmol), NaO$^t$Bu (64 mg, 0.67 mmol) and BrettPhos Pd-G3 (30 mg, 0.03 mmol) were added in toluene (15 mL), and then under nitrogen protection, the mixture was heated to 90° C. and stirred overnight. The reaction mixture was cooled to room temperature and filtered. The filtrate was concentrated, and then the residue was separated by the column chromatography to obtain a crude product. The crude product was then separated by a preparative column to obtain $N^4$-(2-(2-fluorophenyl)pyridin-4-yl)-$N^6$-(2-methoxy-5-(1-methyl-1H-pyrazol-4-yl)-4-morpholinophenyl)pyrimidine-4,6-diamine (40.5 mg, yield: 22.0%). MS m/z (ESI): 553.2 $[M+H]^+$.

$^1$H NMR (400 MHz, DMSO-$d_6$) δ 9.62 (s, 1H), 8.46 (s, 1H), 8.43 (d, J=5.6 Hz, 1H), 8.27 (s, 1H), 8.13 (s, 1H), 8.00 (t, J=2.0 Hz, 1H), 7.94-7.88 (m, 2H), 7.75-7.73 (dd, J=5.7, 2.1 Hz, 1H), 7.49-7.44 (m, 2H), 7.34-7.28 (m, 2H), 6.83 (s, 1H), 5.96 (s, 1H), 3.87 (s, 3H), 3.83 (s, 3H), 3.75-3.72 (m, 4H), 2.87-2.83 (m, 4H).

Example 11: Preparation of $N^4$-(2-(2-fluorophenyl)pyridin-4-yl)-$N^6$-(2-methoxy-5-(1-methyl-1H-pyrazol-4-yl)-4-(4-methylpiperazin-1-yl)phenyl)pyrimidine-4,6-diamine

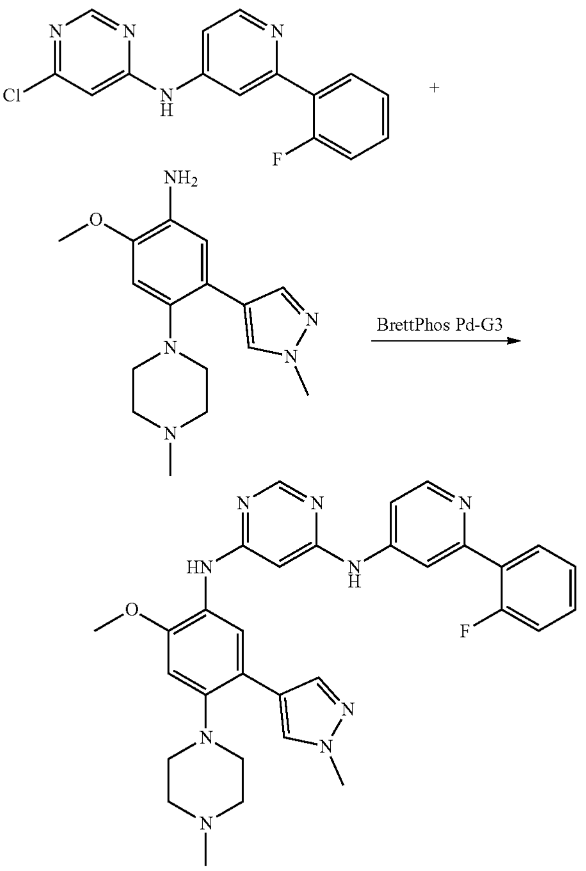

6-chloro-N-(2-(2-fluorophenyl)pyridin-4-yl)pyrimidin-4-amine (62 mg, 0.21 mmol), 2-methoxy-5-(1-methyl-1H-pyrazol-4-yl)-4-(4-methylpiperazin-1-yl)aniline (68 mg, 0.23 mmol), NaO$^t$Bu (40 mg, 0.41 mmol) and BrettPhos Pd-G3 (18 mg, 0.02 mmol) were added in toluene (10 mL), and then under nitrogen protection, the mixture was heated to 90° C. and stirred overnight. The reaction mixture was cooled to room temperature and filtered. The filtrate was concentrated, and then the residue was separated by the column chromatography to obtain a crude product. The crude product was then separated by a preparative column to obtain $N^4$-(2-(2-fluorophenyl)pyridin-4-yl)-$N^6$-(2-methoxy-5-(1-methyl-1H-pyrazol-4-yl)-4-(4-methylpiperazin-1-yl)phenyl)pyrimidine-4,6-diamine (25.5 mg, yield: 21.9%). MS m/z (ESI): 566.2 $[M+H]^+$.

$^1$H NMR (400 MHz, DMSO-$d_6$) δ 9.61 (s, 1H), 8.47-8.40 (m, 2H), 8.27 (s, 1H), 8.06 (s, 1H), 7.99 (t, J=2.0 Hz, 1H), 7.94-7.87 (m, 2H), 7.74-7.72 (dd, J=5.7, 2.2 Hz, 1H), 7.50-7.42 (m, 2H), 7.33-7.28 (m, 2H), 6.81 (s, 1H), 5.94 (s, 1H), 3.86 (s, 3H), 3.81 (s, 3H), 2.88-2.84 (m, 4H), 2.48-2.41 (m, 4H), 2.24 (s, 3H).

Example 12: Preparation of $N^4$-(5-(2-fluorophenyl)pyridin-3-yl)-$N^6$-(2-methoxy-5-methyl-4-(4-(4-methylpiperazin-1-yl)piperidin-1-yl)phenyl)pyrimidine-4,6-diamine

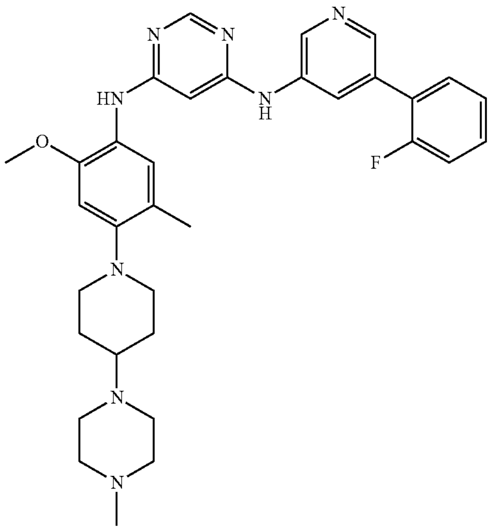 [SMILES: COc1cc(N2CCC(N3CCN(C)CC3)CC2)c(C)cc1Nc1cc(Nc2cncc(-c3ccccc3F)c2)ncn1]

Step 1: Synthesis of 5-(2-fluorophenyl)pyridin-3-amine

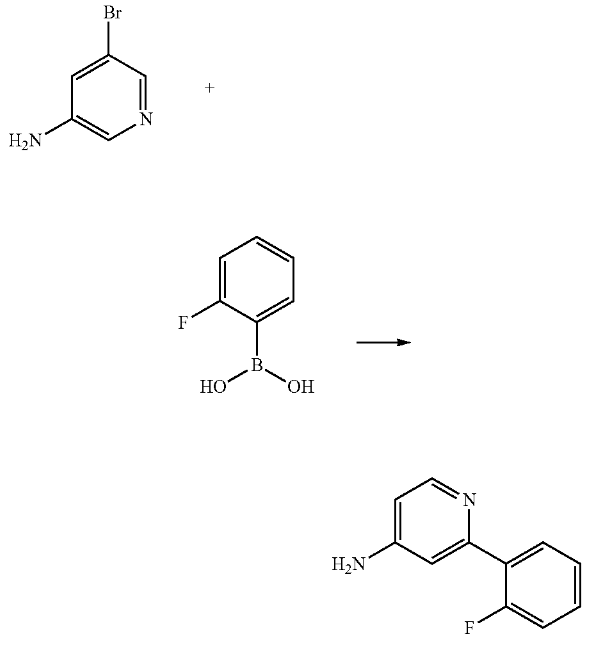

The process refers to step 1 in Example 1.

Step 2: Synthesis of $N^4$-(5-(2-fluorophenyl)pyridin-3-yl)-$N^6$-(2-methoxy-5-methyl-4-(4-(4-methylpiperazin-1-yl)piperidin-1-yl)phenyl)pyrimidine-4,6-diamine

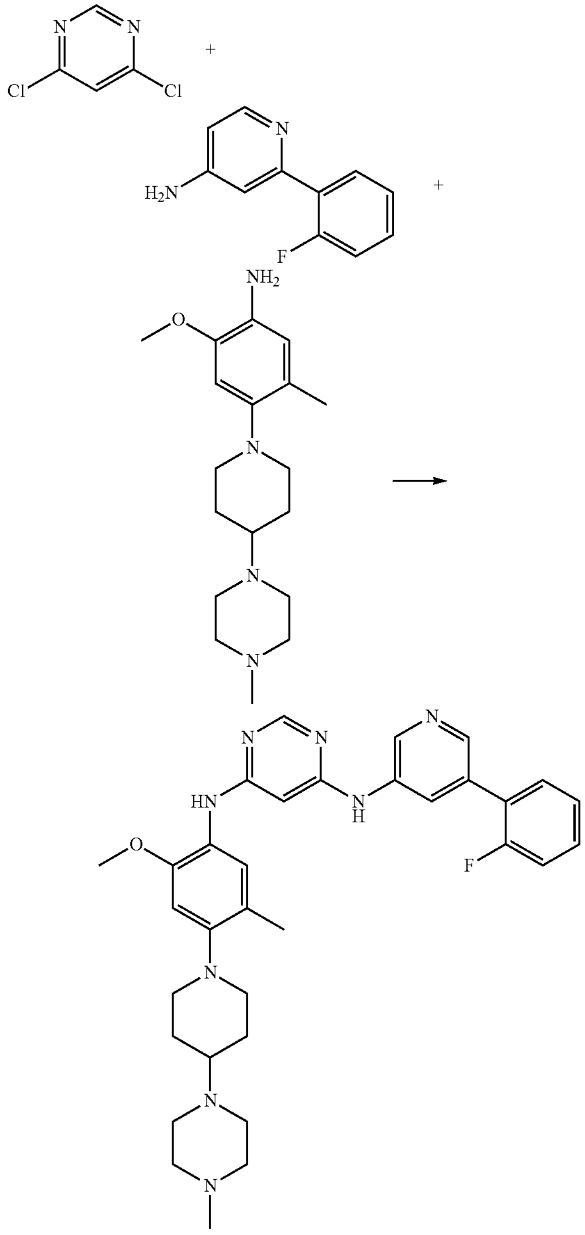

4,6-dichloropyrimidine (60 mg, 0.40 mmol), 5-(2-fluorophenyl)pyridin-3-amine (76 mg, 0.40 mmol) and 2-methoxy-5-methyl-4-(4-(4-methylpiperazin-1-yl)piperidin-1-yl)aniline (130 mg, 0.40 mmol) were dissolved in anhydrous 1,4-dioxane (8 mL), then under nitrogen protection, BrettPhos Pd-G3 (37 mg, 0.04 mmol) and NaO$^t$Bu (77 mg, 0.81 mmol) were added, and the mixture was heated to 85° C. for reaction overnight. The reaction mixture was cooled to room temperature and concentrated. The residue was then separated by the column chromatography to obtain a crude product. The crude product was then separated by the high performance liquid chromatography to obtain $N^4$-(5-(2-fluorophenyl)pyridin-3-yl)-$N^6$-(2-methoxy-5-methyl-4-(4-(4-methylpiperazin-1-yl)piperidin-1-yl)phenyl)pyrimidine-4,6-diamine (14 mg, yield: 6.1%). MS m/z (ESI): 583.2 $[M+H]^+$.

$^1$H NMR (400 MHz, DMSO-$d_6$) δ 9.32 (s, 1H), 8.74 (d, J=2.1 Hz, 1H), 8.30-8.26 (m, 2H), 8.24 (s, 1H), 8.18 (s, 1H), 7.57 (td, J=7.8, 1.8 Hz, 1H), 7.54-7.44 (m, 1H), 7.44-7.29 (m, 2H), 7.21 (s, 1H), 6.70 (s, 1H), 5.85 (s, 1H), 3.75 (s, 3H), 3.09 (d, J=11.3 Hz, 2H), 2.63 (t, J=11.4 Hz, 3H), 2.37-2.25 (m, 5H), 2.16 (s, 3H), 2.15 (s, 3H), 1.86 (d, J=11.9 Hz, 2H), 1.67-1.47 (m, 2H).

Example 13: Preparation of $N^4$-(5-fluoro-2-methoxy-4-(4-(4-methylpiperazin-1-yl)piperidin-1-yl)phenyl)-$N^6$-(2-(2-fluorophenyl)pyridin-4-yl)pyrimidine-4,6-diamine

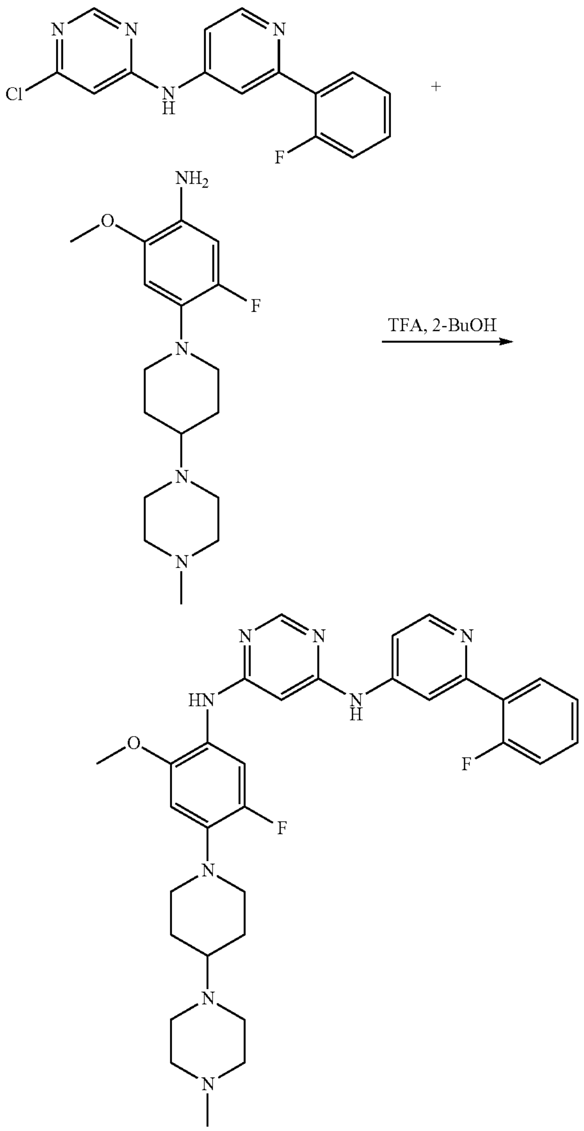

6-chloro-N-(2-(2-fluorophenyl)pyridin-4-yl)pyrimidin-4-amine (101.6 mg, 0.338 mmol) and 5-fluoro-2-methoxy-4-(4-(4-methylpiperazin-1-yl)piperidin-1-yl)aniline (100 mg, 0.307 mmol) were dissolved in 2-butanol (2.0 mL) and then TFA (0.4 mL, 5.385 mmol) was added. Under $N_2$ protection, the mixture was heated to 130° C. in a sealed tube for reaction overnight. The reaction mixture was cooled to room temperature and concentrated. The residue was separated by silica gel column chromatography to obtain $N^4$-(5-fluoro-2-methoxy-4-(4-(4-methylpiperazin-1-yl)piperidin-1-yl)phenyl)-$N^6$-(2-(2-fluorophenyl)pyridin-4-yl)pyrimidine-4,6-diamine (35.0 mg, 0.060 mmol, yield: 19.3%). MS m/z (ESI): 587.2 $[M+H]^+$.

$^1$H NMR (400 MHz, DMSO-$d_6$) δ 9.68 (s, 1H), 8.55 (s, 1H), 8.45 (d, J=5.7 Hz, 1H), 8.31 (d, J=0.9 Hz, 1H), 8.00 (d, J=2.0 Hz, 1H), 7.92 (td, J=7.9, 1.7 Hz, 1H), 7.74 (dd, J=5.8, 2.1 Hz, 1H), 7.57-7.39 (m, 2H), 7.37-7.27 (m, 2H), 6.68 (d, J=8.3 Hz, 1H), 6.14 (s, 1H), 3.80 (s, 3H), 3.39 (d, J=11.7 Hz, 2H), 2.68 (t, J=11.5 Hz, 2H), 2.29 (dd, J=13.7, 8.9 Hz, 5H), 2.14 (s, 3H), 1.85 (d, J=12.3 Hz, 2H), 1.55 (dd, J=13.1, 9.4 Hz, 2H).

Example 14: Preparation of $N^4$-(5-chloro-2-methoxy-4-(4-(4-methylpiperazin-1-yl)piperidin-1-yl)phenyl)-$N^6$-(2-(2-fluorophenyl)pyridin-4-yl)pyrimidine-4,6-diamine

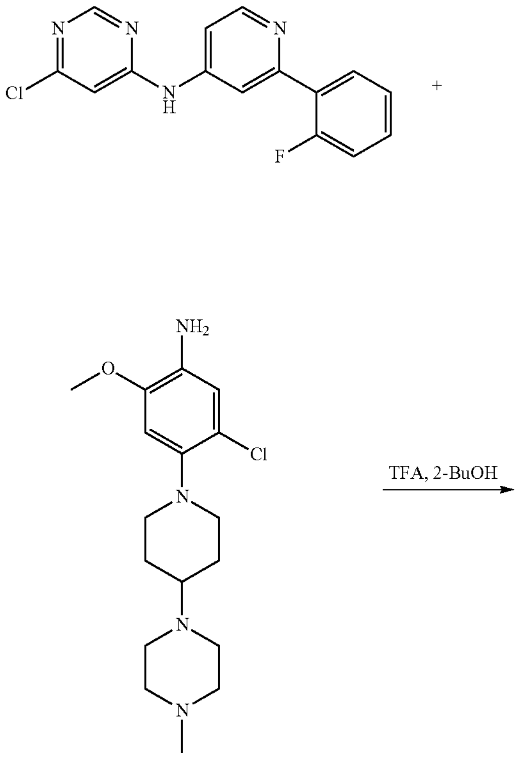

-continued

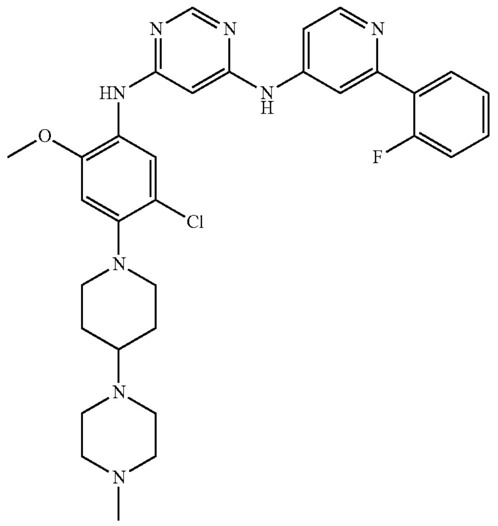

It was synthesized by referring to the preparation in Example 13. MS m/z (ESI): 603.4 $[M+H]^+$.

$^1$H NMR (400 MHz, DMSO-$d_6$) $\delta$ 9.69 (s, 1H), 8.59 (s, 1H), 8.45 (d, J=5.7 Hz, 1H), 8.32 (d, J=0.9 Hz, 1H), 8.00 (d, J=1.9 Hz, 1H), 7.92 (td, J=7.9, 1.7 Hz, 1H), 7.78-7.66 (m, 2H), 7.46 (ddd, J=7.6, 5.3, 1.9 Hz, 1H), 7.37-7.27 (m, 2H), 6.80 (s, 1H), 6.12 (s, 1H), 3.83 (s, 3H), 2.73-2.62 (m, 2H), 2.37-2.24 (m, 5H), 2.14 (s, 3H), 1.86 (d, J=12.1 Hz, 2H), 1.65-1.51 (m, 2H).

Example 15: Preparation of N$^4$-(5-bromo-2-methoxy-4-(4-(4-methylpiperazin-1-yl)piperidin-1-yl)phenyl)-N-(2-(2-fluorophenyl)pyridin-4-yl)pyrimidine-4,6-diamine

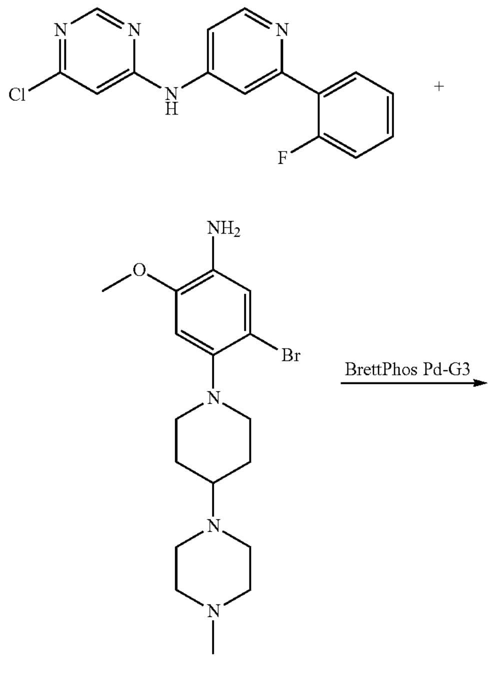

-continued

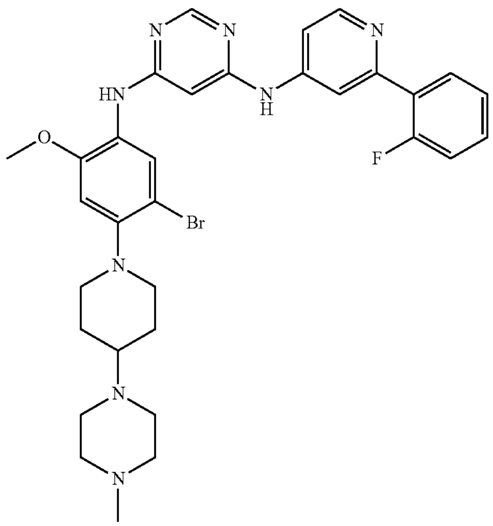

It was synthesized by referring to the preparation in Example 3. MS m/z (ESI): 647.4 $[M+H]^+$.

$^1$H NMR (400 MHz, DMSO-$d_6$) $\delta$ 9.72 (s, 1H), 8.63 (s, 1H), 8.45 (d, J=5.8 Hz, 1H), 8.32 (s, 1H), 8.00 (s, 1H), 7.96-7.86 (m, 2H), 7.75 (dd, J=5.7, 2.1 Hz, 1H), 7.52-7.42 (m, 1H), 7.36-7.28 (m, 2H), 6.83 (s, 1H), 6.12 (s, 1H), 3.83 (s, 3H), 3.28 (t, 2H), 2.94 (t, 2H), 2.71-2.64 (m, 2H), 2.32 (m, 5H), 2.15 (s, 3H), 2.00 (q, J=7.0 Hz, 2H), 1.86 (d, J=11.9 Hz, 2H), 1.59 (q, J=11.0 Hz, 2H).

Example 16: Preparation of N$^4$-(4-(4-(4-ethylpiperazin-1-yl)piperidin-1-yl)-2-methoxy-5-methylphenyl)-N$^6$-(2-(2-fluorophenyl)pyridin-4-yl)pyramidine-4,6-diamine

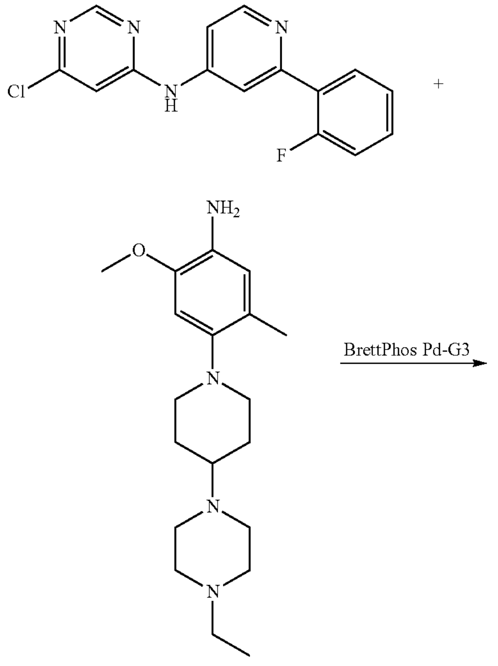

-continued

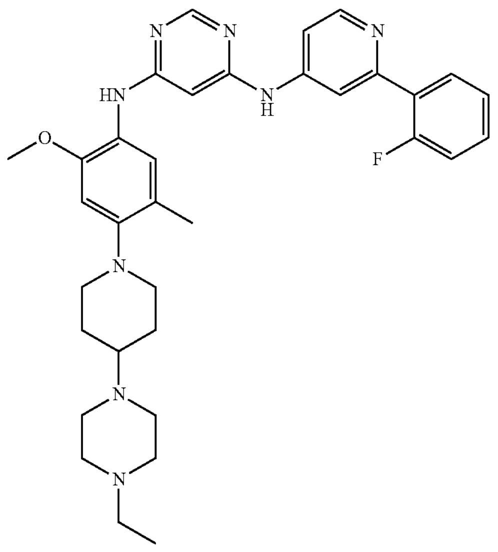

It was synthesized by referring to the preparation in Example 3. MS m/z (ESI): 597.4 $[M+H]^+$.

$^1H$ NMR (400 MHz, DMSO-$d_6$) δ 9.59 (s, 1H), 8.43 (d, J=5.6 Hz, 1H), 8.37 (s, 1H), 8.25 (s, 1H), 7.99 (d, J=2.0 Hz, 1H), 7.91 (td, J=7.9, 1.9 Hz, 1H), 7.73 (dd, J=5.7, 2.1 Hz, 1H), 7.46 (tdd, J=7.5, 5.1, 1.9 Hz, 1H), 7.42-7.27 (m, 2H), 7.20 (s, 1H), 6.72 (s, 1H), 5.90 (s, 1H), 3.76 (s, 3H), 3.10 (d, J=11.3 Hz, 2H), 2.69-2.59 (m, 2H), 2.37 (brs, 4H), 2.29 (q, J=7.4 Hz, 2H), 2.16 (s, 3H), 1.97-1.78 (m, 2H), 1.66-1.48 (m, 2H), 0.98 (t, J=7.1 Hz, 3H).

Example 17: Preparation of $N^4$-(2,5-dichloro-4-(4-(4-methylpiperazin-1-yl)piperidin-1-yl)phenyl)-$N^6$-(2-(2-fluorophenyl)pyridin-4-yl)pyrimidine-4,6-diamine

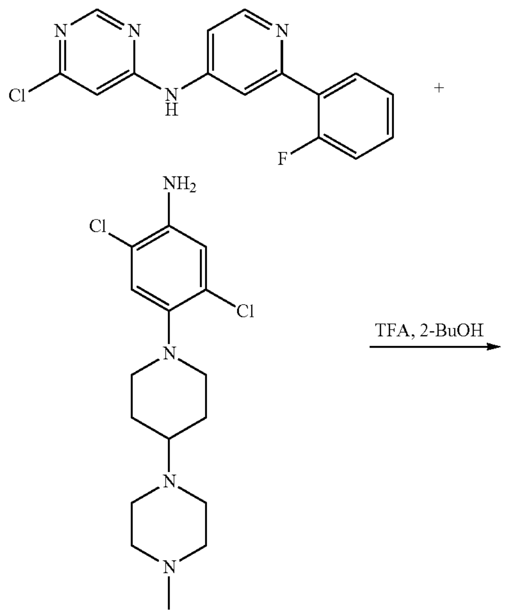

-continued

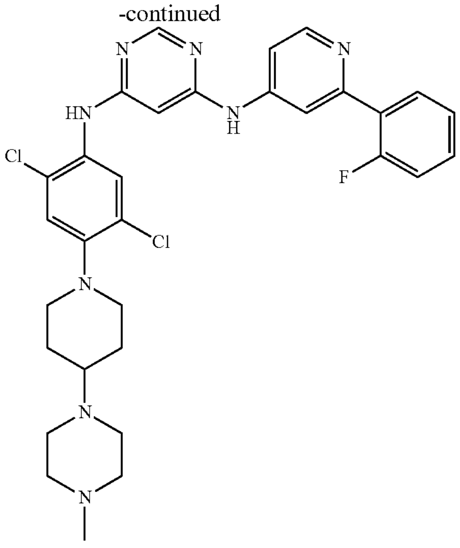

It was synthesized by referring to the preparation in Example 13. MS m/z (ESI): 607.4 $[M+H]^+$.

$^1H$ NMR (400 MHz, DMSO-$d_6$) δ 9.75 (s, 1H), 8.96 (s, 1H), 8.46 (d, J=5.7 Hz, 1H), 8.32 (s, 1H), 8.02 (s, 1H), 7.92 (td, J=7.9, 1.9 Hz, 1H), 7.74 (dd, J=5.7, 2.1 Hz, 1H), 7.69 (s, 1H), 7.47 (tdd, J=7.3, 5.0, 1.9 Hz, 1H), 7.31 (d, J=7.9 Hz, 2H), 7.23 (s, 1H), 6.07 (s, 1H), 2.71-2.61 (m, 2H), 2.37-2.25 (m, 4H), 2.14 (s, 3H), 1.90-1.82 (m, 2H), 1.57 (dd, J=11.9, 3.6 Hz, 2H).

Example 18: Preparation of $N^4$-(2-chloro-5-methyl-4-(4-(4-methylpiperazin-1-yl)piperidin-1-yl)phenyl)-$N^6$-(2-(2-fluorophenyl)pyridin-4-yl)pyrimidine-4-diamine

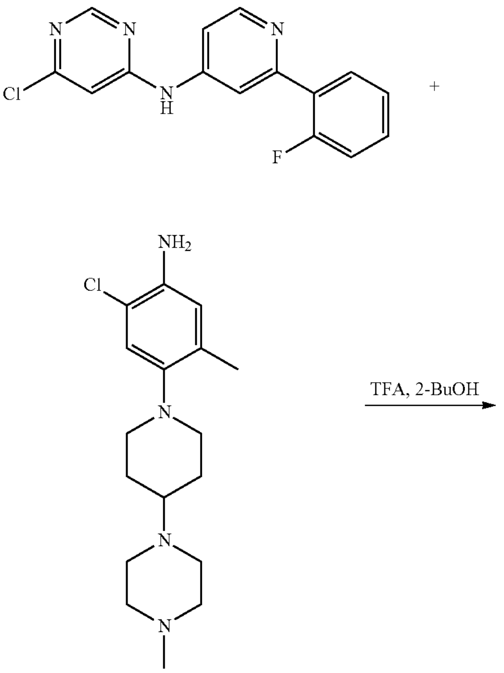

-continued

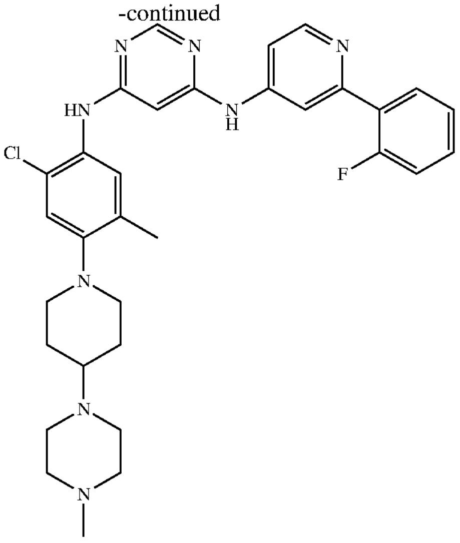

It was synthesized by referring to the preparation in Example 13. MS m/z (ESI): 587.4 $[M+H]^+$.

$^1$H NMR (400 MHz, DMSO-$d_6$) δ 9.67 (s, 1H), 8.82 (s, 1H), 8.44 (d, J=5.8 Hz, 1H), 8.28 (s, 1H), 8.00 (d, J=1.8 Hz, 1H), 7.91 (td, J=7.9, 1.9 Hz, 1H), 7.73 (dd, J=5.7, 2.1 Hz, 1H), 7.46 (ddd, J=7.4, 5.2, 2.1 Hz, 1H), 7.37-7.23 (m, 3H), 7.08 (s, 1H), 5.87 (s, 1H), 3.10 (d, J=11.3 Hz, 2H), 2.60 (t, J=11.6 Hz, 2H), 2.30 (tt, J=11.0, 3.4 Hz, 4H), 2.22 (s, 3H), 2.14 (s, 3H), 1.86 (d, J=12.0 Hz, 2H), 1.56 (tt, J=11.8, 5.9 Hz, 2H).

Biological Test Evaluation (Cell Proliferation Study)

(I) Reagents and Materials

DMEM medium (Gibco, 11965118)

RPMI1640 medium (Gibco, 11875119)

Fetal bovine serum (FBS) (GBICO, Cat #10099-141)

CellTiter-Glo® luminescent cell viability assay kit (Promega, Cat #G7572)

Black transparent flat-bottom 96-well plate (Corning®, Cat #3603)

(II) Instruments

SpectraMax multi-label microplate reader MD, 2104-0010A;

Carbon dioxide incubator, Thermo Scientific 3100 series;

Biological safety cabinet, Thermo Scientific, 1300 series model A2;

Inverted microscope, Olympus, CKX41SF;

Siemens refrigerator, KK25E76TI.

(III) Cell Lines and Culture Conditions

| No. | Cell lines | Cell culture medium | Cell density |
|---|---|---|---|
| 1 | A431 | DMEM + 15% FBS | 5000 |
| 2 | Ba/F3 EGFR-L858R-C797S | RPMI1640 + 10% FBS | 3000 |
| 3 | Ba/F3 EGFR-Del19-C797S | RPMI1640 + 10% FBS | 3000 |
| 4 | Ba/F3 EGFR-L858R | RPMI1640 + 10% FBS | 3000 |
| 5 | Ba/F3 EGFR-Del19 | RPMI1640 + 10% FBS | 3000 |

(IV) Experimental Procedures

1. Cell Culture and Inoculation:
   (1) Cells in the logarithmic growth phase were harvested and counted using a platelet counter. The cell viability was determined by the trypan blue dye exclusion method to ensure cell viability above 90%.
   (2) The cell concentration was adjusted to reach a desired final density; 90 μL of cell suspension was added to a 96-well plate.
   (3) The cells were incubated overnight in the 96-well plate at 37° C., 5% $CO_2$ and with 95% humidity.
2. T0 Benchmark Data:
   (1) 10 μL of PBS was added to each well of the TO plate containing the cells,
   (2) The CTG reagent was thawed and the cell plate was equilibrated to room temperature for 30 min.
   (3) An equal volume of CTG solution was added to each well.
   (4) The cells were lysed by shaking on an orbital shaker for 5 min.
   (5) The cell plate was left to stand at room temperature for 20 min to stabilize the fluorescence signal.
   (6) The fluorescence signal values of TO were read.
3. Dilution and Addition of Compounds
   (1) According to the compound information table, a corresponding volume of DMSO was added to the corresponding compound powder to prepare a 10 mM stock solution.
   (2) A 1000-fold, 3.16-fold-diluted compound solution was prepared.
   (3) The 1000× diluted compound solution was diluted 100-fold with PBS to prepare a 10-fold compound solution with a maximum concentration of 10 μM, including 9 concentrations, with 3.16-fold dilution, and 10 μL of the medicament solution was added to each well of the 96-well plate to seed the cells. Triplicate wells were set for each compound concentration, with a final concentration of DMSO being 0.1%.
   (4) The cells were placed in the 96-well plate containing the medicament at 37° C., 5% $CO_2$ and with 95% humidity, and cultured for 72 hrs before CTG analysis,
4. Fluorescence Signal Reading
   (1) The CTG reagent was thawed and the cell plate was equilibrated to room temperature for 30 min.
   (2) An equal volume of CTG solution was added to each well.
   (3) The cells were lysed by shaking on an orbital shaker for 5 min.
   (4) The cell plate was left to stand at room temperature for 20 min to stabilize the fluorescence signal.
   (5) The fluorescence values were read.
5. Data Processing Data were analyzed using GraphPad Prism 7.0 software and fitted data were regressed using non-linear S-curves to obtain dose-response curves from which $IC_{50}$ values (in nM) were calculated. The specific experimental results are shown in Table 1:

$$\text{Cell viability (\%)} = (Lum\ \text{test medicament} - Lum\ \text{medium control}) / (Lum\ \text{cell control} - Lum\ \text{medium control}) * 100\%.$$

TABLE 1

| Biological Test Results | | | | | |
|---|---|---|---|---|---|
| Example No. | A431 WT | L858R/ C797S | Del19/ C797S | L858R | Del19 |
| 1 | 182 | 9.1 | 3.7 | 3.0 | 3.4 |
| 2 | 554 | 10.4 | 17.4 | 2.9 | 2.8 |
| 3 | 217 | 23.3 | NT | NT | NT |
| 4 | 237 | 12.1 | 12.7 | 6.2 | 6.6 |
| 5 | NT | 53.2 | NT | NT | NT |
| 6 | 1078 | 32.1 | 23.7 | NT | NT |
| 7 | 2500 | 69.1 | NT | NT | NT |
| 8 | 1655 | 40.0 | 34.6 | NT | NT |
| 9 | 1523 | 68.6 | NT | NT | NT |
| 10 | NT | 117 | NT | NT | NT |
| 11 | 306 | 72.6 | NT | NT | NT |
| 12 | 2340 | 77.4 | NT | NT | NT |
| 13 | 182 | 22.8 | 16.9 | NT | NT |
| 14 | 228 | 21.4 | 21.9 | NT | NT |
| 15 | 181 | 18.3 | NT | NT | NT |
| 16 | 177 | 11.3 | 12.9 | 3.9 | 3.1 |
| 17 | 1060 | 87.8 | 85.0 | NT | NT |
| 18 | 984 | 21.7 | 25.1 | NT | NT |

Notes
"NT" is an abbreviation of "Not Tested", and means that an object has not been detected yet.

From the biological activity data of the compounds of the specific examples, the series of compounds of the present invention have strong inhibitory effects on EGFR Del19 mutation, EGFR L858R mutation, EGFR L858R/C797S double mutation or EGFR Del19/C797S double mutation at cellular level, and have high selectivity for EGFR WT.

All documents mentioned in the present invention are incorporated as references, just as each document is individually cited as a reference. In addition, it should be understood that various modifications or changes may be made by those skilled in the art after reading the above disclosure of the present invention, and these equivalent forms also fall within the scope defined by the claims appended hereto.

The invention claimed is:

1. A compound of formula (III), or a stereoisomer or pharmaceutically acceptable salt thereof:

(II)

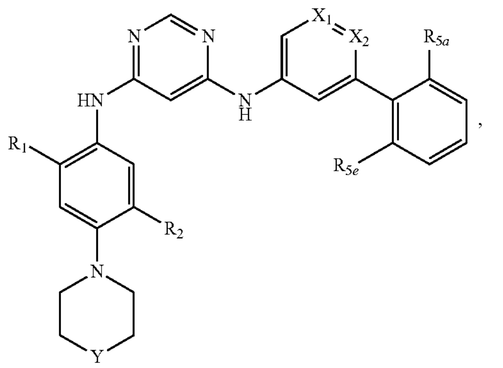

wherein, $X_1$ and $X_2$ are each independently N or CH;

Y is a bond, O, S, $N(R_{14})$, or $C(R_{15}R_{16})$;

$R_1$ is selected from the group consisting of hydrogen, deuterium, halogen, cyano, methyl, ethyl, isopropyl, allyl, vinyl, ethynyl, cyclopropyl, cyclobutyl, morpholinyl, 3-6 membered oxacyclyl, 3-6 membered azacyclyl, hydroxy, methoxy, ethoxy, isopropoxy, cyclopropyloxy, cyclobutyloxy, and 3-6 membered heterocyclyloxy, each of the above $R_1$ groups independently optionally further substituted with one or more substituents selected from the group consisting of deuterium, fluoro, chloro, bromo, hydroxy, cyano, $C_{1-4}$ alkyl, $C_{3-6}$ cycloalkyl, 3-6 membered heterocyclyl, amino, mono$C_{1-4}$ alkylamino, and di$C_{1-4}$ alkylamino;

$R_2$ is selected from the group consisting of hydrogen, deuterium, fluoro, chloro, bromo, cyano, methyl, ethyl, propyl, isopropyl, cyclopropyl, cyclobutyl, cyclopentyl, azacyclobutyl, pyrazolyl, imidazolyl, oxazolyl, and triazolyl, each of the above $R_2$ groups independently optionally further substituted with one or more substituents selected from the group consisting of deuterium; fluoro, chloro, bromo, cyano, methyl, ethyl, $C_{1-4}$ haloalkyl, $C_{1-4}$ deuterioalkyl, $C_{2-4}$ alkenyl, $C_{2-4}$ alkynyl, $C_{3-6}$ cycloalkyl, and 3-6 membered heterocyclyl;

$R_{5a}$ is selected from the group consisting of hydrogen, deuterium, fluoro, chloro, bromo, cyano, $C_{1-4}$ alkyl, $C_{1-4}$ haloalkyl, $C_{1-4}$ deuterioalkyl, and $C_{3-6}$ cycloalkyl;

$R_{5e}$ is selected from the group consisting of hydrogen, deuterium, fluoro, chloro, bromo, cyano, $C_{1-4}$ alkyl, $C_{1-4}$ haloalkyl, $C_{1-4}$ deuterioalkyl, and $C_{3-6}$ cycloalkyl;

$R_{14}$ is selected from the group consisting of hydrogen, deuterium, hydroxy, methyl, ethyl, propyl, isopropyl, $C_{1-4}$ haloalkyl, $C_{1-4}$ deuterioalkyl, $C_{3-6}$ cycloalkyl, 3-6 membered heterocyclyl, $—S(O)_rR_8$, $—C_{0-4}$ alkyl-O—$R_9$, $—C(O)OR_9$, $—C(O)R_{10}$, and $—C(O)NR_{11}R_{12}$; and $R_{15}$ and $R_{16}$ are each independently selected from the group consisting of hydrogen, deuterium, fluoro, chloro, bromo, cyano, $C_{1-4}$ alkyl, $C_{2-4}$ alkenyl, $C_{2-4}$ alkynyl, $C_{3-6}$ cycloalkyl, and 3-6 membered heterocyclyl, or $R_{15}$ and $R_{16}$, together with the carbon atom to which $R_{15}$ and $R_{16}$ are directly attached, form a C(O), $C_{3-6}$ cycloalkyl, or 3-6 membered heterocyclyl, each of the above $R_{15}$ and $R_{16}$ groups optionally further substituted with one or more substituents selected from the group consisting of deuterium, fluoro, chloro, bromo, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, and =O.

2. The compound of formula (III), or the stereoisomer or pharmaceutically acceptable salt thereof, of claim 1, wherein $R_2$ is selected from the group consisting of hydrogen, deuterium, fluoro, chloro, bromo, methyl, ethyl, propyl, isopropyl, cyclopropyl, cyclobutyl, cyclopentyl, azacyclobutyl, pyrazolyl, imidazolyl, oxazolyl, and triazolyl, each of the above $R_2$ groups independently optionally further substituted with one or more substituents selected from the group consisting of deuterium, fluoro, chloro, bromo, cyano, methyl, ethyl, trifluoromethyl, difluoromethyl, trideuteriomethyl, and dideuteriomethyl.

3. The compound of formula (III), or the stereoisomer or pharmaceutically acceptable salt thereof, of claim 1, wherein $R_1$ is selected from the group consisting of hydrogen, deuterium, fluoro, chloro, bromo, methyl, ethyl, isopropyl, cyclopropyl, cyclobutyl, morpholinyl, 3-6 membered oxacyclyl, 3-6 membered azacyclyl, hydroxy, methoxy, ethoxy, isopropoxy, cyclopropyloxy, and cyclobutyloxy, each of the above $R_1$ groups independently optionally further substituted with one or more substituents selected from the group consisting of deuterium, fluoro, chloro, bromo, hydroxy, cyano, methyl, ethyl, propyl, isopropyl, cyclopropyl, cyclobutyl, and cyclopentyl;

$R_{5a}$ is hydrogen; and $R_{5e}$ is selected from the group consisting of hydrogen, deuterium, fluoro, chloro, bromo, cyano, methyl, ethyl, propyl, isopropyl, trifluoromethyl, difluoromethyl, trideuteriomethyl, and dideuteriomethyl.

4. The compound of formula (III), or the stereoisomer or pharmaceutically acceptable salt thereof, of claim 1, wherein $R_{14}$ is selected from the group consisting of hydrogen, deuterium, hydroxy, methyl, ethyl, propyl, isopropyl, trifluoromethyl, difluoromethyl, trideuteriomethyl, dideuteriomethyl, cyclopropyl, cyclobutyl, cyclopentyl, oxacyclobutyl, and azacyclobutyl;

$R_{15}$ and $R_{16}$ are each independently selected from the group consisting of hydrogen, deuterium, fluoro, chloro, bromo, cyano, methyl, ethyl, propyl, isopropyl, cyclopropyl, cyclobutyl, cyclopentyl, oxacyclobutyl, azacyclobutyl, pyrrolidinyl, piperidinyl, morpholinyl, and piperazinyl, or $R_{15}$ and $R_{16}$, together with the carbon atom to which $R_{15}$ and $R_{16}$ are directly attached, form a C(O), cyclopropyl, cyclobutyl, cyclopentyl, oxacyclobutyl, or azacyclobutyl, each of the above $R_{15}$ and $R_{16}$ groups optionally further substituted with one or more substituents selected from the group consisting of deuterium, fluoro, chloro, bromo, cyano, methyl, ethyl, propyl, isopropyl, trifluoromethyl, difluoromethyl, trideuteriomethyl, dideuteriomethyl, cyclopropyl, cyclobutyl, cyclopentyl, oxacyclobutyl, azacyclobutyl, and =O.

5. A compound, a stereoisomer thereof, or a pharmaceutically acceptable salt thereof, selected from the group consisting of:

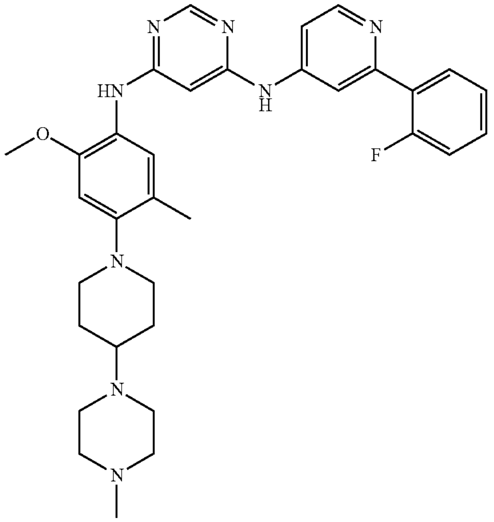
,

-continued

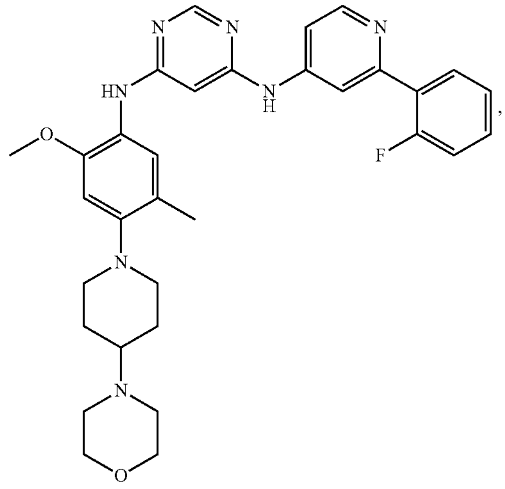
,

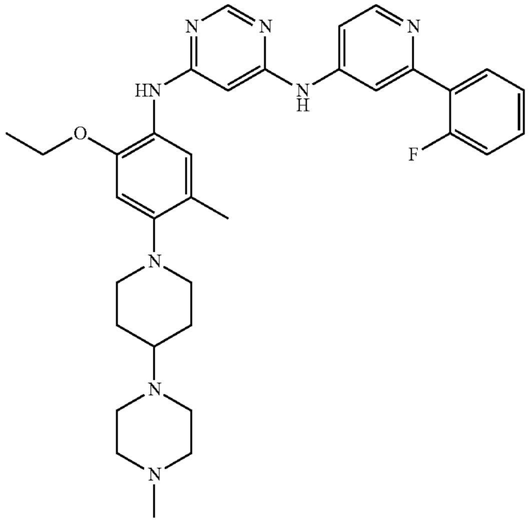
,

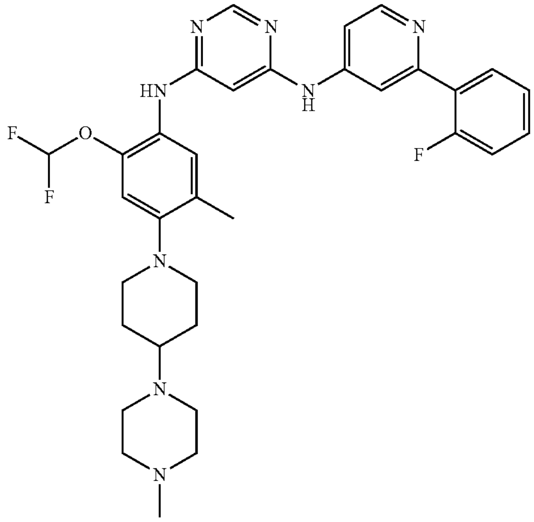
,

-continued
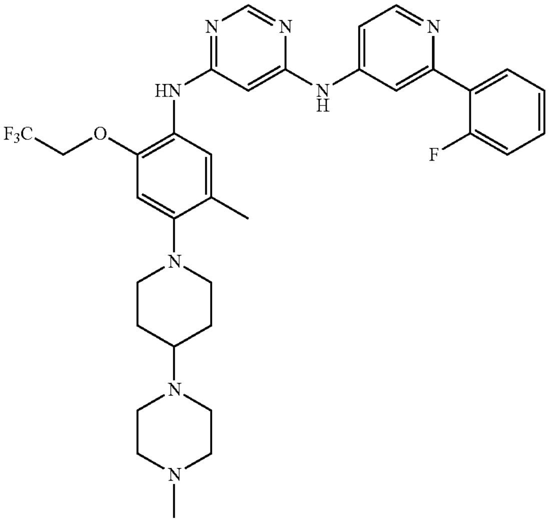,
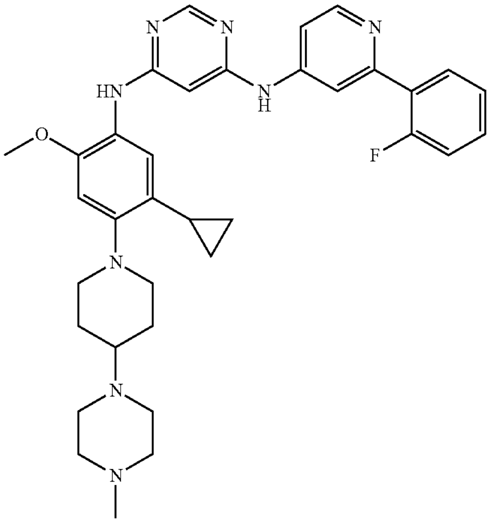,
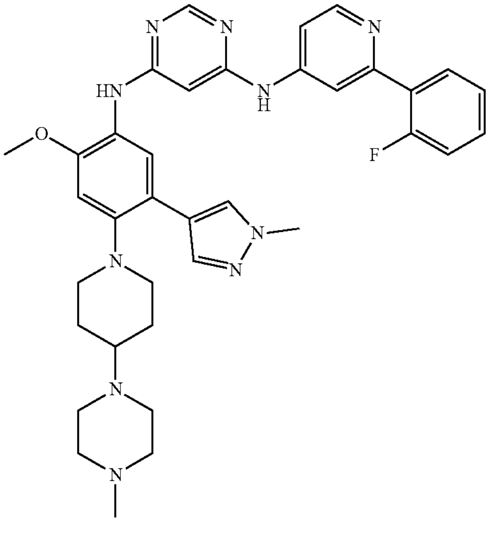,
-continued
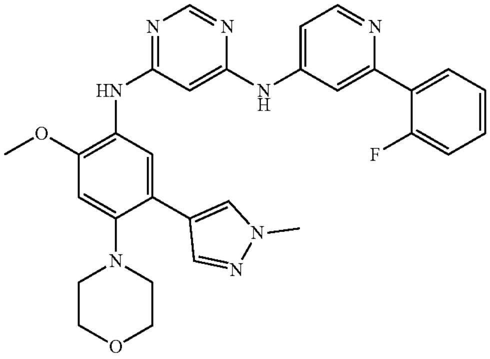,
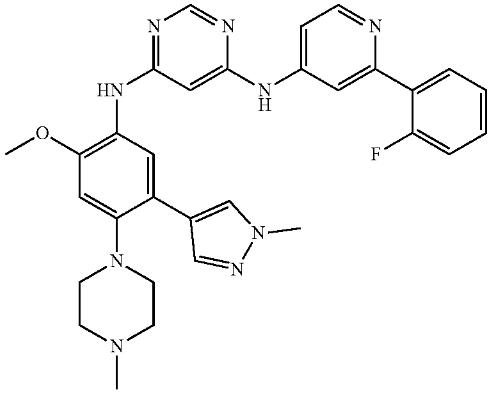,
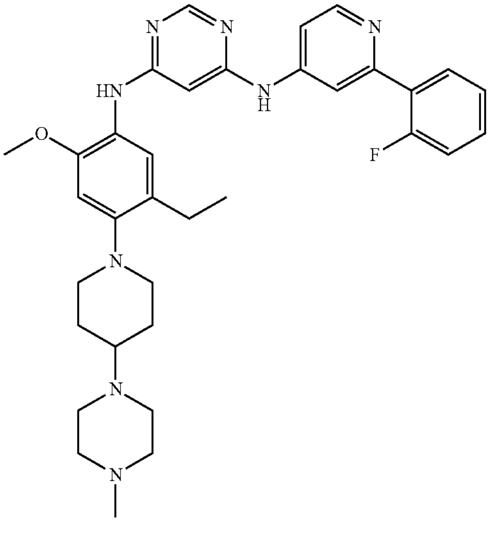, -continued
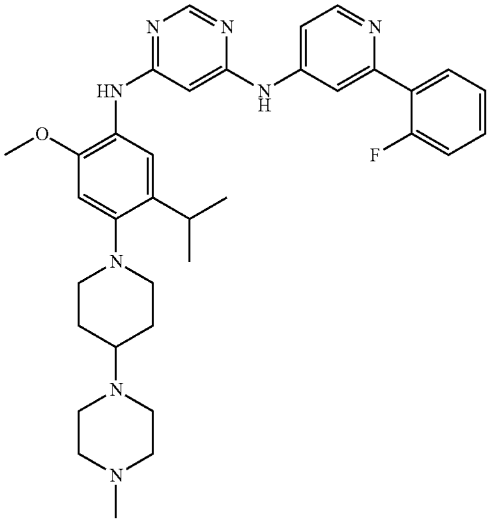
,
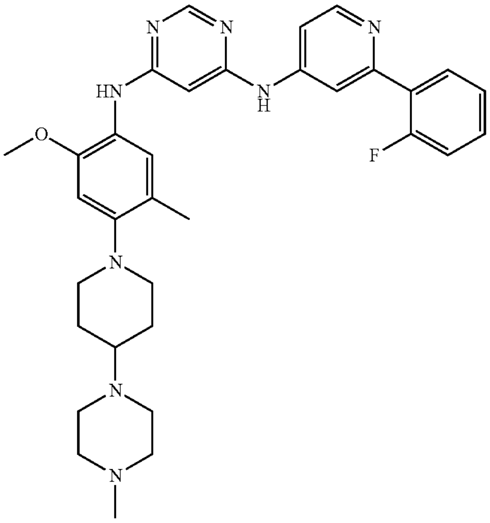
,
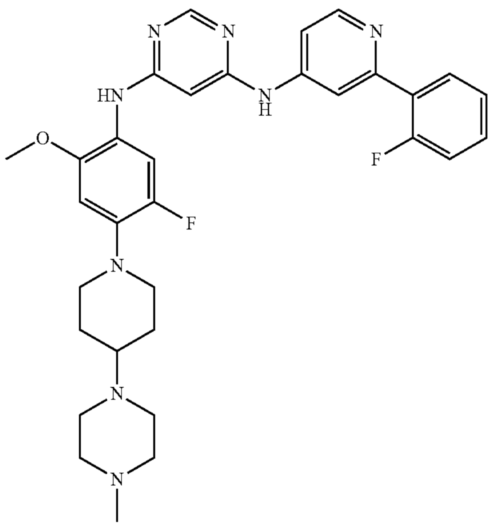
,
-continued
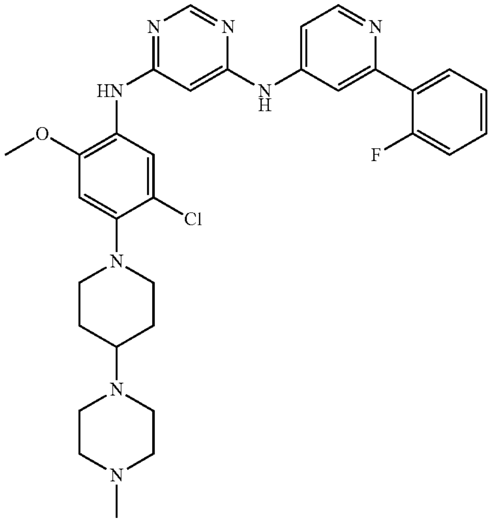
,
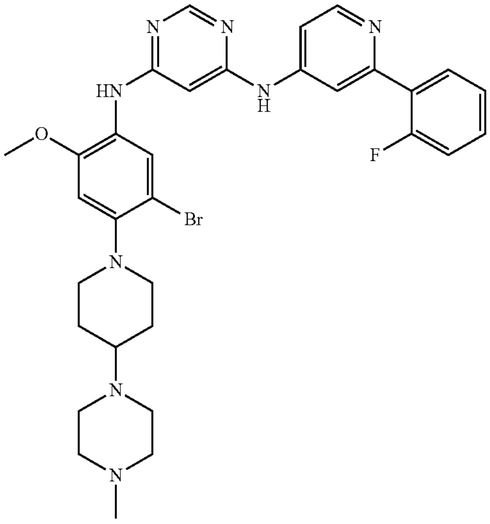
,
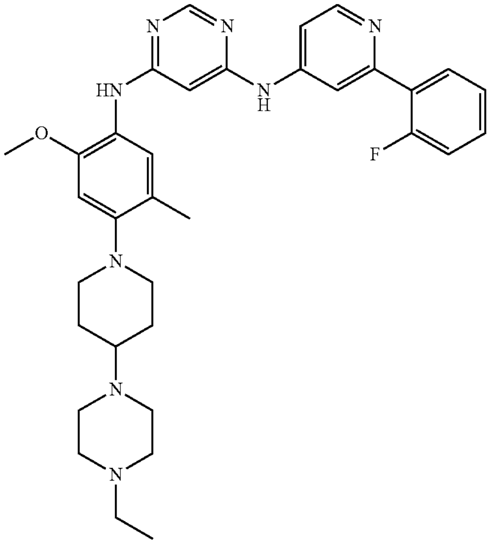
, -continued

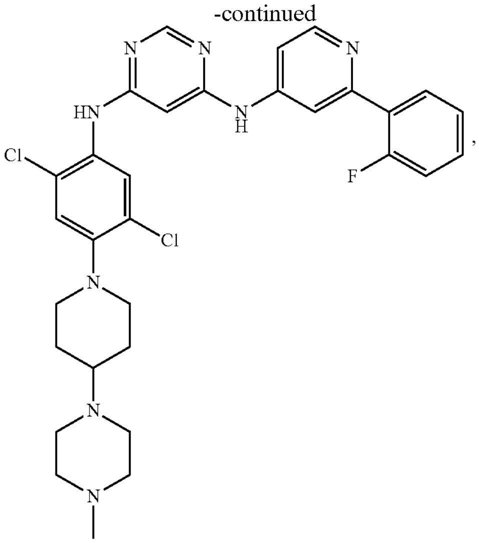

, and

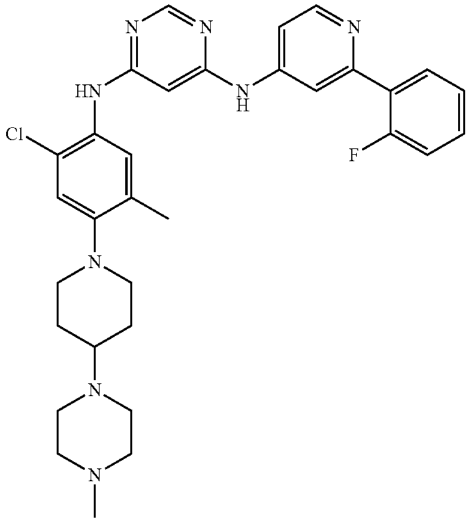

.

6. A pharmaceutical composition comprising a compound according to claim 5, a stereoisomer thereof, or a pharmaceutically acceptable salt thereof, and a pharmaceutically acceptable carrier.

7. A method for treating a disease associated with EGFR Del19 mutation, EGFR L858R mutation, EGFR L858R/C797S double mutation, or EGFR Del19/C797S double mutation in a subject in need thereof, comprising administering to the subject, a compound according to claim 5, a stereoisomer thereof, or a pharmaceutically acceptable salt thereof.

8. The method of claim 7, wherein the disease is lung cancer, pancreatic cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma.

9. The method of claim 8, wherein the lung cancer is non-small cell lung cancer; the gastrointestinal tumor is colon cancer or gastric cancer; the head and neck tumor is head and neck cancer; the breast and other gynecological tumors are breast cancer, ovarian cancer or uterine cancer.

10. A pharmaceutical composition comprising a compound according to claim 1, or the stereoisomer or pharmaceutically acceptable salt thereof, and a pharmaceutically acceptable carrier.

11. A method for treating a disease associated with EGFR Del19 mutation, EGFR L858R mutation, EGFR L858R/C797S double mutation, or EGFR Del19/C797S double mutation in a subject in need thereof, comprising administering to the subject, a compound according to claim 1, or the stereoisomer or pharmaceutically acceptable salt thereof.

12. The method of claim 11, wherein the disease is lung cancer, pancreatic cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma.

13. The method of claim 12, wherein the lung cancer is non-small cell lung cancer; the gastrointestinal tumor is colon cancer or gastric cancer; the head and neck tumor is head and neck cancer; the breast and other gynecological tumors are breast cancer, ovarian cancer or uterine cancer.

* * * * *